US009566282B2

(12) United States Patent
Bhatia et al.

(10) Patent No.: US 9,566,282 B2
(45) Date of Patent: Feb. 14, 2017

(54) METHODS FOR IDENTIFYING AND VALIDATING SELECTIVE ANTI-CANCER STEM CELL AGENTS

(75) Inventors: Mickie Bhatia, Hamilton (CA); Tony Collins, Hamilton (CA); Eleftherios Sachlos, Hamilton (CA); Ruth Munoz Risueno, Hamilton (CA)

(73) Assignee: MCMASTER UNIVERSITY, Hamilton, ON (CA)

( * ) Notice: Subject to any disclaimer, the term of this patent is extended or adjusted under 35 U.S.C. 154(b) by 30 days.

(21) Appl. No.: 13/605,609

(22) Filed: Sep. 6, 2012

(65) Prior Publication Data

US 2013/0065887 A1 Mar. 14, 2013

Related U.S. Application Data

(63) Continuation-in-part of application No. PCT/CA2012/000175, filed on Feb. 28, 2012.

(60) Provisional application No. 61/447,362, filed on Feb. 28, 2011.

(51) Int. Cl.
  *A61K 31/549* (2006.01)
  *A61K 31/5415* (2006.01)
  *G01N 33/50* (2006.01)
  *G01N 33/574* (2006.01)
  *C12Q 1/68* (2006.01)
  *G01N 33/94* (2006.01)

(52) U.S. Cl.
  CPC ......... *A61K 31/5415* (2013.01); *C12Q 1/6886* (2013.01); *G01N 33/5011* (2013.01); *G01N 33/574* (2013.01); *G01N 33/57426* (2013.01); *G01N 33/57492* (2013.01); *G01N 33/57496* (2013.01); *G01N 33/9413* (2013.01); *G01N 2500/10* (2013.01); *G01N 2800/52* (2013.01); *G01N 2800/56* (2013.01)

(58) Field of Classification Search
  None
  See application file for complete search history.

(56) References Cited

U.S. PATENT DOCUMENTS

| 6,180,357 | B1 | 1/2001 | Young | |
|---|---|---|---|---|
| 8,058,243 | B2 | 11/2011 | Tyers | |
| 2006/0040376 | A1* | 2/2006 | Cunningham et al. | 435/287.1 |
| 2007/0293465 | A1* | 12/2007 | Shenk et al. | 514/183 |
| 2009/0197310 | A1* | 8/2009 | Lam et al. | 435/119 |

FOREIGN PATENT DOCUMENTS

| CA | 2 655 807 | 12/2007 |
|---|---|---|
| WO | 2005/027842 | 3/2005 |
| WO | 2006/051405 | 5/2006 |
| WO | 2007/092196 | 8/2007 |
| WO | WO2007/123468 | * 11/2007 |
| WO | 2009/033033 | 3/2009 |
| WO | 2009/126310 | 10/2009 |
| WO | 2011026222 | 3/2011 |
| WO | 2012/116432 | 9/2012 |

OTHER PUBLICATIONS

Gasparri et al (Journal of Biomolecular Screening, 2004, vol. 9, pp. 232-243).*
Brideau et al (Journal of Biomolecular Screening, 2003, vol. 8, pp. 634-647).*
Niu, Chao et al., Studies on Treatment of Acute Promyelocytic Leukemia With Arsenic Trioxide: Remission Induction, Follow-Up, and Molecular monitoring in 11 Newly Diagnosed and 47 Relapsed Acute Promyelocytic Leukemia Patients; Blood; 1999, 94:3315-3324.
Zheng, Rui et al., Targeted inhibition of FLT3 overcomes the block to myeloid differentiation in 32 Dc13 cells caused by expression of FLT3/ITD mutations; Blood; 2002, 100:4154-4161.
Chadwick, Kristin et al, Cytokines and BMP-4 promote hematopoietic differentiation of human embryonic stem cells; Blood; 2003, 102:906-915.
Guan, Yinhgui et al., Detection, isolation, and stimulation of quiescent primitive leukemic progenitor cells from patients with acute myeloid leukemia (AML); Blood; 2003, 101:3142-3149.
Smith, B. Douglas et al., Single-agent CEP-701, a novel FLT3 inhibitor, shows biologic and clinical activity in patients with relapsed or refractory acute myeloid leukemia; Blood; 2004, 103:3669-3676.
Recher, Christian, et al., Antileukemic activity of rapamycin in acute myeloid leukemia; Blood; 2005, 105:2527-2534.
Dick, John E., Stem cell concepts renew cancer research; Blood; 2008; 112:4793-4807.
Taussig, David C., et al., Anti-CD38 antibody-mediated clearance of human repopulating cells masks the heterogeneity of leukemia-initiating cells; Blood; 2008; 112:568-575.
Wang, Zhen-Yi, Acute promyelocytic leukemia: from highly fatal to highly curable; Blood; 2008; 111: 2505-2515.
Sanz, Miguel A,. et al., Management of acuted promyelocytic leukemia: recommendations from an expert panel on behalf of the European LeukemiaNet; Blood; 2009, 113:1875-1891.
Di Carlo, R., et al. Steroid, Prolactin, and Dopamine Receptors in Normal and Pathologic Breast Tissue; Department of Experimental Pharmacology University of Naples; pp. 559-562.
Dalton, So, et al., Cancer risk among users of neuroleptic medication: a population-based cohort study; British Journal of Cancer (2006) 95, 934-939.

(Continued)

*Primary Examiner* — Karen Canella
(74) *Attorney, Agent, or Firm* — Ferris H. Lander, Inc.

(57) ABSTRACT

Described are methods of treating a cancer comprising administering to a subject in need thereof an effective amount of a dopamine receptor (DR) antagonist. The DR antagonist may be a phenothiazine derivative, such as thioridazine or chlorpromazine. Optionally, the cancer is acute myeloid leukemia. Also described are methods for identifying subjects with cancer, methods for providing a prognosis for a subjects with cancer and methods for identifying subjects likely to be responsive to therapy with DR receptor antagonists. Methods for identifying cancer stem cells and chemotherapeutic compounds that are DR receptor antagonists as also provided. Also described are methods for the identification and validation of agents that target cancer stem cells.

34 Claims, 40 Drawing Sheets

(56) References Cited

OTHER PUBLICATIONS

Dent, Rebecca, et al., Triple-Negative Breast Cancer: Clinical Features and Patterns of Recurrence; Clinical Cancer Research, 2007; 13:4429-4434.
Desbordes, Sabrina C., et al., High-Throughput Screening Assay for the Identification of Compounds Regulating Self-Renewal and Differentiation in Human Embryonic Stem Cells; Cell Stem Cell; 2, 602-612, Jun. 2008.
Diallo, Jean-Simon et al., A High-throughput Pharmacoviral Approach Identifies Novel Oncolytic Virus Sensitizers, Molecular Therapy, vol. 18 No. 6, 1123-1129.
Dick, John E., Looking ahead in cancer stem cell research, Nature Biotechnology, vol. 27, No. 1, Jan. 2009.
Driver, Jane A., et al., A Prospective Cohort Study of Cancer Incidence Following the Diagnosis of Parkinson's Disease, Cancer Epidemiol Biomarkers Prev 2007; 16: 1260-1265, Jun. 4, 2007.
Eppert, Kolja, et al, Stem cell gene expression programs influence clincal outcome in human leukemia, nature medicine, vol. 17, No. 9, Sep. 2011.
Estey, Elihu, Acute myeloid leukaemia, Lancet 2006, 368:1894-907.
Fibach, Eitan, et al., Control of Normal Differentiation of Myeloid Leukemic Cells to Macrophages and Granulocytes, Proc. Nat. Acad. Sci USA, vol. 70, No. 2, pp. 343-346, Feb. 1973.
Frese, Kristopher K., et al., Maximizing mouse cancer models, Nature Reviews, Cancer, vol. 7, Sep. 2007, pp. 645-658.
Friend, Charlotte, et al., Hemoglobin Synthesis in Murine Virus-Induced Leukemic Cells In Vitro: Stimulation of Erythroid Differentiation by Dimethyl Sulfoxide, Proceedings of the National Academy of Sciences, vol. 68, No. 2, pp. 378-383, Feb. 1971.
Gupta, Piyush B., et al., Identification of Selective Inhibitors of Cancer Stem Cells by High-Throughput Screening, Cell 138, 645-659, Aug. 21, 2009, pp. 645-659.
Hotta, Akitsu, et al., Isolation of human iPS cells using EOS lentiviral vectors to select for pluripotency, Nature Methods, vol. 6, No. 5, May 2009 pp. 370-379.
Inglese, James, et al., Reporting data from high-throughput screening of small-molecule libraries, Nature Chemical Biology, vol. 3, No. 8, Aug. 2007, pp. 438-441.
Jemal, Ahmedin, et al., Cancer Statistics, 2010, CA CancerJ Clin 2010; 60:277-300.
Jordan, Craig T., Cancer Stem Cells: Controversial or Just Misunderstood?, Cell Stem Cell 4, Mar. 6, 2009 pp. 203-205.
Koistinen, P., et al., Regulation of the acute myeloid leukemia cell line OCI/AML-2 by endothelial nitric oxide synthase under the control of a vascular endothelial growth factor signaling system, Leukemia (2001), 15, 1433-1441.
Lapidot, Tsvee, et al., A cell initiating human acute myeloid leukaemia after transplantation into SCID mice, Nature, vol. 367, Feb. 17, 1994, pp. 645-648.
Lee, Jae Y., et al., mTOR Activation Induces Tumor Suppressors that Inhibit Leukemogensis and Deplete hematopoietic Stem Cells after Pten Deletion, Cell Stem Cell, 7, 593-605, Nov. 5, 2010.
Li, Xiaoxian, et al., Intrinsic Resistance of Tumorigenic Breast Cancer Cells to Chemotherapy, Articles JNCI, vol. 100, Issue 9, May 7, 2008.
Little, Karley Y., et al., Cocaine Induction of Dapamine Transporter Trafficking to Plasma Membrane, Molecular Pharmacology, 61:436-445, 2002.
Machalinski, Boguslaw, et al., In Vivo and in Virtro Studies on the Toxicity of Hoechst 33342 (Ho342). Implications for Employing Ho342 for the Isolation of Haematopoietic Stem Cells, Annals of Transplantation, vol. 3, No. 3, 1998, pp. 5-13.
Nasr, Rihab, et al., Eradication of acute promyelocytic leukemia-initiating cells through PML-RARA degraditon, Nature Medicine, vol. 14, No. 12, Dec. 2008.
Nichols, Jennifer, et al., Formation of Pluripotent Stem Cells in the Mammalian Embryo Depends on the POU Transcription Factor Oct4, Cell, vol. 95, 379-391, 1998.
Niwa, Hitoshi, et al., Quantitative expression of Oct-3/4 defines differentiation, dedifferentiation or self-renewl of ES cells, Nature Genetics, vol. 24, Apr. 2000, pp. 372-376.
Raj, Lakshmi, et al., Selective killing of cancer cells by a small molecue targeting the stress response to ROS, Nature, vol. 475, Jul. 14, 2011, pp. 231-234.
Reya, Tannishtha, et al, Stem cells, cancer, and cancer stem cells, Nature, vol. 414, Nov. 1, 2001, pp. 105-110.
Sachs, Leo, The Differentiation of Myeloid Leukaemia Cell: New Possibilities for Therapy, British Journal of Haematology, 1978, 40, 509-517.
Sachs, Leo, Control of normal cell differentiation and the phenotypic reversion of malignancy in myeloid leukaemia, Nature, vol. 274, Aug. 10, 1978, pp. 535-539.
Sanz, Miguel A., Treatment of Acute Promyelocytic Leukemia, Hematology 2006, pp. 147-156.
Shoemaker, Robert H., The NC160 human tumour cell line anti-cancer drug screen, Nature Reviews, Cancer, vol. 6, Oct. 2006, pp. 813-823.
Smith, Thomas J., et al., 2006 Update of Recommendations for the Use of White Blood Cell Growth, Journal of Clinical Onocology, vol. 24, No. 19, Jul. 1, 2006 pp. 3187-3205.
Tefferi, Ayalew, et al., The 2008 World Health Organization Classification System for Myeloproliferative Neoplasms, Cancer, Sep. 1, 2009, pp. 3842-3847.
Vannucchi, Alessandro M., et al., Advances in Understanding and Management of Myeloproliferative Neoplasms, CA: Cancer Journal for Clinicians, 2009; 59:171-191.
Visvader, Jane, et al., Cancer stem cells in solid tumours: accumulating evidence and unresolved questions, Nature Reviews, Cancer, vol. 9, Oct. 2008, pp. 755-768.
Werbowetski-Ogilvie, Tamra, et al., Characterization of human embryonic stem cells with features of neoplastic progression, Nature Biotechnology, vol. 27, No. 1, Jan. 2009.
Xu, Ren-He, et al., BMP4 initiates human embryonic stem cell differentiation to trophoblast, Nature Biotechnology, Dec. 2002, vol. 20, pp. 1261-1264.
Yilmaz, Omer H., et al., Pten dependence distinguishes haematopoietic stem cells from leukaemia-initiating cells, Nature, vol. 441, May 25, 2006, pp. 475-482.
Ying, Qi-Long, et al., BMP Induction of Id Proteins Suppresses Differentiation and Sustains Embryonic Stem Cell Self-Renewal in Collaboration with Stats, Cell, vol. 115, 281-292, Oct. 31, 2002.
Yoshida, Hitoshi, et al., Accelerated Degradation of PML-Retinoic Acid Receptor alpha (PML-RARA) Oncoprotein by All-trans-Retinoic Acid in Acute Promyelocytic Leukemia: Possible Role of the Proteasome Pathway, Cancer Research 1996; 56:2945-2948.
Zhelev, Zhivko, et al., Phenothiazines suppress proliferation and induce apoptosis in cultured leukemic cells without any influence on the viability of normal lymphocytes Phenothiazines and leukemia; Cancer Chemother Pharmacol; 2004; 53:267-275.
Zhu, Jun, et al, Arsenic-induced PML targeting onto nuclear bodies: Implications for the treatment of acute promyelocytic leukemia; Proc. Natl. Acad. Sci. USA, vol. 94, pp. 3978-3983, Apr. 1997.

\* cited by examiner

A

B

Thio = Thioridazine 10uM
Chlor = Chlorpromazine 10uM

METHODS FOR IDENTIFYING AND VALIDATING SELECTIVE ANTI-CANCER STEM CELL AGENTS

CROSS REFERENCE TO RELATED APPLICATIONS

This application is a continuation-in-part of PCT/CA2012/000175 filed on Feb. 28, 2012, which claims priority to U.S. Provisional Patent Application No. 61/447,362 filed on Feb. 28, 2011, all of which are hereby incorporated by reference in their entirety.

FIELD OF THE DISCLOSURE

The disclosure relates to methods for the prognosis or treatment of cancer and screening methods and particularly to methods for the prognosis or treatment of cancer that target dopamine receptors and screening methods for the identification and validation of agents that target cancer stem cells.

BACKGROUND OF THE DISCLOSURE

Increasing evidence suggests that cancer/tumor development is due to a rare population of cells, termed cancer stem cells (CSCs) (Dick, 2009; Jordan, 2009; Reya et al., 2001) that are uniquely able to initiate and sustain disease. In addition, experimental evidence indicates that conventional chemotherapeutics, characterized by their ability to inhibit cell proliferation of cancer cell lines (Shoemaker, 2006) or reduce tumor burden in murine models (Frese and Tuveson, 2007), are ineffective against human CSCs (Guan et al., 2003; Li et al., 2008). This resistance to chemotherapeutics is coupled with indiscriminate cytotoxicity that often affects healthy stem and progenitor cells, leading to dose restriction and necessitating supportive treatment (Smith et al., 2006). Recent examples along these lines include selective induction of apoptosis (Gupta et al., 2009; Raj et al., 2011) that remains to be tested in normal SCs and in the human system. Accordingly, the identification of agents that target CSCs alone is now critical to provide truly selective anti-cancer drugs for pre-clinical testing.

Normal and neoplastic SCs are functionally defined by a tightly controlled equilibrium between self-renewal vs. differentiation potential. In the case of CSCs, this equilibrium shifts towards enhanced self-renewal and survival leading to limited differentiation capacity that eventually allows for tumor growth. In contrast to direct toxic effects that equally affect normal SCs, an alternative approach to eradicate CSCs is by modification of this equilibrium in favor of differentiation in an effort to exhaust the CSC population. The identification of molecules that selectively target somatic CSCs while sparing healthy SC capacity would therefore be useful for the development of novel diagnostics and therapeutic treatments to selectively target human CSCs.

Methods of discovering anti-cancer compounds which have a selective effect on cancer cells compared to the compounds' effect on normal cells has been described (U.S. Pat. No. 6,180,357) in which anti-CSC drugs have been discovered. However the identification of CSCs require advances in technology. There are several advances required for discovering selective anti-CSC compounds. Some of these include growing high enough numbers of both CSC and normal stem cells (NSCs), having these cells stay in the non-differentiated state, having stem cells which are sufficiently robust for high throughput screening which include robotic handling, dispensing of solutions, transport, and development of relevant stem cell endpoints suitable for high throughput screening. The number of cells available for high throughput is a major technical limitation. Primary isolation is challenging since stem cells are rare in vivo and therefore culturing stem cells permits amplification of the number of stem cells available. Stem cells in culture tend to differentiate and not retain their stem cell characteristics in culture. An example of the difference between stem cell culture and general cell culture is that stem cell culture requires antibiotic free conditions to prevent differentiation. The cell number limitation is apparent in Kondo (WO2006051405A2) since the selection of side populations (as a surrogate of a CSC) by Hoechst 3334 is limiting, given that this dye is toxic to stem cells (Machaliński et al., 1998). In bulk culture, as disclosed in Kondo, a side population forms two populations of cells, a side population and a non-side population of cells. The culture does not maintain a pure group of side population cells and requires re-isolation of the side population with Hoechst 3334 thereby diminishing the number of cells. This issue also hinders determination of endpoints of the mixed cells in culture, since a pure population cannot be monitored directly. Further, subculture, and sub-population analysis is not possible because cell culture creates mixed populations. Although Kondo claims methods for discovering selective CSC compounds the inability to maintain pure cell populations, demonstrate normal cell effects by the same compounds, and compare them to the disclosed side population as a model of CSC in a high through put manner is a limitation of the current state of the art for discovering CSC selective drugs.

Likewise, Tyers (U.S. Pat. No. 8,058,243), illustrates other limitations in the current art. Tyers discloses a clonogenic neurosphere assay to identify potent and/or selective modulators of proliferation, differentiation and/or renewal of neural precursor cells, neural progenitor cells and/or self-renewing and multipotent neural stem cells. The screen was directed to compounds active in a stem cell assay, and not necessarily targeting a CSC. The counter screen was an astrocyte cell line rather than a normal stem cell line so that the counter screen is detecting stem cell vs. differentiated cell activity rather than selective CSC vs. NSC activity. From the active compounds they disclosed testing a subset of twelve (12) against medulloblastoma precursor cells which are enriched for CSCs but are not a pure population of CSCs. The discovery of anti-CSC compounds relied on finding active compounds against neurosphere cells and further testing. Since neurospheres contain stem cells and progenitor cells of the neural lineage the facility to discover anti-CSC selective compounds is precluded because the first step of their screen is directed to normal stem cells. Thus in Tyers the challenge of discovering anti-CSC compounds through high throughput is apparent since they teach identifying active stem cell compounds first through high throughput screening, then testing a sub-set on CSC enriched cells.

Hematological malignancies are types of cancer that affect blood, bone marrow and lymph nodes. Hematological malignancies may derive from either of the two major blood cell lineages: myeloid and lymphoid cell lines. Examples of myeloid malignancies include acute myeloid leukemia and chronic myeloid leukemia.

While myeloid malignancies are all generally considered to arise from precursors of the myeloid lineage in the bone marrow, they are highly divergent in presentation, pathology and treatment. For example, the 2008 World Health Organization Classification for Myeloproliferative Neoplasms (See Tefferi et al. *Cancer*, September 1$^{st}$, pp. 3842-3847 (2009); also Vannucchi et al. Advances in Understanding and Management of Myeloproliferative Neoplasms *CA Cancer J. Clin.* 2009; 59:171-191, both hereby incorporated by reference), identifies 5 different classification schemes for myeloid neoplasms, and places acute myeloid leukemia (AML) in a separate category from chronic myelogenous leukemia (CML) and other myeloproliferative neoplasms. Furthermore, CML is often characterized as containing the BCR-Abl translocation which is absent in AML. Preferred treatments for leukemias, such as myeloid malignancies, would target leukemic cells without unduly affecting hematopoietic stem cell populations.

Thioridazine is a dopamine receptor antagonist that belongs to the phenothiazine drug group and is used as an anti-psychotic. It has been in clinical use since 1959, however because of concerns about cardiotoxicity and retinopathy at high doses this drug is not commonly prescribed, and is reserved for patients who have failed to respond to, or have contraindications for more widely used antipsychotics. Schizophrenic patients receiving dopamine receptor antagonist medication at doses deemed effective for schizophrenia have been reported to have a reduced incidence of rectum, colon, and prostate cancer compared to the general population.

There is a need for novel methods for the treatment and prognosis of cancers and in particular for novel methods for the treatment and prognosis of acute myeloid leukemia. There is also a need for novel methods for the identification and validation of agents that target cancer stem cells.

SUMMARY OF THE DISCLOSURE

The discovery of drugs targeting CSC can be approached through several methodologies. The molecular machinery that distinguishes a CSC from a normal stem cell is not well elucidated. There are markers which may be associated with CSCs but there are a paucity of such markers, and they may not necessarily be targets for drug discovery. Moreover, the selection of compounds which target stem cells and potentially can either exhaust the pool of stem cells through inducing differentiation or reduce their numbers through a variety of mechanisms, needs to be selective in order to avoid the same effects on normal stem cells, resulting in undue treatment toxicity. Therefore there is a need for a methodology to discover drugs which have different effects on CSCs compared to other cells.

A method is provided herein which can be used to identify compounds that exhibit a different level of biological activity, or have a selectivity for CSCs compared to other types of cells such as normal stem cells. The method utilizes a reproducible cell line, which acts as a surrogate, having features associated with neoplastic progression, thereby enabling the high throughput testing of thousands of compounds for anti-cancer stem cell activity and referred to herein as transformed neoplastic stem cells. A cell line suitable for this testing is provided in PCT/CA2010/001340. The method provided herein provides a multi-factorial approach to the process of comparing the effect of a compound on one or more CSCs with more than one predetermined value or result. Such results can be determined by measuring cell death, loss of pluripotency, morphology, cell count, and response to cell stress, among others. Further, the instant method provides for the calculation of a Selective Activity Potency Ratio (SAPR), defined as the ratio of the EC50 for a Normal Cell vs. the EC50 of the surrogate cell line, which enables the skilled person to select target compounds with a higher level of precision than was previously enabled. Utilizing a series of dose range comparisons is preferred since, at any single dose, the difference between the compounds effect on each class of cells may not be apparent. In one embodiment, the method further comprises comparing the effect of a compound on one or more CSCs such as variant neoplastic stem cells to an effect of the compound on one or more normal stem cells. In one embodiment, the effect of the compound on one or more normal stem cells is experimentally determined by contacting one or more stem cells with the compound and detecting an effect of the compound on the one or more SCs, wherein the effect is indicative of the biological activity of the compound.

The inventors have determined that thioridazine is cytotoxic to cancer stem cells and in particular those which give rise to acute myeloid leukemia (AML). Furthermore, at concentrations toxic to cancer stem cells, thioridazine has been found to have a relatively limited effect on normal stem cells such as hematopoietic stem cells. The instant method explores a multifactorial process for quantifying the ability of thioridazine-like compounds, characterized as those having a structure similar to thioridazine and exhibiting a Tanimoto coefficient >0.6, to have CSC effects.

Utilizing the instantly disclosed methodology, it was surprisingly discovered that of 167 known or currently used cancer therapies only 5% exhibited anti-CSC effects. Thus, the present invention fulfills a long felt need in the art to provide a method for elucidating compounds which have never been used to treat patients clinically in cancer, as having potent anti-CSC effects when even clinical cancer compounds have such a low probability of having anti-CSC effects.

Accordingly, in one aspect of the disclosure there is provided a method for identifying and validating a test agent as a selective anti-cancer stem cell agent. In one embodiment, the method comprises:

contacting one or more variant neoplastic stem cells with the test agent and one or more normal stem cells with the test agent;

detecting a change in cell count of the variant neoplastic stem cells in response to the test agent, and detecting a change in cell count of the normal stem cells in response to the test agent; and identifying the test agent as a selective anti-cancer stem cell agent if contact with the test agent induces a decrease in cell count of the variant neoplastic stem cells without inducing a comparable decrease in the normal stem cells.

In one embodiment, the method comprises detecting a change in cell count in response to the test agent at a number of different test concentrations. Accordingly, in one embodiment, the method includes contacting the variant neoplastic stem cells and the normal stem cells with the test agent at a plurality of test concentrations and detecting a change in cell count for the one or more variant neoplastic stem cells and for the normal stem cells at the plurality of test concentrations.

In a related aspect of the disclosure, there is provided a two-stage method for identifying and validating an agent as a selective anti-cancer stem cell agent. In a first stage, agents identified as causing a loss of pluripotency and causing a reduction in cell count are identified as test agents for further analysis in a second stage. In one embodiment, the method comprises a first stage of detecting a change in pluripotency and a change in cell count of variant neoplastic stem cells in response to contact with the agent and selecting an agent as a test agent if the agent induces a loss of pluripotency and/or a decrease in cell count of the variant neoplastic stem cells. In one embodiment, the method comprises a second stage of contacting one or more variant neoplastic stem cells with the test agent and contacting one or more normal stem cells with the test agent, detecting a change in cell count of the variant neoplastic stem cells in response to the test agent, detecting a change in cell count of the normal stem cells in response to the test agent and identifying the test agent as a selective anti-cancer stem cell agent if the test agent induces a decrease in cell count of the variant neoplastic stem cells without inducing a comparable decrease in the normal stem cells.

The methods described herein optionally involve contacting the variant neoplastic stem cells and/or the normal stem cells with the test agent at a plurality of test concentrations.

In one embodiment, the plurality of test concentrations varies by at least about 3, 4, or 5 orders of magnitude, or greater than 5 orders of magnitude. In one embodiment, the plurality of concentrations varies at least from about 0.01 µM to 2 µM, or at least from about 10 nM to about 20 µM. Optionally, the plurality of test concentrations can be a dilution series, such as an 8-point, or 10-point dilution series.

In one embodiment, the methods described herein involve comparing a dose-response curve for the change in cell count of the variant neoplastic stem cells in response to contact with the test agent at the plurality of test concentrations, to a dose-response curve for the change in cell count of the normal stem cells in response to contact with the test agent at the plurality of test concentrations. A skilled person will appreciate that a number of different methods can be used to compare dose-response curves. For example, in one embodiment a half maximal effective concentration (EC50) value of a test agent for a decrease in cell count for the variant neoplastic stem cells is determined, and an EC50 value for a decrease in cell count in the normal stem cells is determined.

In one embodiment, EC50 values or similar metrics can be compared to provide a selective-activity ratio for the test agent. For example, in one embodiment the methods include determining a ratio of the EC50 value for decrease in cell count for the normal stem cells relative to the EC50 value for decrease in cell count for the variant neoplastic stem cells. Optionally, the methods described herein further include identifying a test agent as a selective anti-cancer stem cell agent if the ratio of the EC50 values is greater than 1, 2, 3, 4, 5, or greater than 5.

In one aspect of the disclosure, the variant neoplastic stem cells and/or normal stem cells are seeded in a receptacle prior to contacting the cells with an agent or test agent. In one embodiment, the variant neoplastic stem cells are seeded in a first receptacle at about 3000 to 7000 cells per receptacle and the normal stem cells are seeded in a second receptacle at about 8000 to 12000 cells per receptacle. In one embodiment, the variant neoplastic stem cells are seeded at about 4000 to 6000 cells per receptacle, optionally about 5000 cells per receptacle. In one embodiment, the normal stem cells are seeded at about 9000 to 11000 cells per receptacle, optionally about 10000 cells per receptacle.

Optionally, the first receptacle and/or second receptacle are wells on the same microtiter plate or wells on separate microtiter plates. In one embodiment, the microtiter plate is a 96-well microtiter plate, optionally a 96-well coated microtiter plate such as a Matrigel™ plate.

In one embodiment, the change in cell count for the variant neoplastic stem cells is detected between about 48 hours and 96 hours after contacting the cells with the test agent, optionally about 72 hours. In one embodiment, the change in cell count for the normal stem cells is detected between about 4 days and 6 days after contacting the cells with the test agent, optionally about 5 days.

In one embodiment of the methods described herein, the variant neoplastic stem cells are transformed-human Pluripotent Stem Cells (t-hPSCs), optionally v1H9-Oct4-GFP cells or transformed induced Pluripotent Stem Cells, (t-iPSCs). In one embodiment, the variant neoplastic stem cells are human variant neoplastic stem cells.

In one aspect of the present disclosure, a change in cell count is determined for the neoplastic stem cells and/or normal stem cells. In one embodiment, the change in cell count is determined by deoxyribonucleic acid (DNA) content analysis, detection of a nuclear marker such as histones or nuclear laminin, nuclear condensation and/or nuclear detection such as by staining with DNA-binding fluorochromes such as Hoescht, 4',6-diamidino-2-phenylindole (DAPI), Acridine orange, DRAQ5 or safarin. A skilled person will appreciate that detecting a change in cell count may include identifying and/or quantifying individual cells. Optionally, the change in cell count is detected using high content analysis and/or nuclear image analysis.

In one embodiment, the methods described herein include screening a test agent identified as a selective anti-cancer stem cell agent for activity on a cancer cell line, such as a cell line derived from a subject with cancer. In one embodiment, the cancer cell line is a leukemic cell line, such as an acute myeloid leukemia (AML) cell line. In one embodiment, activity is cytotoxicity, induction of apoptosis, loss of pluripotency or induction of differentiation. In one embodiment, the activity is the presence/absence or level or one or more biomarkers.

In one embodiment, the methods described herein include screening a test agent identified as a selective anti-cancer stem cell agent for inducing the expression of one or more stress response genes. In one embodiment, the stress response genes are one or more apoptotic biomarkers such as Annexin V, p53 and/or p21.

In another aspect of the disclosure, one or more agents are screened to identify one or more test agents that induce loss of pluripotency and a decrease in cell count of variant neoplastic stem cells. These test agents may then be identified and validated as selective anti-cancer stem cell agents using the methods described herein, such as by comparing changes in cell count in response to the test agent on variant neoplastic stem cells and normal stem cells.

In one embodiment, the method includes contacting the variant neoplastic stem cells with the agent, detecting a change in pluripotency and a change in cell count of the variant neoplastic stem cells in response to the agent and selecting an agent as the test agent if the agent induces a loss of pluripotency and a decrease in cell count of the variant neoplastic stem cells. In one embodiment, the variant neoplastic stem cells are contacted with the agent at about 10 µM. In one embodiment, a plurality of agents are screened on a microtiter plate and identified as test agents based on a threshold standard deviation from the mean or other suitable statistic. For example, in one embodiment the threshold is a Z score of at least 3 standard deviations from the mean, optionally from the plate-wide mean for change in pluripotency and change in cell count. In one embodiment, variant neoplastic stem cells are treated with BMP4 to induce loss of pluripotency as a positive control, optionally at least 100 ng/mL BMP4.

A skilled person will appreciate that a number of different methods known in the art may be used to detect a change in pluripotency of the variant neoplastic stem cells is detected by detecting a change in the expression level of one or more pluripotency markers. One embodiment includes detecting the expression of one or more pluripotency markers using antibodies selective for the one or more pluripotency markers. In one embodiment, the expression of one or more pluripotency markers in the variant neoplastic stem cells or normal stem cells is operably linked to a reporter gene, such as GFP. In one embodiment, the pluripotency marker is selected from Oct4 and Sox2. In one embodiment, the pluripotency marker is selected from Oct4, Sox2, Nanog, SSEA3, SSEA4, TRA-1-60, TRA-1-81, IGF1 receptor, connexin 43, E-cadherin, Alkaline phosphatase, REX1, CRIPTO, CD24, CD90, CD29, CD9 and CD49f, and mixtures thereof.

In one aspect, the present disclosure provides a method for identifying and validating a test agent as a selective anti-cancer stem cell agent comprising:

contacting one or more variant neoplastic stem cells with the test agent and one or more normal stem cells with the test agent;

detecting a change in one or more activities of the variant neoplastic stem cells in response to the test agent, detecting a change in one or more activities of the normal stem cells in response to the test agent; and identifying the test agent as a selective anti-cancer stem cell agent if contact with the test agent induces one or more activities in the variant neoplastic stem cells without inducing a comparable activity in the normal stem cells.

In one embodiment, the activity is apoptosis, necrosis, proliferation, cell division, differentiation, migration or movement, presence or absence of one or more biomarkers, level of one or more biomarkers, or induction thereof.

In another aspect, there is provided a two-stage method for identifying and validating an agent as a selective anti-cancer stem cell agent comprising:

detecting a change in one or more activities of variant neoplastic stem cells in response to contact with the agent and selecting an agent as a test agent if the agent induces one or more activities in the variant neoplastic stem cells; and contacting one or more variant neoplastic stem cells with the test agent and contacting one or more normal stem cells with the test agent, detecting a change one or more activities of the variant neoplastic stem cells in response to the test agent, detecting a change one or more activities of the normal stem cells in response to the test agent and identifying the test agent as a selective anti-cancer stem cell agent if the test agent induces one or more activities in the variant neoplastic stem cells without inducing a comparable activity in the normal stem cells.

In one embodiment, the activity is apoptosis, necrosis, proliferation, cell division, differentiation, migration or movement, presence or absence of one or more biomarkers, level of one or more biomarkers, or induction thereof.

In another aspect of the disclosure, it has surprisingly been determined that compounds structurally similar to thioridazine are effective at inducing the differentiation of cancer stem cells or killing cancer stem cells. Also provided are methods of treating cancer in a subject comprising administering to the subject a compound that is structurally similar to thioridazine.

In one embodiment, the compounds have a Tanimoto coefficient of similarity to thioridazine of at least 0.6. In one embodiment, the compounds have a Tanimoto coefficient of similarity to thioridazine of at least 0.7, 0.8, 0.9 or 0.95. Optionally, the compounds include, but are not limited to thioridazine, prochlorperazine, trifluoperazine, fluphenazine, perphenazine, and triflupromazine. In one embodiment the compounds are phenothiazine derivatives. In one embodiment, the compound preferentially induces the differentiation of cancer stem cells relative to normal stem cells. For example, in one embodiment the compounds preferentially induce the differentiation of variant neoplastic stem cells relative to normal stem cells such as H9 cells.

The cancer stem cells may be found in vivo, in vitro or ex vivo. In one embodiment, the cancer stem cells are found in vivo in a subject with cancer. In one embodiment the cancer is leukemia, such as acute myeloid leukemia. In one embodiment, the cancer is breast cancer. In one embodiment, the cancer is lung cancer, colon cancer, brain cancer or prostate cancer.

In another aspect of the disclosure, there is provided method of treating cancer in a subject comprising administering to the subject a compound with a Tanimoto coefficient of similarity to thioridazine of at least 0.6. Also provided are uses of compounds with a Tanimoto coefficient of similarity to thioridazine of at least 0.6 for the treatment of cancer. In one embodiment, the compounds have a Tanimoto coefficient of similarity to thioridazine of at least 0.7, 0.8, 0.9 or 0.95. Optionally, the compounds include, but are not limited to, thioridazine, prochlorperazine, trifluoperazine, fluphenazine, perphenazine, and triflupromazine. In one embodiment the compounds are phenothiazine derivatives. In one embodiment, the compound preferentially differentiates cancer stem cells relative to normal stem cells. In one embodiment, the cancer is acute myeloid leukemia.

In a related aspect of the disclosure, it has surprisingly been determined that dopamine receptor antagonists such as thioridazine or chlorpromazine are cytotoxic to cancer cells and in particular acute myeloid leukemia (AML). Furthermore, dopamine receptors antagonists at concentrations toxic to cancer cells have been found to have a relatively limited effect on normal stem cells such as hematopoietic stem cells. It has also been determined that dopamine receptors are expressed in AML cell lines and in primary AML cells, but show relatively less expression in cell lines enriched for normal hematopoietic stem cells. In addition, the expression of dopamine receptors in AML cells is shown to correlate with that of the monoblastic marker CD14. Dopamine receptor antagonists such as thioridazine are cytotoxic to AML cells that express CD14.

Accordingly, in one aspect there is provided a method of treating a cancer or precancerous disorder in a subject comprising administering to the subject in need thereof a dopamine receptor (DR) antagonist. In a similar aspect, the present disclosure describes the use of a dopamine receptor antagonist for the treatment of cancer or a precancerous disorder. In one embodiment, the cancer or precancerous disorder is a myeloproliferative disease or leukemia. In one embodiment, the cancer is acute myeloid leukemia (AML). In one embodiment, the DR antagonist preferentially induces the differentiation of cancer stem cells relative to hematopoietic or normal stem cells.

In one embodiment, the dopamine receptor antagonist is a phenothiazine derivative such as thioridazine or chlorpromazine. Optionally the dopamine receptor antagonist is a multi-receptor antagonist that antagonizes more than one dopamine receptor. In one embodiment, the dopamine receptor antagonist is a $D_2$ family dopamine receptor antagonist. In one embodiment, the DR antagonist is a compound selected from those listed in Table 1.

In another aspect there is provided a method for reducing the proliferation of a cancer cell comprising contacting the cancer cell with a dopamine receptor antagonist. In a similar aspect there is provided the use of a dopamine receptor antagonist for reducing the proliferation of a cancer cell. In one embodiment, contacting the cell with a dopamine receptor antagonist induces cell death or differentiation of a cancer cell or precancerous cell. In one embodiment, the cancer cell is a cancer stem cell and contacting the cancer stem cell with a dopamine receptor antagonist induces differentiation of the cancer stem cell. The cell may be in vivo or in vitro. In one embodiment, the precancerous cell is a myeloproliferative cell. Optionally, the cancer cell is a leukemic cell, such as an acute myeloid leukemia (AML) cell or a monocytic leukemic cell. In one embodiment, the cell is CD14 positive. In one embodiment, the dopamine receptor antagonist is a phenothiazine derivative such as thioridazine. In one embodiment, the dopamine antagonist is a compound selected from those listed in Table 1.

In another aspect there is provided a method of identifying a subject with cancer suitable for treatment with a dopamine receptor antagonist. In one embodiment, the method includes determining the expression of one or more dopamine receptors in a sample of cancer cells from the subject. In one embodiment, subjects with cancer cells that express one or more dopamine receptors are identified as suitable for treatment with dopamine receptor antagonists. In one embodiment, the cancer is leukemia and the cancer cells are leukemic cells. In one embodiment, the leukemia is acute myeloid leukemia or monocytic leukemia. In one embodiment, the cancer is breast cancer. In one embodiment, the method of identifying a subject with cancer comprises testing the sample for the expression of CD14.

In one aspect, there is provided a method for determining a prognosis for a subject with cancer, comprising determining the expression level of one or more dopamine receptor biomarkers in a sample from the subject and comparing the level of expression of the one or more biomarkers to a control. Optionally, the method provided herein include providing or obtaining a sample of cancer cells from the subject. In one embodiment, increased expression of one or more biomarkers compared to the control indicates a more severe form of cancer. In one embodiment, the dopamine receptor biomarkers are DR3 and/or DR5. In one embodiment, the cancer is leukemia or breast cancer and the sample comprises leukemic cells or breast cancer cells. In one embodiment, the leukemia is acute myeloid leukemia or monocytic leukemia.

Also provided are methods for identifying a subject with leukemia. In one embodiment, the methods include determining the expression level of one or more dopamine receptors in a sample from the subject and comparing the level of expression of the one or more dopamine receptors to a control. Optionally, sample comprises white blood cells and/or the method further comprises providing a sample comprising white blood cells from the subject. In one embodiment, increased expression levels of one or more dopamine receptors compared to a control is indicative of a subject with leukemia, such as acute myeloid leukemia, or monocytic leukemia. In one embodiment, the method further comprises testing for CD14.

Also provided are methods for screening compounds for anti-cancer activity comprising identifying compounds that are dopamine receptor antagonists. In one embodiment, the anti-cancer activity is reduced proliferation of AML cells or monocytic cells. Optionally, the methods include identifying compounds that preferentially induce the differentiation of cancer stem cells relative to hematopoietic or normal stem cells.

In one aspect, there is provided methods for identifying a cancer stem cell from a population of cells. In one embodiment, the method comprises determining whether a cell expresses one or more biomarkers selected from dopamine receptor (DR) 1, DR2, DR3, DR4 and DR5. In one embodiment, the expression of dopamine receptor (DR) 1, DR2, DR3, DR4 and/or DR5 is indicative that the cell is a cancer stem cell.

In one embodiment, the population of cells comprises cells isolated from a mammal or cells in culture such as cell culture. In one embodiment, the population of cells comprises pluripotent stem cells. In one embodiment, the population of cells comprises cancer cells such as hematological cancer cells or pre-cancerous cells. Optionally, the method includes testing the cell for the expression of polynucleotides or polypeptides that code for DR1, DR2, DR3, DR4 or DR5. In one embodiment, a cell that expresses DR1, DR2, DR3, DR4 and DR5 is identified as a cancer stem cell. In some embodiments, the methods described herein also include isolating cancer stem cells from a population of cells. For example, cells that are identified as cancer stem cells can be isolated from a population of cells or other material using methods known in the art such as flow cytometry, fluorescence activated cell sorting, panning, affinity column separation, or magnetic selection. In one embodiment, cancer stem cells are isolated using antibodies to one or more of DR1, DR2, DR3, DR4 and DR5.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

One or more embodiments of the disclosure will now be described in relation to the drawings in which.

DETAILED DESCRIPTION

I. Definitions

Figure 1:
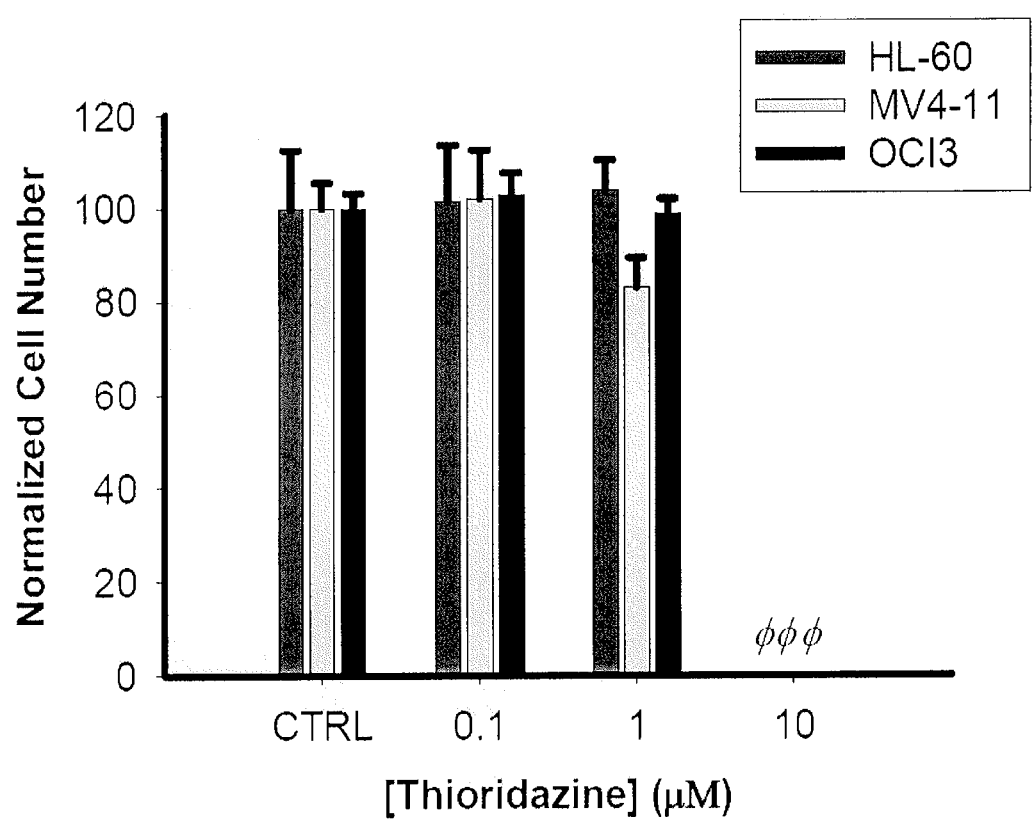
FIG. 1 shows thioridazine at 10 µM is cytotoxic to leukemic cell lines HL-60, MV4-11 and OCI3.

As used herein, the term "cancer" refers to one of a group of diseases caused by the uncontrolled, abnormal growth of cells that can spread to adjoining tissues or other parts of the body. Cancer cells can form a solid tumor, in which the cancer cells are massed together, or exist as dispersed cells, as in leukemia.

The term "cancer cell" as used herein refers a cell characterized by uncontrolled, abnormal growth and the ability to invade another tissue or a cell derived from such a cell. Cancer cell includes, for example, a primary cancer cell obtained from a patient with cancer or cell line derived from such a cell. Similarly, a "hematological cancer cell" refers to a cancer cell deriving from a blood cell or bone marrow cell. Examples of cancer cells include, but are not limited to, cancer stem cells, breast cancer cells, rectum cancer cells, colon cancer cells, prostate cancer cells and hematological cancer cells such as myelomas, leukemic cells or lymphoma cells.

As used herein the term "cancer stem cell" refers to a cell that is capable of self-renewal and differentiating into the lineages of cancer cells that comprise a solid tumor and/or hematological malignancy. Cancer stem cells are uniquely able to initiate and sustain the disease. Variant neoplastic stem cells are pluripotent cells which exhibit the properties of cancer stem cells and are useful in the screening methods described herein for identifying and/or validating anti-cancer stem cell agents.

As used herein, the term "variant neoplastic stem cell" refers to a cell which is able to differentiate into more than one cell type and does not require Oct4 for self-renewal or survival. Variant neoplastic stem cells are readily distinguished from normal stem cells. For example, some variant neoplastic stem cells co-express FGFR1 and IGFR1. In contrast, normal human embryonic stem cells (hESs) express IGF1R, while FGFR1 is expressed exclusively in fibroblast-like cells also found in human embryonic stem cell cultures. Some variant neoplastic stem cells do not require basic fibroblast growth factor (bFGF) in culture for maintenance of an undifferentiated state. As used herein an "undifferentiated state" refers to a cell that is pluripotent or is still able to differentiate into more than one cell type. Some variant neoplastic stem cells maintain the expression of SSEA3 in the absence of bFGF, and/or require Nanog for self-renewal and cell survival.

In one aspect of the disclosure, the variant neoplastic stem cells described herein can be passaged as a single cell. As used herein, "passaged as single cells" refers to individually isolating and transferring a single cell to a culture vessel wherein the cell is then capable of forming a plurality of cells. Optionally, variant neoplastic stem cells include one or more vectors or reporter constructs such as a vector wherein the expression of one or more pluripotency genes is operably linked to a reporter gene. In one embodiment, the variant neoplastic stem cells have neoplastic features and display lower differentiation potential in vitro. In one embodiment, the variant neoplastic stem cells are niche independent and have increased tumor-initiating activity. In particular, in one embodiment variant neoplastic stem cells exhibit significantly reduced neural differentiation and are devoid of hematopoietic potential. As used herein, the term "variant neoplastic stem cells" includes transformed-human Pluripotent Stem Cells (t-hPSCs) or transformed-induced Pluripotent Stem Cells (t-iPSCs) as described in PCT Publication No. WO2011026222, hereby incorporated by reference in its entirety. Variant neoplastic stem cells exhibit similarities in functional properties to somatic cancer stem cells and are therefore useful as a surrogate for somatic cancer stem cells. Variant neoplastic stem cells are also amenable for high content and high throughput screening in vitro. In one embodiment, the variant neoplastic stem cells are induced variant neoplastic stem cells. In one embodiment, the variant neoplastic stem cells are human variant neoplastic stem cells. Optionally, the variant neoplastic stem cells are derived from a somatic source or an embryonic source.

As used herein, a "normal stem cell" is a stem cell that is not a cancer stem cell or a variant neoplastic stem cell. Optionally, a "normal stem cell" is a stem that does not exhibit the features of a cancer cell, like a variant neoplastic stem cell. Examples of "normal" stem cells include pluripotent stem cells, embryonic stem cells such as H9 stem cells and hematopoietic stem cells, somatic stem cells. Optionally, the normal stem cells are human stem cells. Optionally, the normal stem cells are derived from a somatic source or an embryonic source.

The term "precancerous disorder" as used herein refers to one of a group of hyperproliferative disorders that can develop into cancer, including for example precancerous blood disorders, such as myeloproliferative disease or myelodysplastic syndrome which is a premalignant condition that is related to and/or can develop into acute myeloid leukemia (AML).

The term "precancerous cell" as used herein refers to a cell characterized by uncontrolled, abnormal growth or a cell derived from such a cell. The term "precancerous cell" includes, for example, a primary precancerous cell obtained from a patient with precancerous disorder or cell line derived from such a cell or a cancer stem cell. Similarly, a "hematological precancerous cell" refers to a precancerous cell deriving from a blood cell or bone marrow cell. In one embodiment, the hematological precancerous cell is a myeloproliferative cell.

The term "leukemia" as used herein refers to any disease involving the progressive proliferation of abnormal leukocytes found in hemopoietic tissues, other organs and usually in the blood in increased numbers. "Leukemic cells" refers to leukocytes characterized by an increased abnormal proliferation of cells. Leukemic cells may be obtained from a subject diagnosed with leukemia.

The term "acute myeloid leukemia" or "acute myelogenous leukemia" ("AML") refers to a cancer of the myeloid line of blood cells, characterized by the rapid growth of abnormal white blood cells that accumulate in the bone marrow and interfere with the production of normal blood cells. Pre-leukemic conditions such as myelodysplastic or myeloproliferative syndromes may also develop into AML.

As used herein, the term "monocytic leukemia" refers to a subtype of leukemia characterized by the expression of CD14, and includes Acute Monocytic Leukemia, which is a subtype of acute myeloid leukemia. In one embodiment, a subject is identified as having acute monocytic leukemia if they have greater than 20% blasts in the bone marrow, and of these, greater than 80% are of the monocytic lineage.

The term "dopamine receptor antagonist" refers to a compound that produces any detectable or measurable reduction in the function or activity of one or more dopamine receptors. In one embodiment, the dopamine receptors (DR) are selected from DR1, DR2, DR3, DR4 and DR5. Dopamine receptor antagonists may be selective for one or multiple dopamine receptors, i.e. a "multi-receptor antagonist". Examples of multi-receptor dopamine antagonists include thioridazine and chlorpromazine. Dopamine receptors are commonly grouped in $D_1$-family dopamine receptors (DR1 and DR5) and $D_2$-family dopamine receptors (DR2, DR3 and DR4). In one embodiment, the dopamine receptor antagonist is a compound selected from those listed in Table 1.

TABLE 1

Dopamine antagonists suitable for use in the methods described herein.

| Dopamine Receptor Antagonist | Mechanism of Action |
| --- | --- |
| Acetopromazine maleate salt | Dopaminergic antagonist |
| Amisulpride | D2 and D3 receptor antagonist |
| Amoxapine | Dopamine-reuptake inhibitor |
| Azaperone | Dopaminergic receptor antagonist |
| Benperidol | Dopamine antagonist |
| Benzo[a]phenanthridine-10,11-diol, 5,6,6a,7,8,12b-hexahydro-, trans- [CAS] | D1 ligand |
| Bromopride | Dopamine antagonist |
| Bromperidol | Dopamine antagonist |
| Chlorpromazine hydrochloride | D2 antagonist, selective D1, D3, D4 & D5 |
| Chlorprothixene hydrochloride | D2 dopamine receptor antagonist |
| Clomipramine hydrochloride | chlorpromazine derivative |
| Disulfiram | Dopamine beta-hydroxylase inhibitor |
| DO 897/99 | D3 antagonist |
| Domperidone | Dopamine Antagonists |
| DROPERIDOL | D2 (dopamine receptor) antagonist |
| Ethopropazine hydrochloride | Thioridazine derivative |
| Fluperlapine | D2 (dopamine receptor) antagonist |
| Fluphenazine dihydrochloride | Dopamine antagonist D1&D2 antagonist |
| GBR 12909 dihydrochloride | Dopamine reuptake inhibitor |
| Haloperidol | Dopamine antagonist D2, non-selective antagonist |
| Hydrastinine hydrochloride | Dopamine receptor blocker |
| Indatraline | potent D antagonist |
| Itopride | Dopamine D2 receptors and ACE inhibition |
| LEVOSULPIRIDE | D2, D3, & D4 antagonist |
| Loxapine succinate | Dopamine antagonist/D2, D4 |
| Mesoridazine | D2 antagonist |
| Mesoridazine besylate | D antagonist |
| Methotrimeprazine maleat salt | Thioridazine derivative |
| Metixene hydrochloride | Thioridazine derivative |
| Molindone hydrochloride | Dopamine receptor antagonist |
| Nafadotride | D3 antagonist |
| Nomifensine maleate | Dopamine uptake inhibitor |
| OLANZAPINE | D1&D2 antagonist |
| PEROSPIRONE HCl | D2&D4 antagonist |
| Perphenazine | D1 & D2 antagonist |
| PHENOTHIAZINE | Thioridazine derivative |
| Pimozide | Dopamine antagonist |
| Piperacetazine | Thioridazine derivative |
| Prochlorperazine | Thioridazine derivative |
| Prochlorperazine dimaleate | Dopamine antagonist |
| Promazine hydrochloride | Dopamine receptor antagonist |
| Promethazine hydrochloride | Thioridazine derivative |
| Quetiapine | dopamine and serotonin receptors antagonist |
| QUETIAPINE HEMIFUMARATE | D2 antagonist |
| R(+)-SCH-23390 hydrochloride | D1 antagonist |
| Raclopride | D2 antagonist |
| Remoxipride Hydrochloride | Dopaminergic antagonist |
| RISPERIDONE | D1 & D2 antagonist |
| S(−)Eticlopride hydrochloride | Dopamine receptor antagonist |
| Sertindole | Dopamine D2/Serotonin 5-HT2 receptor antagonist |
| SKF 83566 | D1 antagonist |
| Spiperone | D2 antagonist |
| Sulpiride | D2 antagonist |
| Sulpiride | D2 & D3 antagonist |
| Thiethylperazine malate | Thioridazine derivative |
| Thioproperazine dimesylate | D1 & D2 antagonist |
| Thioridazine hydrochloride | Thioridazine derivative |
| TRIFLUOPERAZINE | D2 antagonist |
| Triflupromazine hydrochloride | D1 & D2 antagonist |
| Trimeprazine tartrate | Thioridazine derivative |
| Trimethobenzamide hydrochloride | D2 antagonist |
| Ziprasidone Hydrochloride | Dopamine D2/serotonin 5-HT2 antagonist |
| Zotepine | Dopamine D2/serotonin 5-HT2 antagonist |

As used herein, the term "phenothiazine" or "phenothiazine derivative" refers to a compound that is derived from or contains a phenothiazine moiety or backbone. Phenothiazine has the formula $S(C_6H_4)_2NH$ and phenothiazine derivatives comprise one or more substitutions or additions to phenothiazine. For example, some phenothiazine derivatives have a three-ring structure in which two benzene rings are linked by a nitrogen and a sulfur. Examples of phenothiazine derivatives include thioridazine, chlorpromazine, levomepromazine, mesoridazine, fluphenazine, perphenazine, prochlorperazine, and trifluoperazine. Additional examples of phenothiazine derivatives for use in the methods of the present disclosure are set out in Table 1. In one embodiment, thioridazine has the IUPAC name 10-{2-[(RS)-1-Methylpiperidin-2-yl]ethyl}-2-methylsulfanylphenothiazine. Optionally, one or more racemic forms of a phenothiazine derivative such as thioridazine are used in the methods described herein.

As used herein, "reducing the proliferation of a cancer cell" refers to a reduction in the number of cells that arise from a cancer cell as a result of cell growth or cell division and includes cell death or differentiation of a cancer stem cell. The term "cell death" as used herein includes all forms of cell death including necrosis and apoptosis. As used herein "differentiation of a cancer stem cell" refers to the process by which a cancer stem cell loses the capacity to self-renew and cause the lineages of cancer cells that comprise a tumor or hematological malignancy. As used herein, "killing a cancer stem cell" includes all forms of cell death including necrosis and apoptosis.

The term "determining a prognosis" refers to a prediction of the likely progress and/or outcome of an illness, which optionally includes defined outcomes (such as recovery, symptoms, characteristics, duration, recurrence, complications, deaths, and/or survival rates).

As used herein the term "control" refers to a comparative sample or a pre-determined value. In one embodiment, "control" refers to a level of expression of a biomarker as described herein. In one embodiment, the control is representative of normal, disease-free cell, tissue, or blood. In one embodiment, the control is representative of subjects with cancer for whom the clinical outcome or severity of the disease is known. For example, in one embodiment the "control" is representative of subjects who have survived for at least 5 years after a diagnosis with AML. In one embodiment, the "control" is representative of subjects with cancer who have a particular stage of grade of the disease. In one embodiment, the "control" is representative of stem cells that are not cancer stem cells.

As used herein, the phrase "effective amount" or "therapeutically effective amount" means an amount effective, at dosages and for periods of time necessary to achieve the desired result. For example in the context or treating a cancer such as AML, an effective amount is an amount that for example induces remission, reduces tumor burden, and/or prevents tumor spread or growth of leukemic cells compared to the response obtained without administration of the compound. Effective amounts may vary according to factors such as the disease state, age, sex and weight of the animal. The amount of a given compound that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art.

The term "pharmaceutically acceptable" means compatible with the treatment of animals, in particular, humans.

The term "subject" as used herein includes all members of the animal kingdom including mammals, and suitably refers to humans. Optionally, the term "subject" includes mammals that have been diagnosed with cancer or are in remission.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease (e.g. maintaining a patient in remission), preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. In one embodiment, treatment methods comprise administering to a subject a therapeutically effective amount of a dopamine receptor antagonist as described herein and optionally consists of a single administration, or alternatively comprises a series of administrations.

II. Methods and Uses

It has surprisingly been found that dopamine receptor (DR) antagonists are cytotoxic to AML lines and primary AMLs while being much less toxic to normal hematopoietic stem cells. As shown in Examples 2 and 10, the DR antagonist thioridazine significantly reduced leukemic stem cell (LSC) function while preserving normal hematopoietic stem cell capacity.

Accordingly, in one embodiment there is provided a method of treating a cancer or precancerous disorder in a subject comprising administering to the subject in need thereof a dopamine receptor antagonist. Also provided is a use of a dopamine receptor antagonist for the treatment of cancer or a precancerous disorder. In one embodiment, the methods or uses described herein are useful to treat a precancerous disorder, such as a myeloproliferative disease. In one embodiment, the cancer is leukemia such as acute myeloid leukemia (AML), or monocytic leukemia. The methods and uses described herein are particularly useful for the treatment of cancer cells that express dopamine receptors. In one embodiment, the methods and uses described herein are useful for the treatment of cancer cells that express the monocytic marker CD14. In one embodiment, the dopamine receptor antagonist preferentially induces the differentiation of cancer stem cells in the subject relative to hematopoietic or normal stem cells. In one embodiment, the cancer stem cells are leukemic cancer stem cells. In one embodiment, the subject has AML and the cancer stem cells are AML cancer stem cells.

In one embodiment, the dopamine receptor antagonists are antagonists for one or more of dopamine receptors (DR) such as DR1, DR2, DR3, DR4, and DR5. Optionally the DR antagonist is a multi-receptor antagonist, or is specific for a single dopamine receptor subtype. In one embodiment, the DR antagonist is a phenothiazine derivative such as thioridazine, or chlorpromazine. In one embodiment, the DR antagonist is selected from the compounds listed in Table 1. A person of skill in the art would readily be able to identify additional dopamine receptor antagonists that are useful for the treatment of cancer as described herein.

In one embodiment, the methods or uses described herein involve a phenothiazine derivative such as thioridazine or chlorpromazine. A person skilled in the art would readily be able to identify additional phenothiazine derivatives that are dopamine receptor antagonists and useful for the treatment of cancer as described herein. In one embodiment, the phenothiazine derivatives have a differential toxicity for cancer cells, such as leukemic cells, compared to normal stem cells or hematopoietic stem cells.

In one embodiment, the dopamine receptor antagonists and/or phenothiazine derivatives are prepared for administration to a subject in need thereof as known in the art. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999.

In one embodiment, there is also provided a method for reducing the proliferation of a cancer cell or cells comprising contacting the cell with a dopamine receptor antagonist. In a similar embodiment there is provided a use of a dopamine receptor antagonist for reducing the proliferation of a cancer cell or cells. In one embodiment, the cancer cell is a cancer stem cell. In one embodiment, the DR antagonist induces differentiation or cell death of a cancer stem cell. In one embodiment, the DR antagonist induces cell death of a cancer cell. Optionally, the cancer cell may be in vivo or in vitro. The cancer cell may be a precancerous cell such as a myelodysplastic or myeloproliferative cell. In one embodiment, the cancer cell is a hematological cancer cell. In one embodiment, the cancer cell is a leukemic cell, such as a cell from a subject with AML. In one embodiment, the DR receptor antagonist is a phenothiazine derivative such as thioridazine or chlorpromazine. In one embodiment, the DR antagonist is selected from the compounds listed in Table 1.

Figure 5:
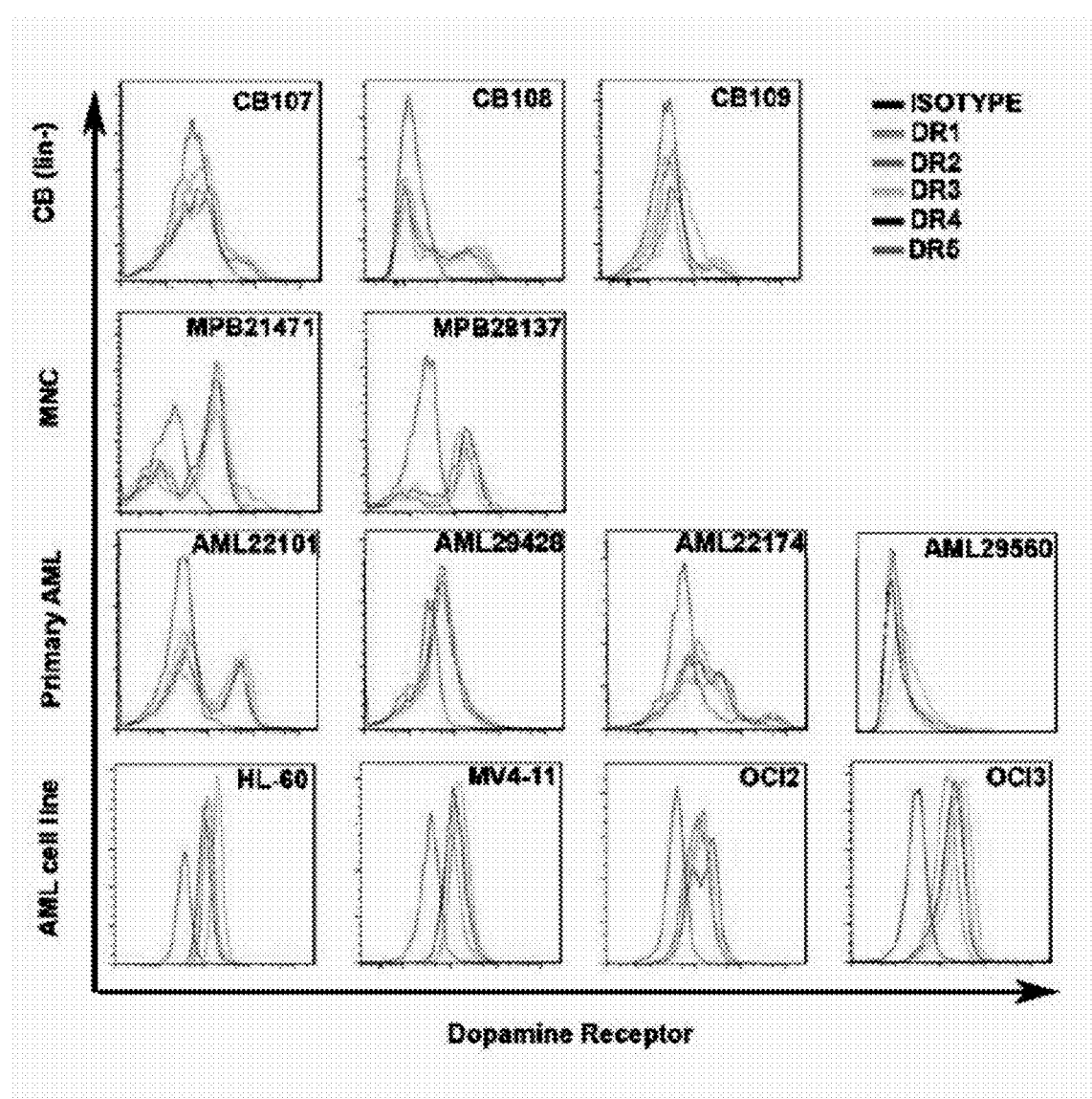
FIG. 5 shows the expression of dopamine receptors DR1, DR2, DR3, DR4 and DR5. DR expression was observed in AML cell lines, some primary AML and mononuclear cells (MNC) but not in HSC enriched cells (CB lin(−)).

As shown in Example 4 and FIG. 5, the Applicants have surprisingly shown that some AML cell lines and primary AML cells exhibit a relative increase in the expression of dopamine receptors compared to normal hematopoietic stem cells. Screening subjects with cancer for the expression of dopamine receptors in cancer cells may therefore serve to identify subjects who would benefit from treatment with dopamine receptor antagonists. Accordingly, in one aspect of the disclosure there is provided a method for identifying a subject with cancer suitable for treatment with dopamine receptor antagonists. In one embodiment, the method comprises determining the expression of one or more dopamine receptors in a sample of cancer cells from a subject. Subjects with cancer cells that express one or more dopamine receptors are thereby identified as suitable for treatment with dopamine receptor antagonists. For example, the expression of one or more dopamine receptors in a sample of cancer cells can be determined by testing the cancer cells for polypeptides or polynucleotides that encode for dopamine receptors as described herein. In one embodiment, the method includes obtaining or providing a sample of cancer cells from the subject and/or testing the sample for the expression of one or more dopamine receptors. In one embodiment, the cancer is leukemia and the cancer cells are leukemic cells. In one embodiment, the cancer is AML. Optionally, the method includes determining additional markers known to be associated with cancer, hematological malignancies, leukemia or AML or markers associated with specific treatment regimes. In one embodiment, cancer cells are also tested for the monocytic marker CD14.

The expression of dopamine receptors has been observed in samples of breast cancer and AML and can serve as a biomarker for the severity of disease. As shown in Example 11 and FIGS. 14g-h, high levels of DR expression correlate with poor prognosis while low levels demonstrate a better prognosis. Accordingly, in one aspect of the disclosure there is provided a method of determining a prognosis for a subject with cancer. In one embodiment, the method comprises determining the expression of one or more biomarkers selected from dopamine receptor (DR) 1, DR2, DR3, DR4, DR5 and CD14 in a sample of cancer cells from the subject and comparing the level of expression of the one or more biomarkers to a control. In one embodiment, an increase in the level of expression of the one or more biomarkers relative to the control indicates that the subject has a more severe form of cancer. Optionally, the methods described herein include providing or obtaining a sample of cancer cells from the subject such as a blood sample containing leukemic cells or a tumour sample. In one embodiment, the cancer cells are leukemic cells or breast cancer cells and increased expression of one or more biomarkers compared to the control indicates a more severe form of leukemia or breast cancer. Optionally, additional biomarkers known to be associated with cancer or severity of disease are also tested and compared to control samples. A skilled person will appreciate selecting a control that is representative of a particular prognosis in subjects with cancer such that observing a difference or similarity in the level of the one or more of the biomarkers described herein between the test sample with the control provides a corresponding prognosis for the test subject. For example, in one embodiment the control represents subjects diagnosed with AML known to have a particular outcome or prognosis and observing an increase in the level of expression of one or more dopamine receptors relative to the control indicates a worse prognosis for the subject relative to the control.

The methods described herein are also useful for identifying subjects with cancer. In one embodiment, the methods described herein are useful for identifying subjects with leukemia, such as AML or monocytic leukemia. Accordingly, in one embodiment, there is provided a method for identifying a subject with leukemia comprising providing a sample from a subject and testing the sample for the expression of one or more biomarkers selected from DR1, DR2, DR3, DR4 and DR5. In one embodiment, the sample comprises cancer cells such as leukemic cells and/or white blood cells. In one embodiment, the method comprises comparing the level of expression of one or more biomarkers to a control. In one embodiment, increased expression of DRs in the sample compared to the control is indicative of cancer. In one embodiment, an increased expression of DRs in the subject compared to the control is indicative of leukemia. In one embodiment, increased expression of DRs in the subject compared to the control is indicative AML or monocytic leukemia. Optionally, the methods described herein may be used in combination with other diagnostic methods for the identification of cancers or leukemia as known to a person of skill in the art.

As shown in Example 11, dopamine receptor expression demarcates human cancer stem cells from other cells such as normal hPSCs that express the pluripotent marker SSEA3. Accordingly, in one embodiment, there is provided a method of identifying a cancer stem cell from a population of cells comprising determining whether a cell expresses one or more biomarkers selected from dopamine receptor (DR) 1, DR2, DR3, DR4 and DR5. In one embodiment, expression of DR1, DR2, DR3, DR4 or DR5 is indicative that the cell is a cancer stem cell. Optionally, expression of 2 or more, 3 or more, 4 or more or all 5 DRs is indicative that the cell is a cancer stem cell. In one embodiment, a cell that expresses DR1, DR2, DR3, DR4 and DR5 is identified as a cancer stem cell.

In one embodiment, the cancer stem cell is identified from a population of cells. In one embodiment the population of cells contains more than one cell type, such as somatic cells, pluripotent stem cells, cancer cells and/or cancer stem cells. In one embodiment, the population of cells is a plurality of cells in cell culture, such as tissue culture. In one embodiment, the population of cells is from a mammal, such as a primary tissue sample or blood sample. In one embodiment, the population of cells is from a mammal with cancer or suspected of having cancer. In one embodiment, the population of cells includes stem cells, somatic stem cells and/or pluripotent stem cells as well as one or more cancer stem cells. In one embodiment, the population of cells includes cancer cells or pre-cancerous cells such as hematological cancer cells. In one embodiment, the population of cells includes monocytic cells. In one embodiment, the population of cells includes breast cancer cells. Optionally, the population of cells is from a tissue sample, such as a tumor sample, that has been dissociated into single cells.

In one aspect of the method, the step of determining whether the cell expresses one or biomarkers comprises testing the cell for the expression of polynucleotides or polypeptides that code for DR1, DR2, DR3, DR4 or DR5. For example, methods known in the art such a RT-PCR or reporter genes that detect the expression of polynucleotides, or immunohistochemical methods that detect expression of polypeptides, can be used for determining the expression of a biomarker such as DR1, DR2, DR3, DR4 or DR5. In one embodiment, the biomarkers are cell surface biomarkers and the method involves detecting DR1, DR2, DR3, DR4 or DR5 expressed on the surface of the cell.

In one embodiment, the methods for identifying a cancer stem cell described herein include determining the level of expression of one or more biomarkers selected from dopamine receptor (DR) 1, DR2, DR3, DR4 and DR5 and then comparing the level of expression to a control level. For example, in one embodiment the control represents cells that are not cancer stem cells, such as somatic stem cells, hematopoietic stem cells or cells that express the pluripotency marker SSEA3, and cells that have an increased level of expression of the biomarkers DR1, DR2, DR3, DR4 and/or DR5 compared to the control are identified as cancer stem cells. Optionally, cells that have an increased amount of expression compared to the control are identified as cancer stem cells (e.g. at least 2×, 5×, or 10× etc.).

In one embodiment, the method can also comprise: (a) providing a population of cells (b) contacting the population with an agent that specifically binds to one or more biomarkers selected from DR1, DR2, DR3, DR4 and DR5; and (c) selecting cells that specifically bind to the agent of (b) thereby identifying and/or isolated cancer stem cells from a population of cells. In one embodiment, the agent is an antibody that selectively binds to a biomarker. In one embodiment, the methods described herein can optionally include two or more selection or isolation steps. The methods described herein can also include a negative step selection, e.g., excluding cells that express one or more markers expressed in cells that are not cancer stem cells, or excluding cells that show reduced levels of expression of a particular marker.

In one embodiment, the present disclosure includes isolating cancer stem cells from a population of cells. For example, in one embodiment, cells that are identified as cancer stem cells are isolated from cells that are not cancer stem cells or from other materials in a sample by selecting for or isolating cells that express one or more biomarkers selected from DR1, DR2, DR3, DR4 and DR5. Optionally, the cancer stem cells are isolated or selected using methods known in the art for sorting cells based on the expression of one or more biomarkers. For example, in one embodiment the step of isolating the cancer stem cells form the population of cells comprises flow cytometry, fluorescence activated cell sorting, panning, affinity column separation, or magnetic selection. In one embodiment, cells that express one or more dopamine receptors are isolated using a binding agent that selectively bind to dopamine receptors that is conjugated to a support such the matric in a separation column or magnetic beads.

In one aspect of the disclosure, the methods described herein include determining the level of one or more biomarkers in a sample from a subject, such as the level of one or more dopamine receptors. In one embodiment, the sample comprises cancer cells or is suspected of comprising cancer cells or pre-cancerous cells. For example, the sample can comprise a blood sample, for example a peripheral blood sample, a fractionated blood sample, a bone marrow sample, a biopsy, a frozen tissue sample, a fresh tissue specimen, a cell sample, and/or a paraffin embedded section. In one embodiment, the subject has or is suspected of having AML and the sample comprises mononuclear cells. In certain embodiments, the sample is processed prior to detecting the biomarker level. For example, a sample may be fractionated (e.g. by centrifugation or using a column for size exclusion or by FACS using a biomarker for monocytes), concentrated or processed, depending on the method of determining the level of biomarker employed.

The level of expression of the biomarkers described herein can be determined by methods commonly known to one of skill in the art. For example, in one embodiment, the level of one or more biomarkers is determined by measuring or detecting the level of a nucleic acid such as mRNA, or the level of a protein or polypeptide. In one embodiment, expression of the one or more biomarkers is determined by detecting the cell surface expression of DR1, DR2, DR3, DR4 and/or DR5. In one embodiment, the methods described herein include detecting a biomarker using immunohistochemistry, such as by using an antibodies specific for the biomarker or another biomarker-specific detection agent. Examples of dopamine receptor antibodies suitable for use in the methods described herein are also listed in Example 7 of the present disclosure.

In one embodiment, the level of an mRNA encoding for a biomarker is determined by quantitative PCR such as RT-PCR, serial analysis of gene expression (SAGE), use of a microarray, digital molecular barcoding technology or Northern blot. A person skilled in the art will appreciate that a number of methods can be used to determine the level of a biomarker, including mass spectrometry approaches, such as multiple reaction monitoring (MRM) and product-ion monitoring (PIM), and also including antibody based methods such as immunoassays such as Western blots and enzyme-linked immunosorbant assay (ELISA). In certain embodiments, the step of determining the expression of a biomarker such as one or more dopamine receptors as described herein, comprises using immunohistochemistry and/or an immunoassay. In certain embodiments, the immunoassay is an ELISA. In yet a further embodiment, the ELISA is a sandwich type ELISA.

The term "level" as used herein refers to an amount (e.g. relative amount or concentration) of biomarker that is detectable or measurable in a sample. For example, the level can be a concentration such as μg/L or a relative amount such as 1.2, 1.3, 1.4, 1.5, 1.6, 1.7, 1.8, 1.9, 2.0, 2.2, 2.4, 2.6, 2.8, 3.0, 3.2, 3.4, 3.6, 3.8, 4.0, 4.2, 4.4, 4.6, 4.8, 5.0, 10, 15, 20, 25, 30, 40, 60, 80 and/or 100 times or greater a control level, standard or reference level. Optionally, a control is a level such as the average or median level in a control sample. The level of biomarker can be, for example, the level of protein, or of an mRNA encoding for the biomarker such as a dopamine receptor.

In one embodiment, when the level of two or more biomarkers is determined, the levels of the two or more biomarkers can be used to generate an expression profile for the subject. For example, in one embodiment, the methods described herein include determining a level for two or more biomarkers in the sample, generating an expression profile based on the level of the two or more biomarkers and comparing the expression profile to a control expression profile. A difference or similarity in the test sample expression profile and the control expression profile is then used to provide a prognosis for the test subject, identify the subject as having cancer, or indicate whether the subject is suitable for treatment with a dopamine receptor antagonist.

A further aspect of the disclosure includes the use of a dopamine receptor antagonist for the treatment of cancer or a precancerous disorder. In a similar aspect, there is provided a dopamine receptor antagonist for use in the treatment of cancer or a precancerous disorder. In one embodiment the cancer is leukemia. In one embodiment, the leukemia is acute myeloid leukemia or monocytic leukemia. In one embodiment, the dopamine receptor antagonist is a phenothiazine derivative such thioridazine or chlorpromazine. In one embodiment, the DR antagonist is selected from the compounds listed in Table 1.

Also disclosed herein is the use of a dopamine receptor antagonist for the manufacture of a medicament for the treatment of a cancer and/or a precancerous disorder.

A further aspect of the disclosure includes methods of screening compounds for anti-cancer activity comprising identifying compounds that antagonize one or more dopamine receptors. In one embodiment, compounds that antagonize dopamine receptors are identified as having anti-cancer activity. In one embodiment, the methods include screening compounds to identify those that reduce the proliferation of cancer stem cells relative to normal stem cells such as hematopoietic stem cells as set out in Examples 7 and 8 of the present description.

The following non-limiting examples are illustrative of the present disclosure:

EXAMPLES

Example 1

Thioridazine is Cytotoxic to Leukemic Cell Lines

The effect of Thioridazine on normalized cell number was evaluated in 3 leukemic cells lines: HL-60, MV4-11 and OCI-AML3. All three lines are leukemic cell lines. HL-60 was derived from promyelocytic AML whereas MV 4-11 and OCI-AML3 are representative of AML. Each compound was incubated with the cells for 72 h. The control was DMSO (ie the vehicle used for the compound) for 72 h. Each condition had three replicates.

As shown in FIG. 1, doses of 0.1 µM and 1 µM thioridazine had little effect on normalized cell number, while at 10 µM the normalized cell number was reduced to almost zero.

Example 2

Differential Activity of Thioridazine on AML Blast-Forming Potential and Colony Forming Potential of Normal Stem Cells The effects of thioridazine on blast formation in an AML cell line was compared to the effect of thioridazine on colony formation in normal human stem cells.

Figure 2:
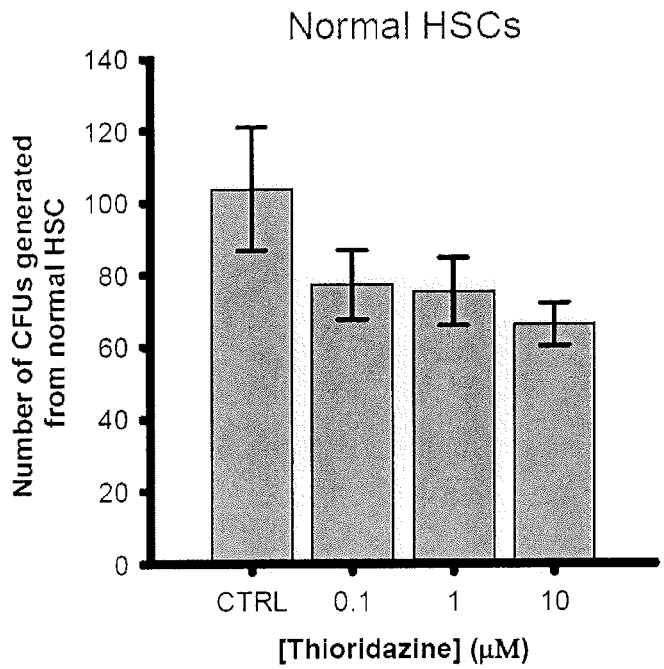
FIG. 2 shows that thioridazine 10 µM has limited affects on the colony forming potential of normal HSCs (2A) while significantly reducing AML blast forming potential.
Figure 2:
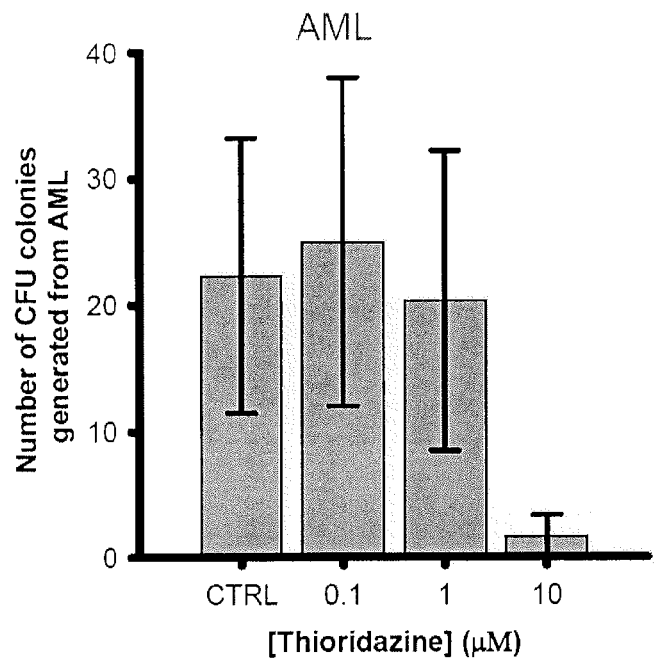

Normal HSCs and progenitors were sourced from either mobilized peripheral blood or umbilical cord blood of health patients. Primary AML cells were taken from patients diagnosed with AML. Both normal HSCs and primary AML cells were cultured under standard in vitro methocellulose assay conditions (see http://www.stemcell.com/en/Products/All-Products/MethoCult-H4434-Classic.aspx as well as Clinton Campbell et al. The human stem cell hierarchy is defined by a functional dependence on Mcl-1 for self-renewal capacity. Blood 116 (9) 1433-1442 (Jun. 4, 2010), hereby incorporated by reference) for at least 14 days before the number of colonies were recorded. As shown in FIG. 2, 10 µM thioridazine has a differential effect on normal HSCs versus AML cells. 10 µM thioridazine reduced the colony forming potential of normal HSCs from about 100 (CTRL treated with DMSO) to about 66 total colonies (FIG. 2A), but had a much more significant effect on AML cells reducing the number of CFU colonies to about 22 blast colonies (FIG. 2B) to 1.6 blast colonies.

Figure 3:
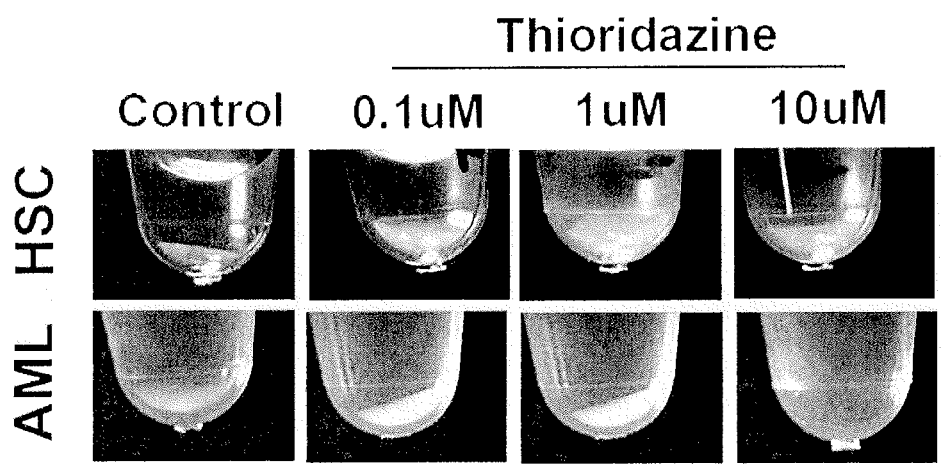
FIG. 3 shows cell pellets of CFU colonies generated from normal HSC and AML treated with Thioridazine.

FIG. 3 shows cell pellets of CFU colonies generated from normal HSC and AML treated with thioridazine. At a dose of 10 µM, pelleted cells are still visible for HSCs, but not for AML cells. Thioridazine therefore selectively targets Blast-CFU Potential of AML cells.

Example 3

Chlorpromazine is Toxic to AML Cell Lines

Figure 4:
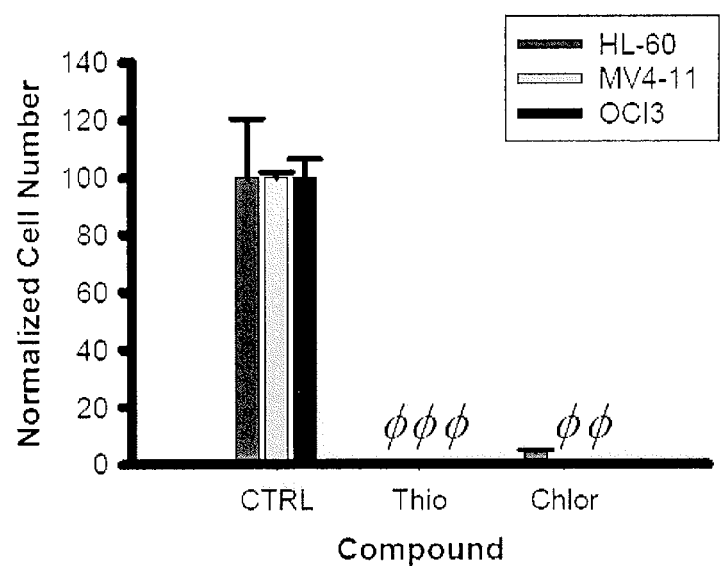
FIG. 4 shows that both 10 µM chlorpromazine and 10 µM thioridazine is cytotoxic to leukemic cell lines HL-60, MV4-11 and OCI3.

The dopamine receptor antagonist and phenothiazine-related compound chlorpromazine was also investigated for effects on the AML cell lines HL-60, MV4-11 and OCI-AML3. Testing was performed as set out in Example 1. As shown in FIG. 4, 10 µM Chlorpromazine is toxic to AML cell lines.

Example 4

Expression of Dopamine Receptors in Normal Blood Versus Leukemia

The expression of the dopamine receptors DR1, DR2, DR3, DR4 and DR5 were analyzed in AML cell lines HL-60, MV4-11, AML-OCI2 and AML-OCI3), Primary AML cells (AML22101, AML29428, AML22174, AML29560) isolated from AML patients, normal blood mononuclear cells (MNC) (MPB21471 and MPB28137; healthy patient blood) as well as umbilical cord blood primary cells enriched for normal Human Stem Cells or progenitors (CB107, CB108 and CB109) using StemSep® Human Hematopoieitc Progenitor Cell enrichment kit (http://www.stemcell.com/en/Products/All-Products/Stem-Sep-Human-Hematopoietic-Progenitor-Cell-Enrichment-Kit.aspx) and enrichment levels of HSCs/Human Progenitor cells confirmed by flow cytometry. Isotype expression was measured as background. Peaks to the right of the isotype peak represent positive expression of DR markers.

As shown in FIG. 5, dopamine receptors are expressed on primary AML, AML cell lines and normal mononuclear blood cells (MNC) but not in blood enriched for normal HSCs (CB(lin−). The data shows that when the sample is positive for DR expression that all five DR subtypes are usually present.

Not all primary AMLs were observed to express dopamine receptors. Accordingly, subjects may be pre-screened for the expression of dopamine receptors in order to identify subjects suitable for AML treatment with DR antagonists. Optionally, pre-screening of subjects may encompass all five DR subtypes, or specific subtypes or combination of subtypes.

Example 5

Multiple DR Antagonists are Cytotoxic to AML Cell Lines

A series of dopamine receptor agonists, $D_3$-antagonists, $DR_{1\ \&\ 5}$-antagonists and multi-receptor antagonists were tested for cytotoxicity against three AML cell lines HL-60, OCI-AML2 and OCI-AML3. Testing was performed as set out in Example 1.

Figure 6:
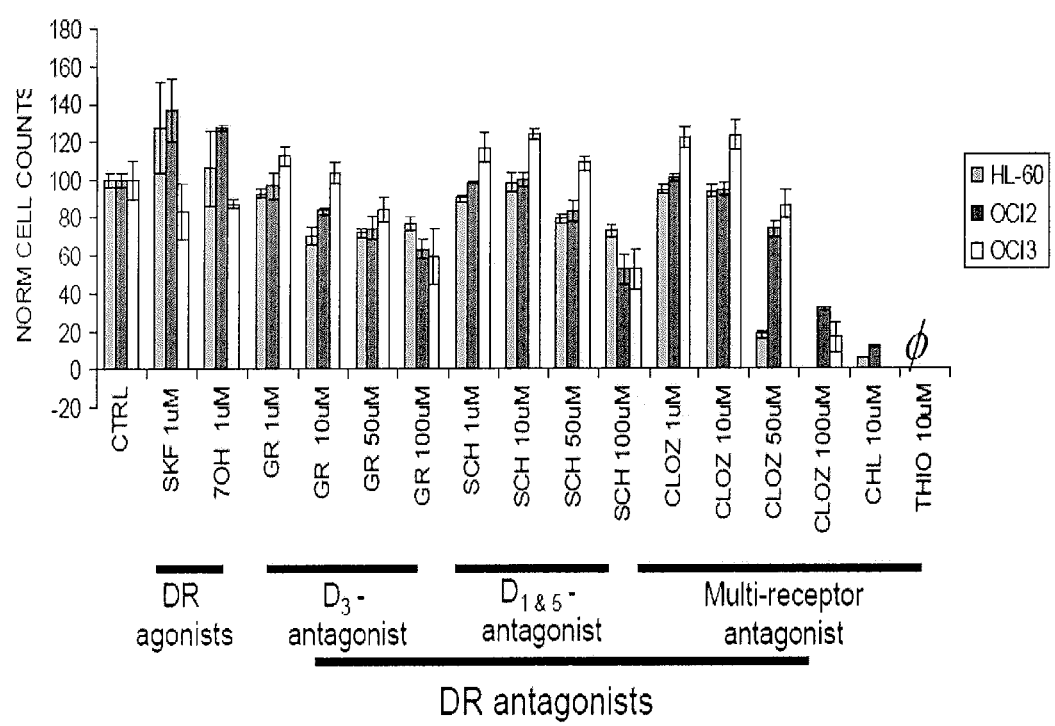
FIG. 6 shows that multiple DR antagonists are cytotoxic to AML cell lines. SKF=(R)-(+)-SKF-38393 hydrochloride; 7OH=R(+)-7-Hydroxy-DPAT hydrobromide; GR=GR 103691; SCH=R(+)-SCH-23390 hydrochloride; CLOZ=Clozapine; CHL=Chlorpromazine hydrochloride; THIO=Thioridazine.

As shown in FIG. 6, CLOZ at higher concentrations as well as CHL and THIO have a significant effect on cytotoxicity of AML cell lines. Without being limited by theory, the cytotoxic effect may require inhibition of multiple dopamine receptors. THIO, CHL and CLOZ being multireceptor antagonists work to eradicate the AML cell lines while the $D_3$ and $DR_{1\ \&\ 5}$-specific antagonists only reduce cell count to 60%.

Example 6

Dopamine Receptors are Expressed in the CD14+ Cell Population of Primary AML

The expression of dopamine receptor subtypes was analyzed in primary AML cells. Primary AML cells obtained from AML patients were co-stained with antibodies specific to the DR subtype and CD14 prior to being analyzed using flow cytometry. The majority of DR+ cells were found to be positive for CD14.

Figure 7:
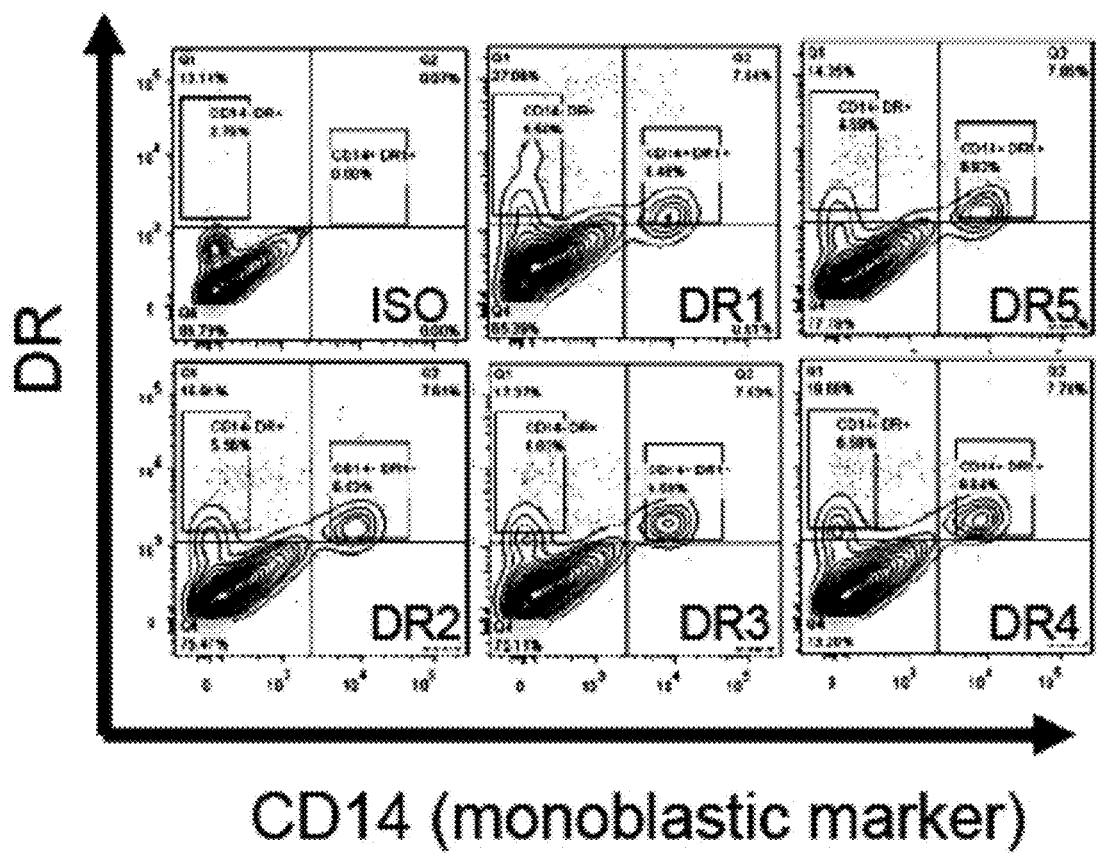
FIG. 7 shows FACS data showing that dopamine receptors are expressed in the population of CD14+ cells in primary AML.

As shown in FIG. 7, the expression of the CD14 monocytic marker is correlated with the expression of each DR subtype.

The effects of thioridazine were also examined on a subpopulation of CD14+ cells in primary AML. Primary AML cells were cultured under control (DMSO vehicle) or 10 uM thioridazine for 72 h and then stained for with antibodies specific to CD14. The number of CD14+ cells in both control and thioridazine treated samples was determined using flow cytometry and the frequency of CD14+ cells was found to be lower in the thioridazine treated sample, suggesting that this compound selectively targets the CD14+ subpopulation in AML cells.

Figure 8:
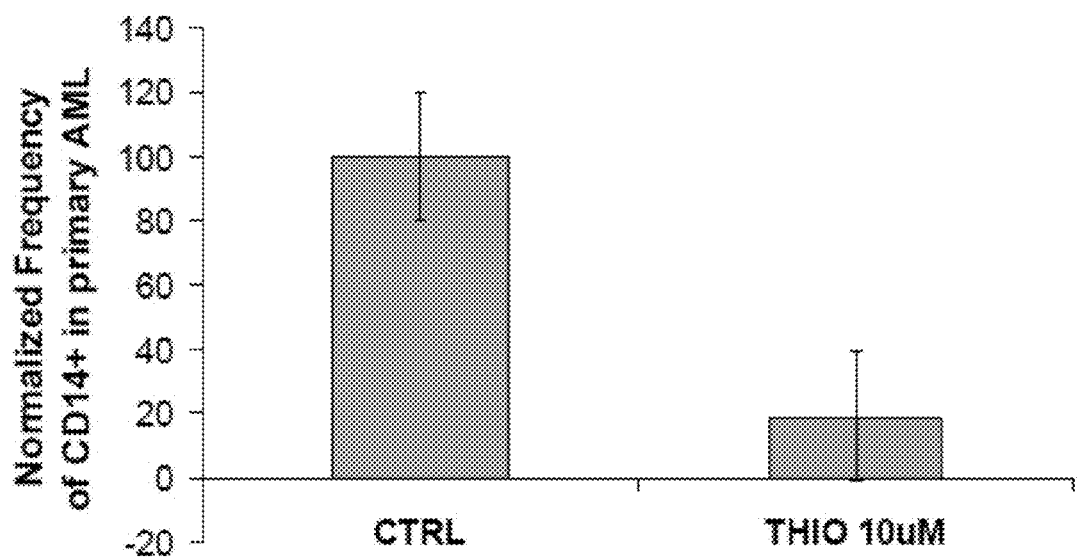
FIG. 8 shows that thioridazine selectively targets and reduces the normalized frequency of CD14+ cells in primary AML.

As shown in FIG. 8, 10 µM thioridazine also reduced the normalized frequency of CD14+ cells in primary AML cells, showing that thioridazine selectively targets CD14+ cells. The AML control group contained a fraction of CD14+ cells. This fraction is reduced with thioridazine treatment and is represented as a reduction in the normalized frequency of the control (100%) versus treated (20%).

Example 7

Identification and Characterization of Drugs that Induce Differentiation of hPSCs Identification of drugs that target cancer stem cells (CSCs) without affecting normal stem cells (SCs) would be ideal for future cancer therapies, but is limited by the lack of assays for both CSCs and normal SCs in the human that are amenable to robust biological screens. As set out in the following examples, using a neoplastic vs. normal human pluripotent stem cell (hPSC) differentiation platform, compounds were identified that are not toxic, but induce differentiation to overcome neoplastic self-renewal of CSCs. Of the several candidate anti-CSC agents identified, thioridazine, an approved anti-psychotic drug, was able to selectively target human somatic CSCs capable of in vivo leukemic disease initiation while having no effect on normal blood SC capacity. Antagonism of dopamine receptor (DR) signaling by thioridazine forms the basis of selective CSC targeting, and revealed DR as a biomarker for CSCs of hematopoietic and breast tumor origins.

Experimental Procedures

Generation of Neoplastic hPSC EOS-GFP Lines

Neoplastic v1H9 or v2H9 hPSC cells (Werbowetski-Ogilvie et al., 2009) were transduced with lentivirus bearing the EOS-C3+ or EOS-S4+ vectors provided by Dr James Ellis (Hotta et al., 2009). After lentiviral transduction cells were selected using Puromycin, and subsequently sorted as single cells into a 96-well plate based on GFP expression using a FASCAria II (Becton-Dickinson). Colonies generated from single cell clones were used to establish the v1H9-Oct4-GFP (EOS-C3+), v2H9-Oct4-GFP (EOS-C3+) and v1H9-Sox2-GFP (EOS-S4+) lines.

Cell Culture.

The H9 hESC, v1H9, v1H9-Oct4-GFP, v2H9-Oct4-GFP, v1H9-Sox2-GFP and fibroblast-derived iPSCs were cultured as previously described (Chadwick et al., 2003; Werbowetski-Ogilvie et al., 2009).

Primary Human Samples.

For AML specimens, peripheral blood and/or bone marrow was collected at the time of clinical presentation. Healthy hematopoietic cells were obtained from umbilical cord blood samples. All samples were obtained following informed consent according to Research Ethics Board approved protocols at McMaster University and the London Health Sciences Centre. Human breast tumor samples were obtained from reduction mammoplasty surgeries following informed consent according to Research Ethics Board approved protocols at McMaster University.

In Vitro Culture Platform for Normal and Neoplastic hPSCs.

Chemical screens involved v1H9-Oct4-GFP cells seeded at 5,000 cells per well in mouse embryonic fibroblast conditioned media (MEFCM) supplemented with 8 ng/ml bFGF. 24 hours later the media was exchanged for MEFCM with compounds at 10 µM and 0.1% DMSO, 0.1% DMSO (−BMP4) or 100 ng/ml of BMP4 and 0.1% DMSO (+BMP4) for 48 hours before being exchanged with fresh media with compound for a further 24 h (total compound treatment time 72 h) prior to being fixed and prepared for automated imaging and plate reader analysis. Confluent H9 & fibroblast-derived iPSC were seeded at 10,000 cells per well in MEFCM supplemented with 8 ng/ml bFGF. 24 hours later the cells were treated with compounds at 10 μM and 0.1% DMSO, 0.1% DMSO (−BMP4) or 100 ng/ml of BMP4 and 0.1% DMSO (+BMP4). Fresh MEFCM supplemented with compounds was exchanged daily for 5 days. On day 5, hPSC's were fixed and prepared for automated imaging and plate reader analysis. See supplementary experimental procedures for further details.

Teratoma Assay.

400,000 H9 hESCs or v1H9-Oct4-GFP were injected intra-testicularly into male NOD/SCID mice and teratomas analyzed for Oct4 as previously described. (Werbowetski-Ogilvie et al., 2009).

Xenotransplantation Assays.

NOD.Cg-Prkdc$^{scid}$ Il2rg$^{tm1Wjl}$/SzJ adult mice (NSG) were sub-lethally irradiated with 315 rads 24 hours prior transplantation. $0.8$-$1.0\times10^7$ AML MNCs or $1.5$-$1.8\times10^5$ CB lin− hematopoietic cells treated with compound or DMSO-vehicle for 24 h were injected via tail vein (IV). After 6-10 weeks, animals were culled, and the BM and spleen were analyzed for the presence of human cells by flow cytometry (LSRII, BD) and data was analyzed using FlowJo software (Tree Star Inc). For secondary HSPC transplants, equal number of engrafted human cells from CB lin− transplants were injected IV in adult irradiated NSG mice as described for primary transplants.

Statistical Analysis.

Data is represented as the mean±SEM or mean±SD. Significant differences between groups were determined using unpaired two-way or one-way Students' t test.

Pluripotent Stem Cell Culture.

The H9 hESC, v1H9, v1H9-Oct4-GFP, v2H9-Oct4-GFP, v1H9-Sox2-GFP and fibroblast-derived iPSCs were cultured on Matrigel™-coated (BD Biosciences 353234) plates with mouse embryonic fibroblast-conditioned (MEFCM) media supplemented with 8 ng/ml bFGF (GIBCO 13256-029). MEFCM is composed of KO-DMEM (GIBCO 10829-018), 20% KO-Serum Replacement (GIBCO 10828-028), 1% Non-Essential Amino Acids (GIBCO 11140-050), 1 mM L-Glutamine, 0.1 mM β-mercaptoethanol (Sigma Aldrich M7522). Cell lines were passaged every 7 days using 100 Units/mL of Collagenase IV (GIBCO 17104-019) for 2-3 minutes. Cell seeding density, assay duration and DMSO vehicle concentration in 96 wells were optimized for v1H9-Oct4-GFP cells and normal H9 hPSC. For v1H9-Oct4-GFP, an optimum initial seeding density of 5,000 cells per well for 72 h of treatment was selected based on maximal levels of GFP and z' discrimination between ±BMP4 controls. For normal hPSC, an optimal seeding density of 10,000 cells per well was selected based on maximal z'-prime discrimination between ±BMP4 controls.

Primary Human Samples.

Mononuclear cells were prepared using Ficoll-Paque Premium (GE Healthcare). For hematopoietic cells, lineage depletion was performed using EasySep (StemCell Technologies) following manufacturer's recommendations.

AML/HPSC Cell Culture.

AML cell lines, namely, OCI-AML2 (M4), OCI-AML3 (M4), HL-60 (M2) and MV-4-11 (M5) were cultured in RPMI (Gibco) supplemented with 5% heated-inactivated FBS (HyClone). For DR agonist studies with R(+)-7-Hydroxy-DPAT hydrobromide (Sigma), serum-free conditions were employed instead due to the prevalence of dopamine in FBS (Little et al., 2002). AML patient blasts were cultured in IMDM supplemented with 5% heated inactivated FBS (HyClone), 5 ng/mL IL3 (R&D systems), $5\times10^{-5}$ M β-mercaptoethanol (Sigma) and BIT (StemCell Technologies). HSC media contained IMDM supplemented with 1% BSA (Sigma), 100 ng/mL SCF (R&D systems), 100 ng/mL Flt-3L (R&D systems) and 20 ng/mL TPO (R&D systems). Patient HSPC and AML samples were treated with compound or DMSO-vehicle (0.1%) for 24 h prior to CFU plating or xenotransplantation studies.

Antibodies.

Antibodies used for immunocytochemistry were the following: Oct3/4 (BD Trunsduction Laboratories, cat#611203), Sox2 (R&D, cat#AF2018). To detect human hematopoietic cells, Pacific Blue−, PE−, APC− or FITC labeled anti-human CD45 was used (BD Biosciences). FITC anti-CD33, PE anti-CD13, FITC anti-CD41a, FITC anti-HLA DR, and PE anti-CD19 antibodies were obtained from BD Pharmingen. PE anti-CD14, PE anti-CD15 and PE anti-GlyA were acquired from Immunotech Beckman Coulter. To determine pluripotency, PE anti-SSEA3 (BD Biosciences) and PE- or AlexaFluor488 anti-Oct4 (BD Biosciences). Rabbit anti-human dopamine receptor antibodies; DRD1 (Cat#324390), DRD2 (Cat#324393), DRD3 (Cat#324402), DRD4 (Cat#324405) and DRD5 (Cat#324408) were sourced from EMD Chemical. Anti-rabbit Alexa-Fluor-488 (Molecular Probes) was used as the secondary antibody. Primary anti-p53 (Cat#2527) and anti-p21 (Cat#2947) rabbit IgG sourced from Cell Signaling Technology were used to stain fixed and permeabilized cells. Anti-rabbit alexa-Fluor-546 (Molecular Probes) was used as the secondary antibody. For breast tumor staining, APC anti-CD44 and PE-CD24 were sourced from BD Pharmingen.

Automated Imaging and Analysis

Imaging Neoplastic hPSC.

Cells were fixed in 2% paraformaldehyde and stained with 10 μg/mL Hoechst 33342 (Invitrogen) with a Combi Multidrop Dispenser (Thermo). For experiments that involved Oct4 immunocytochemistry, a monoclonal antibody for Oct4 (BD) was used along with an Alexa-Fluor-647 secondary (Invitrogen). Immunocytochemical staining was performed by a Janus automated liquid handler (Perkin Elmer). Images were acquired at 10×N.A with an Arrayscan HCS VTI Reader (Cellomics) by means of epi-fluorescence illumination and standard filter sets.

Imaging Normal hPSC.

Cells were fixed in 2% paraformaldehyde and stained with 10 μg/mL Hoechst 33342 (Invitrogen). Standard fluorescence immunocytochemical techniques were used to stain the cells with a monoclonal antibody for Oct4 (BD), and an Alexa-Fluor-647 secondary antibody (Invitrogen). All steps were performed by a Janus automated liquid handler (Perkin Elmer). Images were acquired at 5× with an Arrayscan HCS Reader (Cellomics) by means of epi-fluorescence illumination and standard filter sets.

Image Analysis.

Image analysis was performed using custom scripts in Acapella software (Perkin Elmer). Nuclear objects were segmented from the Hoechst signal. For neoplastic cell lines, object intensity analysis was performed on GFP positive cells only. For normal cell lines, the fraction of Alexa-Fluor-647-positive cells was quantified. Images and well-level data were stored and analysed in a Columbus Database (Perkin Elmer) and further data analysis, compounds registration and hit identification in ActivityBase (IDBS).

Gene Expression Analysis.

Cells in specific conditions were collected and RNA was extracted by using RNeasy kit (Qiagen), complementary DNA (cDNA) generation by using SuperScript III® cDNA synthesis kit (Invitrogen), pre-amplification and TaqMan® array reaction (Applied Biosystems) were performed according to manufacturer's instructions. The gene expression profile for each treated cell population was analyzed using TaqMan® Stem Cell Pluripotency Array Card on ViiA 7 Real-Time PCR System (Applied Biosystems). Each reaction sample was dispensed into loading wells on the array card and centrifuged twice at 336×g for 1 min each time, sealed, and placed in the thermal cycler. The following cycling conditions were used for all array card applications: 45° C. for 10 min, 94° C. for 10 min, and 40 cycles of 94° C. for 30 s followed by 60° C. for 1 min. Array data were normalized to 18S RNA and GAPDH and comparisons were performed using data analysis 2.0 software (Applied Biosystems).

Methylcellulose Colony-Forming Assay.

AML patient or CB lin− cells were cultured 24 hours in the presence of compound or DMSO-vehicle (0.1%) control. AML cells were plated at 50 000 cells/mL in Methocult GF H4434 (Stem Cell Technologies). CB lin− cells were plated at 1000 cells/mL in Methocult GF H4434 (Stem Cell Technologies). Colonies were scored after 14 days of culture using standard morphological criteria.

Volumetric Cell Counting.

The number of AML-OCI2 and AML-OCI3 cells present after 72 h treatment with DR antagonists (FIG. 16b) and agonist (FIG. 16c-d) were counted by measuring the number of events within a fixed volume following the grating strategy defined by forward scatter and side scatter clustering, 7AAD− and Hoechst+.

Human Breast Cancer Sample Processing.

Human breast tumor samples were obtained from reduction mammoplasty surgeries following informed consent according to Research Ethics Board approved protocols at McMaster University. The breast tumor chunks were cut into small fragments (chunks of less than 1 mm) with scissors and scalpel. Subsequently, 3 mL of Versene (1 mL of 0.5M EDTA in 1 L of 1×PBS) and 7 mL of trypsin-collagenase solution were added for each gram of tumor tissue and incubated for 30 min at 37° C. The trypsin-collagenase solution consisted of RPMI 1640 (Gibco #11875093), 2% penicillin/streptomycin (Invitrogen #15140163), 1% Fungizone Antimycotic (Invitrogen #15290018), 2% FBS, 3 mg/mL Collagenase A (Roche Diagnostics #11088793001), and 0.1% of 2.5% trypsin (Gibco #15090). An equal volume of RPMI 1640 with 2% FBS was then added to the tissue suspension. The tissue suspension was filtered through a 40 μm nylon strainer (Falcon #352340). The supernatant was discarded and the cell pellet was resuspended in 10 mL of F-12+GlutaMAX Nutrient Mixture Ham 1× (Gibco #31765) supplemented with 2% penicillin/streptomycin and 1% Fungizone Antimycotic. Viable cells were counted using a hemocytometer and Trypan blue solution and prepared for flow cytometry. Antibody staining included Rabbit anti-human dopamine receptor antibodies; DRD1 (Cat#324390), DRD2 (Cat#324393), DRD3 (Cat#324402), DRD4 (Cat#324405) and DRD5 (Cat#324408) were sourced from EMD Chemical and Anti-rabbit Alexa-Fluor-488 (Molecular Probes) was used as the secondary antibody along with APC anti-CD44 and PE-CD24, both sourced from BD Pharmingen.

Example 8

High Throughput Screening Identification of Compounds that Induce Differentiation of Neoplastic hPSCs The inventors have previously described a variant human pluripotent stem cell (hPSC) line that displays neoplastic features which include enhanced self-renewal and survival, along with aberrant block in terminal differentiation capacity in vitro and in vivo (Werbowetski-Ogilvie et al., 2009). Based on these similarities in functional properties to somatic CSCs, neoplastic hPSCs were examined as a surrogate for somatic CSCs that would be amenable for high content and high throughput screening in vitro. A screening platform was developed to identify small molecules that selectively target neoplastic hPSCs whilst having little effect on normal hPSCs. This differential screening platform is capable of identifying potent candidate drugs that selectively target somatic CSCs while sparing healthy SC capacity.

Oct4 and Sox2 provide a reliable indicator of loss of self-renewing pluripotent state and differentiation induction of normal and neoplastic hPSCs. To provide a more straightforward method for detecting loss of Oct4 or Sox2 during induced differentiation of neoplastic hPSCs, GFP-reporter lines were generated by transduction of neoplastic hPSCs with the EOS-GFP reporter (v1H9-Oct4-GFP and v1H9-Sox2-GFP, respectively) (Hotta et al., 2009). GFP intensity was observed to be correlated with Oct4 and Sox2 expression in treatments that favored self-renewal stability and conditions that induce differentiation with the addition of BMP4. This response was consistently found using an additional neoplastic hPSC line, v2H9 (Werbowetski-Ogilvie et al., 2009) transduced with the same EOSlentivirus GFP-reporter (v2H9-Oct4-GFP), as well as a Sox2 reporter line (v1H9-Sox2-GFP).

The uniform response to differentiation and maintenance of pluripotency in all hPSC cell lines generated also revealed that viral integration or clonal selection by EOS reporter construct insertion is irrelevant to responsiveness. These results suggest that compounds that induce differentiation can be identified based on the reduction of GFP intensity in neoplastic hPSC reporter lines and could be exploited for chemical screening. To that end, conditions for automated high content microscopy and fluorimetric-based high throughput screening were used to detect reductions in pluripotency marker expression of hPSCs. Microscopic analysis of normal hPSCs showed that distinct Oct4+ cells are lost following BMP4 treatment. Similarly, the reduction in both GFP and Oct4 due to BMP4 treatment of neoplastic Oct4-GFP hPSCs was quantified by high content microscopy and plate reader-based fluorimetry. To identify ideal candidates for targeting CSCs differentiation of both normal and neoplastic hPSCs in response to compound treatment was assessed in parallel.

Figure 9:
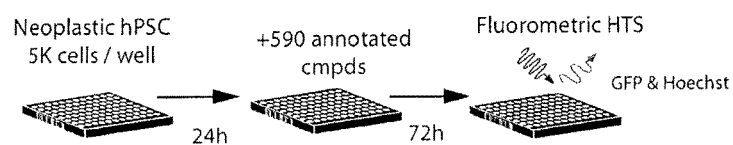
FIG. 9 shows the identification of mefloquine and thioridazine using chemical screening for compounds that differentiate neoplastic hPSC. (A) Schematic of screening strategy. (B) XY-scatter plot of percent residual activity (% RA) of GFP and Hoechst signals of the 590 compound screen. Region outlined demonstrates loss of pluripotency (LOP) as defined by reduced GFP and Hoechst. Each point n=3, mean+/−SD (C) Summary of responses seen with 590 compounds. (D) Chemical structure of candidate compounds; thioridazine, azathioprine and mefloquine. (E) Representative GFP, Hoechst and merged microscopic images of v1H9-Oct4-GFP cells treated with candidate compounds at 10 µM. (F) Histogram of GFP intensity of these images. (G) Dose response curves of v1H9-Oct4-GFP treated with candidate compounds and calculation of $EC_{50}$. Each point n=3; mean+/−SEM.
Figure 9:
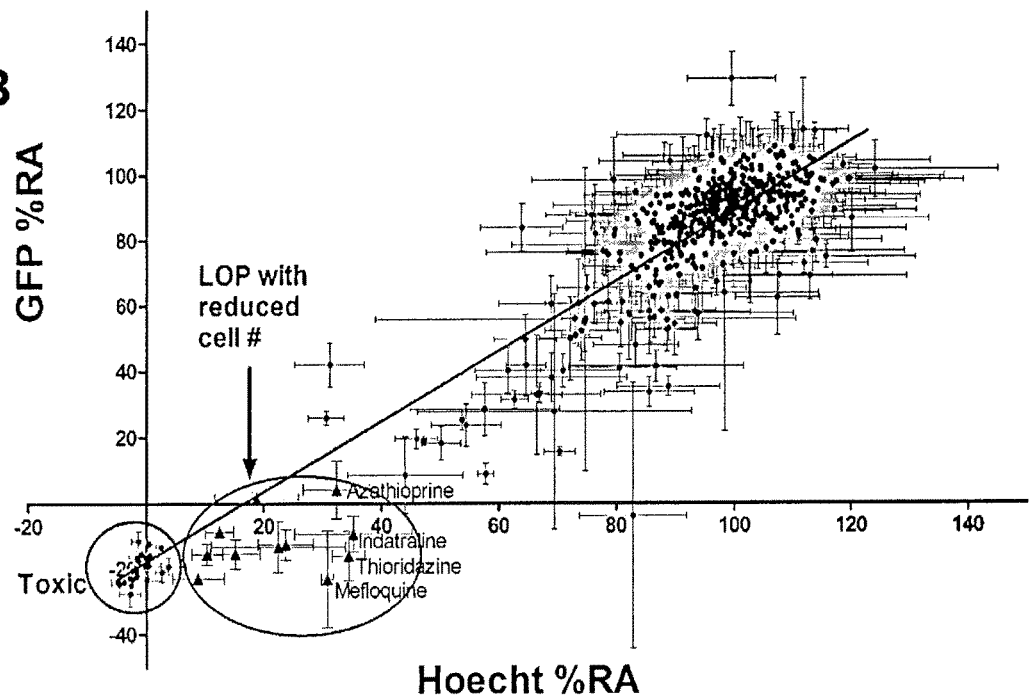
Figure 9:
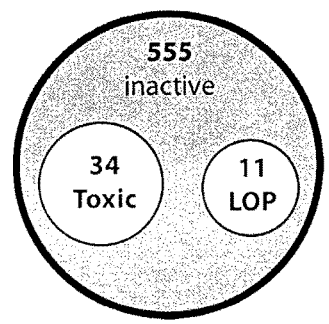
Figure 9:
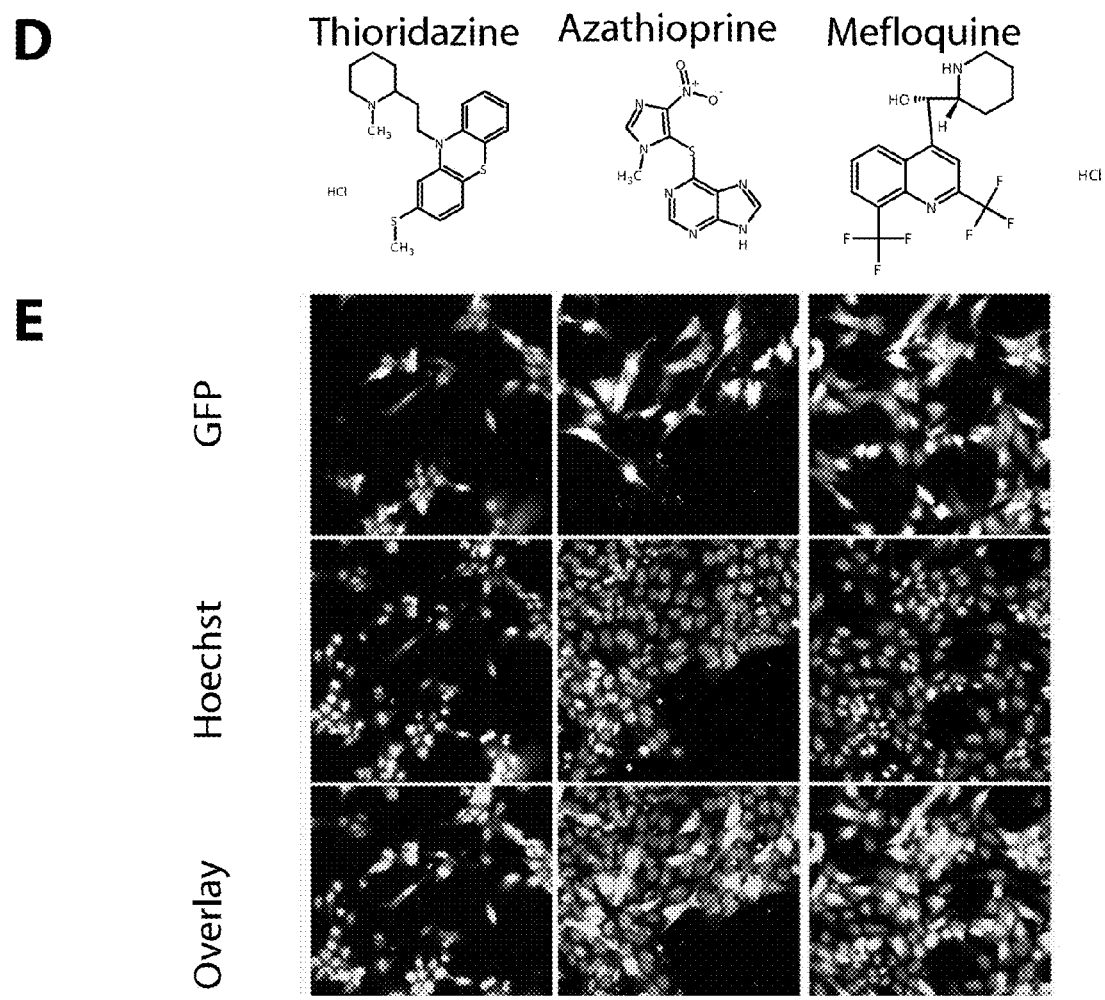
Figure 9:
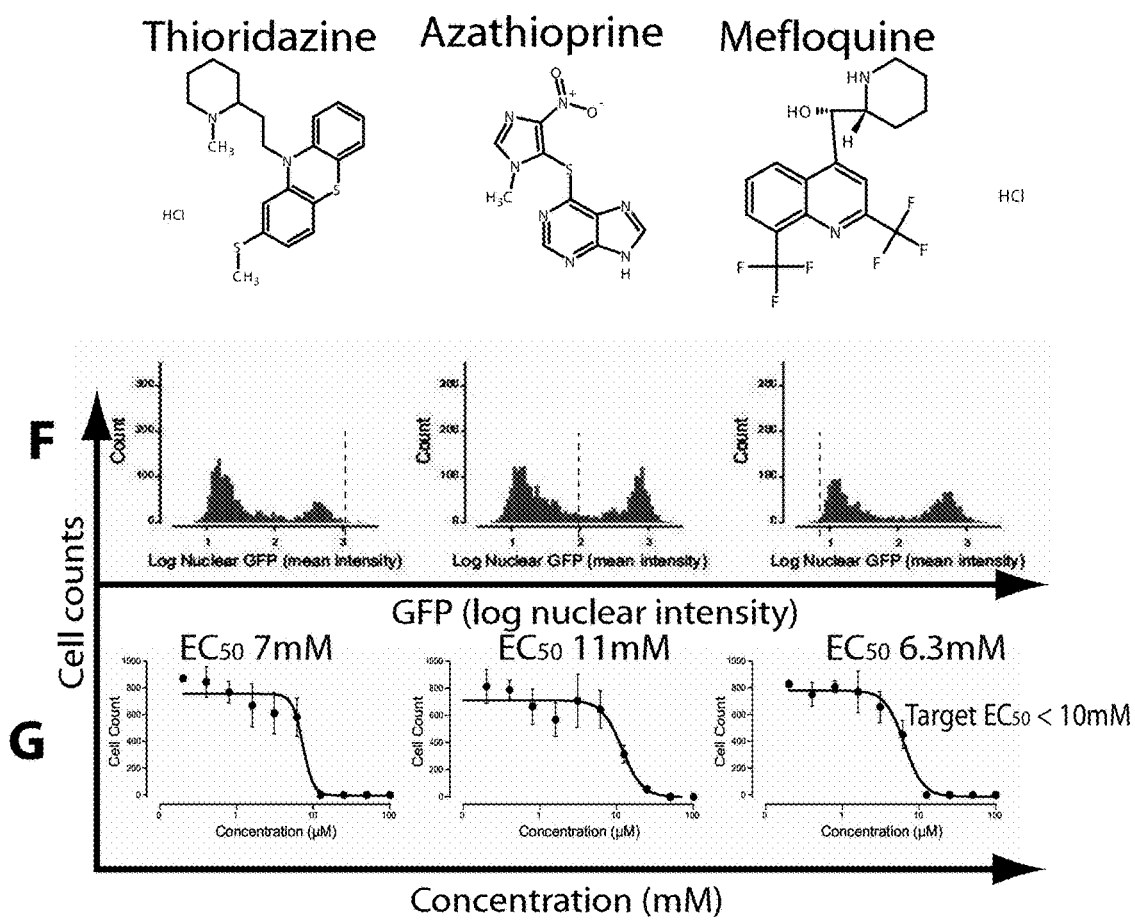

Given the validation of the screening platform a chemical libraries composed of 590 well-established annotated compounds from the NIH Clinical Collection and Canadian Compound Collection was screened. These Collections have been previously scrutinized in numerous other mammalian cell lines (Diallo et al., 2010; Shoemaker, 2006). Following the demonstration that fluorometric high throughput screening (HTS) and high content screening (HCS) platforms give equivalent measurements for loss of pluripotency (GFP RFU and mean GFP intensity per cell, respectively) and cell count (Hoechst RFU and Cell count, respectively) of the 51 defined compounds, HTS was selected as the preferred platform for more rapidly screening compound libraries (FIG. 9a). Of the 590 compounds screened (at 10 μM based on previous studies (Inglese et al., 2007)), 11 compounds were identified to induce differentiation as indicated by a reduction in both GFP % residual activity (% RA) and Hoechst % RA (FIGS. 9b-c). A total of 4 of these compounds; indatraline, thioridazine, azathioprine, and mefloquine, were identified as candidate compounds based on clustering and levels of Hoechst % RA in excess of 30% (FIG. 9b). Secondary high content analysis revealed indatraline to be a questionable candidate and was thus excluded, whereas content analysis and HTS analyses dually confirmed thioridazine, azathioprine, and mefloquine as candidate compounds (FIG. 9d) and were thus selected for further testing (FIGS. 9e-g). When compared to control-treated hPSCs, each compound appeared to induce distinct morphological changes in neoplastic hPSCs (FIG. 9e). Reduction in GFP intensity was confirmed using image analysis (FIG. 9f) and further assessed over a wide range of doses to calculate half-maximal effective concentration (EC50) for each compound (FIG. 9g). Only thioridazine and mefloquine were found to possess EC50 values lower than the 10 μM target threshold (FIG. 9g) and thus defined as candidates for further in depth evaluation using neoplastic hPSCs and somatic CSCs from patients.

Example 9

Figure 10:
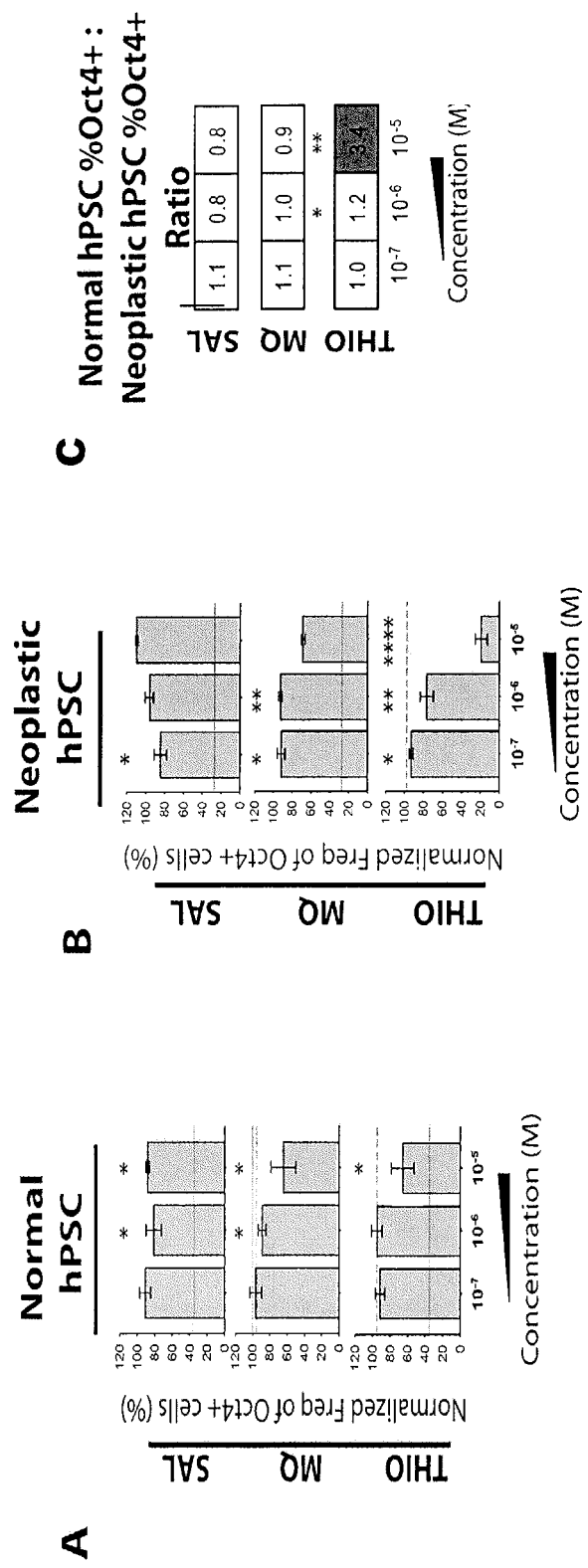
FIG. 10 shows the effect of salinomycin, mefloquine and thioridazine on normal and neoplastic populations. (A-B) Flow cytometry analysis of frequency of Oct4+ cells in (A) H9 and (B) v1H9-Oct4-GFP cells treated with salinomycin (SAL), mefloquine (MQ) and thioridazine (THIO) at $10^{-7}$-$10^{-6}$ M. Each bar n=3; mean+/−SD. Values are normalized to DMSO-treated control samples; (−) DMSO mean, (−−) mean minus one SD, (−) level of % Oct4+ in BMP4 treated samples. (C) Ratio of normalized % Oct4+ cells in H9 per v1H9-Oct-GFP with same compound at the same concentration. Percent of neoplastic hPSC staining positive for (D) p53 and (E) p21 following 24 h treatment with 10 µM etoposide, 10 µM thioridazine (THIO), BMP4 and DMSO-treated (CTRL) controls. Each bar n=3; mean+/−SD. Representative images of etoposide and thioridazine treated cells included. Arrows show p53+ and p21+ in etoposide-treated cells versus thioridazine-treated cells. (F) Differentiation-associated genes with >2 fold increase following thioridazine treatment of neoplastic hPSC. Genes divided into respective lineages, endoderm (ENDO), mesoderm (MESO), germ cell (GERM), neural (NEURO) and trophoblast (TROPH). Each bar represents the mean of two separate experiments. (G-K) Hematopoietic multilineage and clonogenic potential in response to compound treatment detected using methylcellulose assays. Representative colony forming unit (CFU) pellets of (G) hematopoietic stem and progenitor cells (HSPC) versus (H) AML blast CFUs pellets following compound treatment. (I-J) Quantification of respective CFUs and blast-CFUs generated from (I) HSPC and (J) AML blast cells following compound treatment. Values were normalized to DMSO-treated control samples; (−) DMSO mean, (−−) mean minus one SEM. Each HSPC bar n=7 individual samples, mean+/−SEM. Each AML bar at least n=5 individual patient samples, mean+/−SEM. (K) Ratio of normalized HSPC CFUs per AML blast CFUs with same compound at the same concentration. (L) Frequency of normalized CD11b granulocytic cells in cultured patient AML cells treated with thioridazine 10 µM (THIO 10 µM) or DMSO vehicle (CTRL) for up to 96 hours. Each bar n=3, mean+/−SD. (*) p<0.05, () p<0.01, (*) p<0.001, (****) p<0.0001.
Figure 10:
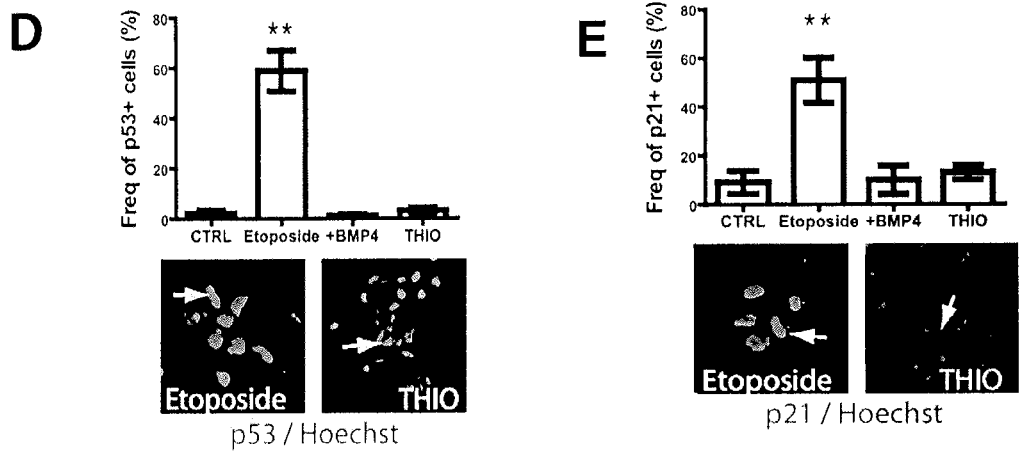
Figure 10:
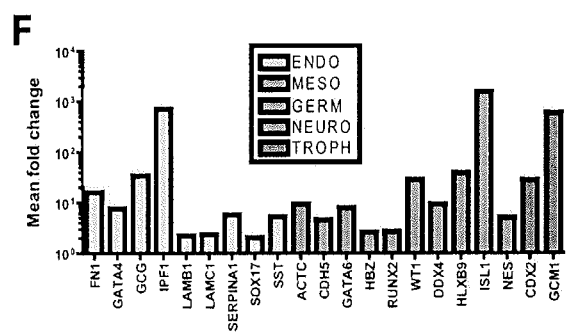
Figure 10:
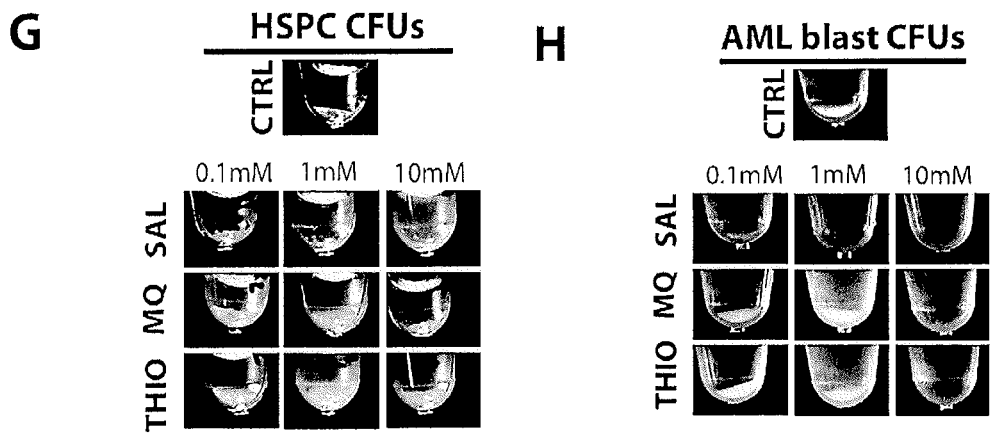
Figure 10:
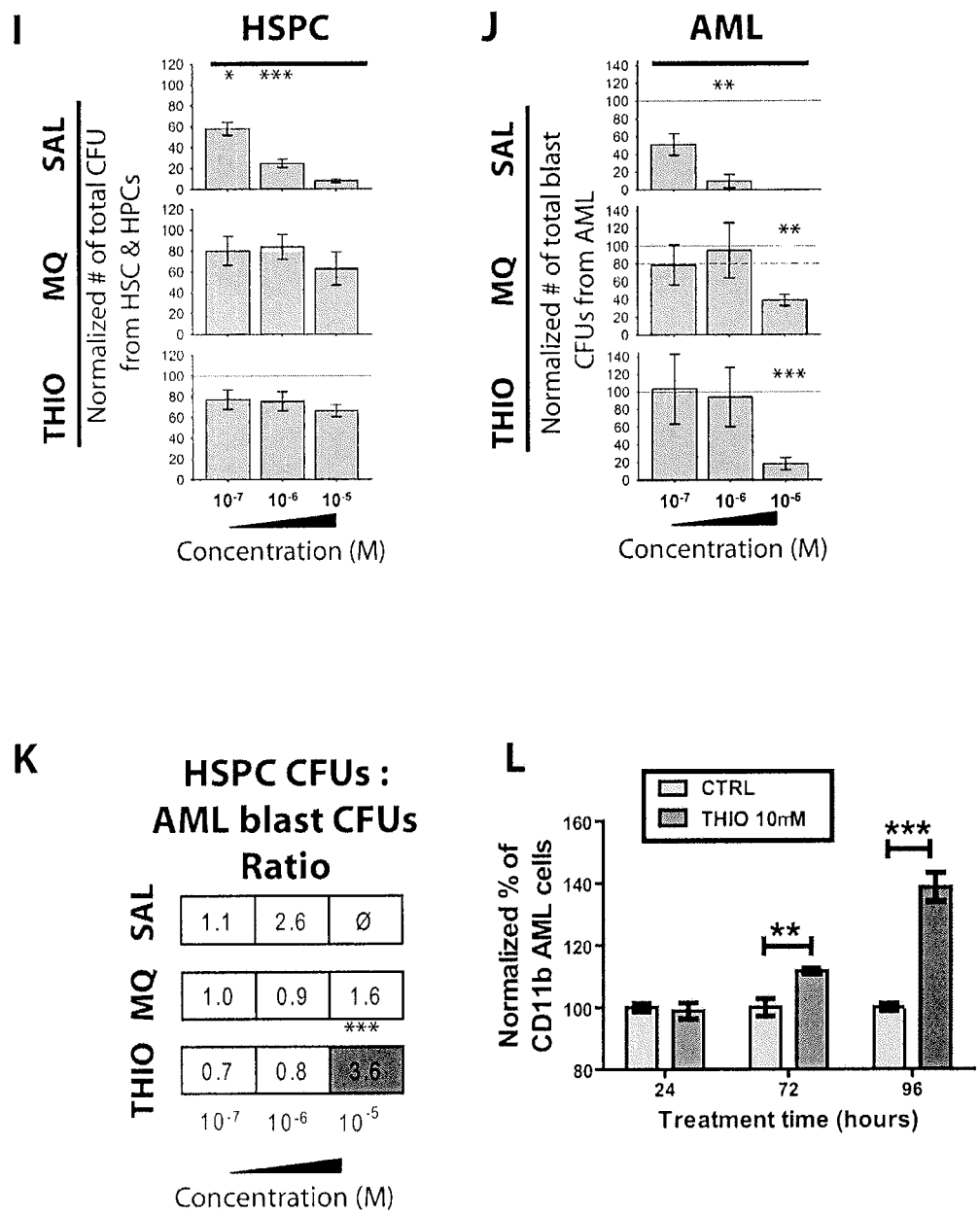
Figure 11:
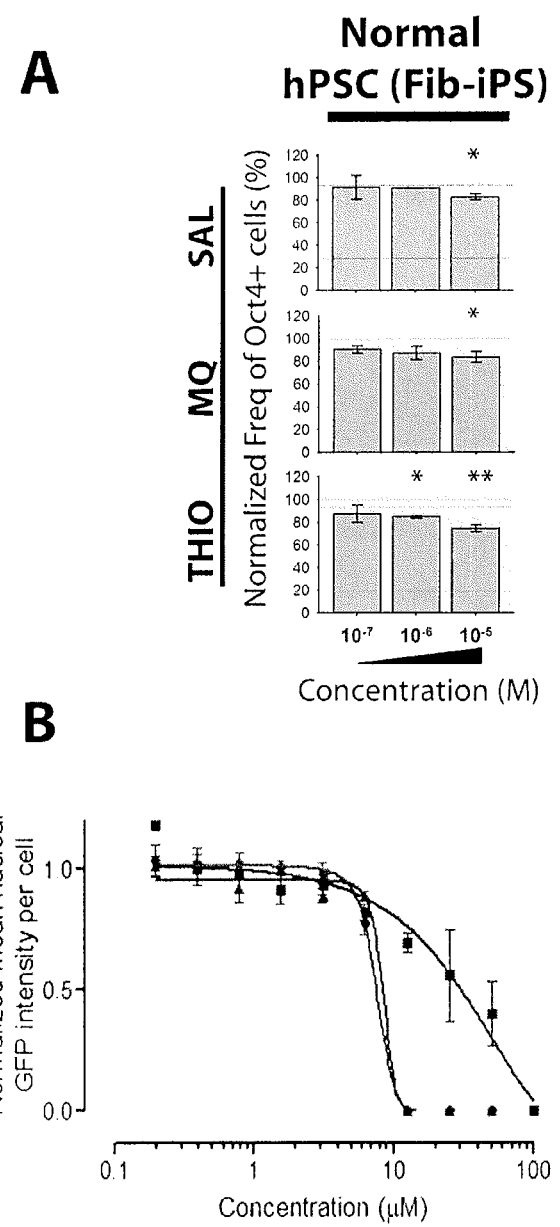
FIG. 11 shows the effect of salinomycin, mefloquine and thioridazine on fibroblast-derived iPSC and HSPC. (A) Flow cytometry analysis of frequency of Oct4+ cells in fibroblast-derived iPSC (Fib-iPS) treated with salinomycin (SAL), mefloquine (MQ) and thioridazine (THIO) at $10^{-7}$-$10^{-6}$ M. Each bar n=3; mean+/−SD. Values are normalized to DMSO-treated control samples; (−) DMSO mean, (−−) mean minus one SD, (−) level of % Oct4+ in BMP4 treated samples. (B) Extended dose response of compounds on neoplastic hPSC. Each point mean+/−SEM, (C) Hematopoietic lineage potential of CBlin− treated with thioridazine. Colony forming units (CFUs) of erythroblast (CFU-E), macrophage (CFU-M) and granulocyte (CFU-G) colonies generated in methylcellulose assays. (D) Composition of CFU generated from CBlin− treated with salinomycin, mefloquine and thioridazine. Percent composition of CFUs generated with salinomycin (SAL), mefloquine (MQ) and thioridazine (THIO) treatment at 0.1 µM, 1 µM and 10 µM. (*) p<0.05, (**) p<0.01
Figure 11:
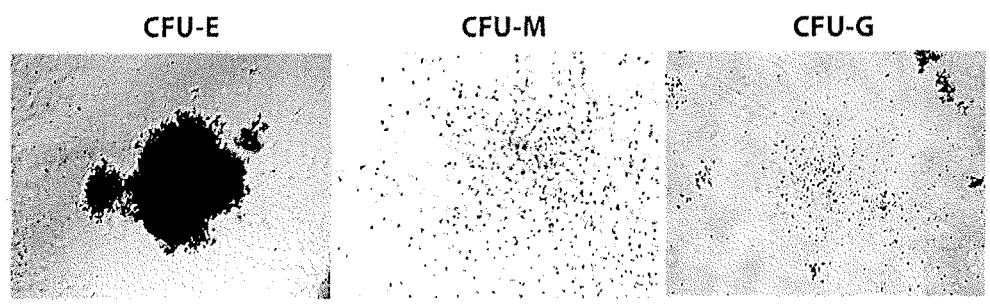
Figure 11:
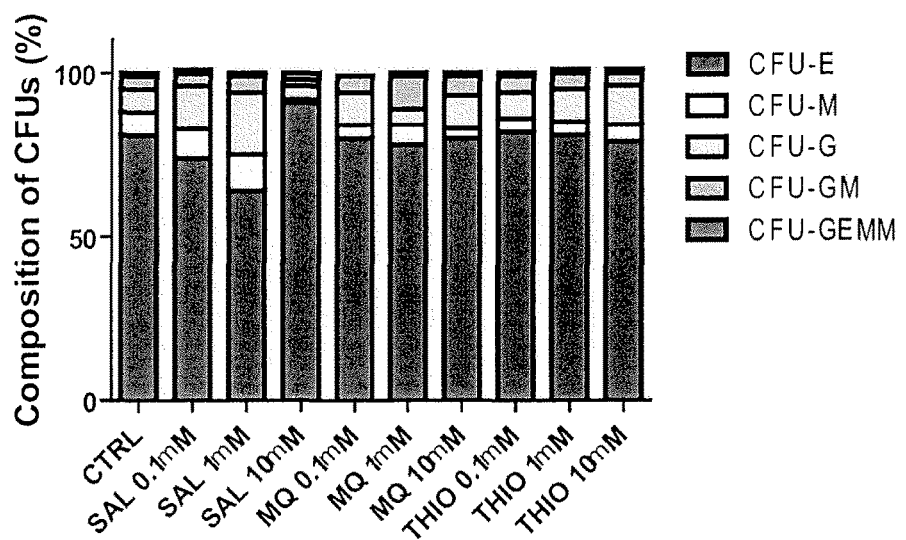

Thioridazine Selectively Induces Neoplastic hPSC Differentiation and Reduces Human AML Blasts without Affecting Normal Hematopoietic Stem/Progenitor Cells The responses to thioridazine and mefloquine were evaluated in both normal (FIG. 10a) and neoplastic hPSCs (FIG. 10b) at three concentrations using quantitative flow cytometry to detect the loss of Oct4 and reveal the degree of differentiation. Salinomycin, a reported selective inhibitor of breast CSCs (Gupta et al., 2009), was included for comparison. At 10 μM, all compounds reduced the number of cells, but the levels of Oct4 in remaining normal hPSCs was not below levels observed with BMP4 treatment (FIG. 10a). This same response was replicated in fibroblast-derived human iPS cells, (FIG. 11a), representing an additional normal hPSC line from a distinct (adult) origin, indicating the effects are not specific to embryonic sources. When the same compounds were used to treat neoplastic hPSCs, mefloquine and thioridazine treatments caused reductions in cell number and the levels of Oct4 in neoplastic hPSCs. Only thioridazine was able to reduce levels of Oct4 below BMP4 differentiation controls (FIG. 10b), indicating the ability of thioridazine to overcome neoplastic hPSC differentiation block. A more comprehensive dose response of all compounds was performed on neoplastic hPSCs to confirm this response (FIG. 11b). To identify compounds that selectively differentiate neoplastic hPSCs quantitatively, the ratio of normalized percentage of Oct4+ cells between normal and neoplastic hPSCs in response to these compounds was determined. For example, a ratio of 1 suggests equivalent differentiation whereas a ratio >1 defines relatively more differentiation in neoplastic hPSCs vs. normal hPSCs. Only thioridazine, at both 1 μM and 10 μM, had a significant impact on inducing differentiation of neoplastic hPSCs over normal hPSCs (FIG. 10c). Rapid accumulation of the cell stress marker p53 (FIG. 10d) and its transcriptional target p21 (FIG. 10e) were used to further distinguish differentiation induction from cellular toxicity. Treatment of neoplastic hPSCs with the toxic chemotherapeutic agent etoposide resulted in high levels of p53 and p21 after 24 h. However, treatment with 10 μM thioridazine or BMP4, unlike agents that induce toxicity alone, resulted in no accumulation of p53 or p21, consistent with induced differentiation rather than stress-response programs. Furthermore, thioridazine treatment led to expression of differentiation genes quantified by TaqMan Low-Density Array-qPCR in neoplastic hPSCs. An upregulation in 21 of 50 differentiation-associated genes (FIG. 10f) was observed in treated neoplastic hPSCs consistent with differentiation-inducing effects of thioridazine.

To examine the potential similarities in chemical response of neoplastic hPSCs to somatic CSCs, normal and neoplastic populations of the human hematopoietic system were assessed. Experimentally, self-renewal and differentiation of both human hematopoietic stem-progenitor cells (HSPCs) and Leukemic Stem Cells (LSCs) can be interrogated by powerful and well established in vitro and in vivo assays uniquely available to the hematopoietic system, making it an ideal tissue to evaluate the potential surrogacy of using normal and neoplastic hPSCs as a primary screening tool for anti-CSC compounds. Lineage-depleted umbilical cord blood (CB lin−) is highly enriched for HSPCs and is a reliable source of normal somatic SCs capable of self-renewal and multilineage differentiation to all blood lineages. Acute myeloid leukemia (AML) is a hematological neoplasia characterized by a block in mature myeloid differentiation that is sustained by a self-renewing LSC (Bonnet and Dick, 1997; Lapidot et al., 1994).

As such, progenitor assays in methylcellulose were conducted with HSPCs and 5 AML patient samples; each treated with thioridazine, mefloquine, or salinomycin in order to assess each compound's impact on in vitro clonogenic and multilineage hematopoietic differentiation. Representative cell pellets of the total colony-forming units (CFUs) generated from HSPCs (FIG. 10g) and AML (FIG. 10h) treated with each compound are shown. Thioridazine treatment resulted in a reduction in AML proliferation/clonogenic capacity while retaining HSPC multilineage differentiation (FIG. 11c). Changes in multilineage differentiation were quantified based on the enumeration of CFUs generated following treatment of HSPCs (FIG. 10i) and AML patient (FIG. 10j) samples with these compounds. At both 1 μM and 10 μM salinomycin reduced AML-blast CFU potential (FIG. 10j), but also reduced HSPC CFU potential over all doses tested (FIG. 10i) indicative of non-specific toxicity in the hematopoietic system. In contrast, mefloquine and thioridazine reduced AML-blast CFU formation (FIG. 10j) while having little effect on HSPC CFU potential (FIG. 10i) and multilineage composition (FIG. 11d) indicating that mefloquine and thioridazine do not alter normal hematopoiesis.

The most desired outcome of compounds identified toward clinical use would entail preferential elimination of AML-blast CFU generation while preserving normal HSPC progenitor capacity. The ratio between total CFUs generated from HSPC vs. AML-blasts to reveal the highest selectivity for targeting AML was calculated (FIG. 10k). A ratio of 1 suggests equivalent normal to neoplastic progenitor potential whereas a ratio >1 defines a compound that selectively reduces AML-blast CFU potential. Salinomycin (1 μM), mefloquine (10 μM), and thioridazine (10 μM) doses yielded the highest ratio values for each compound (FIG. 10k) and were thus selected for in vivo evaluation. Thioridazine 10 μM, in particular, demonstrated the highest ratio of all compounds, but most importantly was the only compound to show a significantly lower AML-blast CFU potential relative to normal HSPC CFU potential (FIG. 10k). To address whether thioridazine's specificity for reducing the clonogenic potential of AML-blast CFUs was due to induction of differentiation, the frequency of CD11b, a marker of granulocytic maturation, in patient AML cells was assayed in response to thioridazine treatment (FIG. 10l). A marked increase in the frequency of granulocytic AML-blast cells was observed with treatment duration (FIG. 10l) indicating that thioridazine exhibits its specific targeting of AML cells through induction of differentiation. This finding is analogous to differentiation-induction demonstrated in neoplastic hPSCs (FIG. 10a-f) and confirms the robust readout of this screening platform towards identifying agents able to differentiate neoplastic cells. This result also suggests that thioridazine may represent the best candidate for specific targeting of AML CSCs that requires testing using in vivo human-mouse xenograft assays.

Example 10

Thioridazine Reduces LSC Function while Sparing Normal HSPCs

Figure 12:
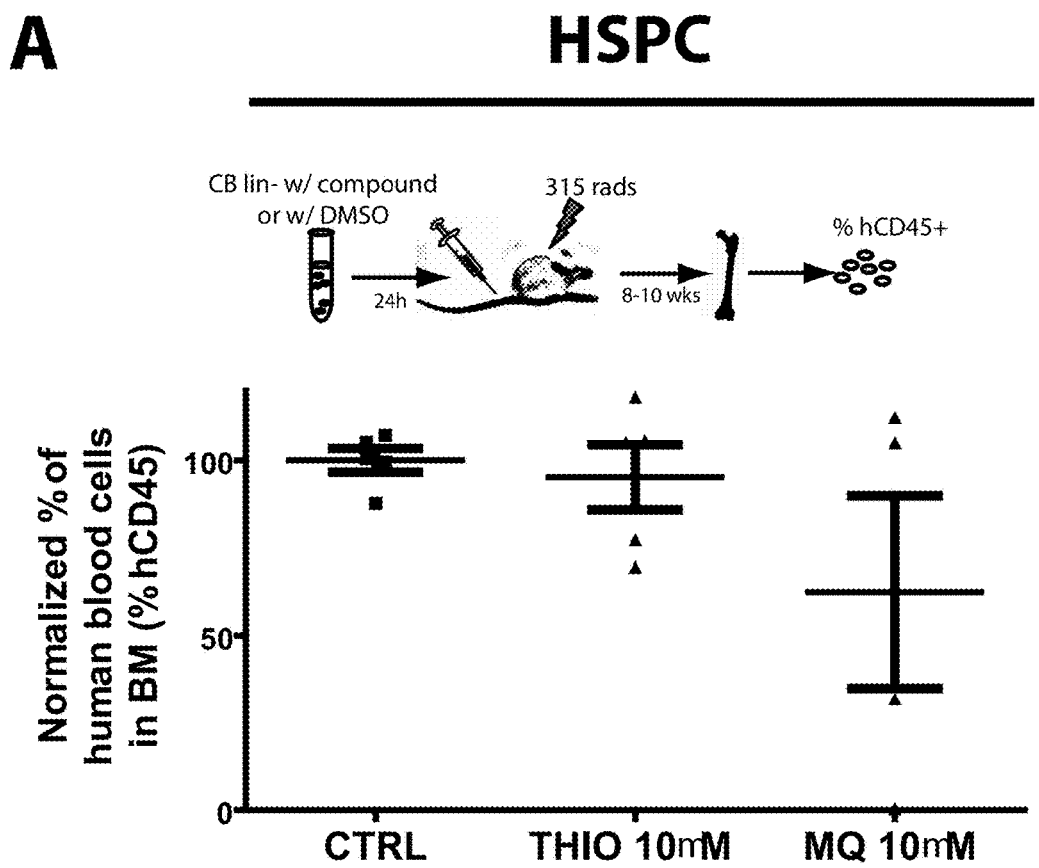
FIG. 12 shows thioridazine's effect on HSC and LSC engraftment. (A) Frequency of human CD45+ cells in the bone marrow following HSPC treatment with thioridazine 10 µM (THIO 10 µM) or mefloquine 10 µM (MQ 10 µM). Values normalized to DMSO-treated HSPC control (CTRL) samples. Total of two HSPC samples evaluated. Mean+/−SEM. (B) Representative flow cytometry plots of side scatter (SSC) versus myeloid (CD33) or lymphoid (CD19) markers within the hCD45+ population. 12(C) Frequency of CD45+ CD33+ AML blast cells in the bone marrow (BM) following treatment of AML with thioridazine 10 µM (THIO 10 µM) or mefloquine 10 µM (MQ 10 µM). Values normalized to DMSO-treated AML control (CTRL) samples. Total of two AML patient samples evaluated. (D) Representative flow plots of CD33 vs CD45 in DMSO-treated control (CTRL) populations versus thioridazine treated (THIO 10 µM). (E) Ratio of normalized percent hCD45 HSPC engraftment per normalized percent CD45 CD33 AML blast engraftment. (*) p<0.05
Figure 12:
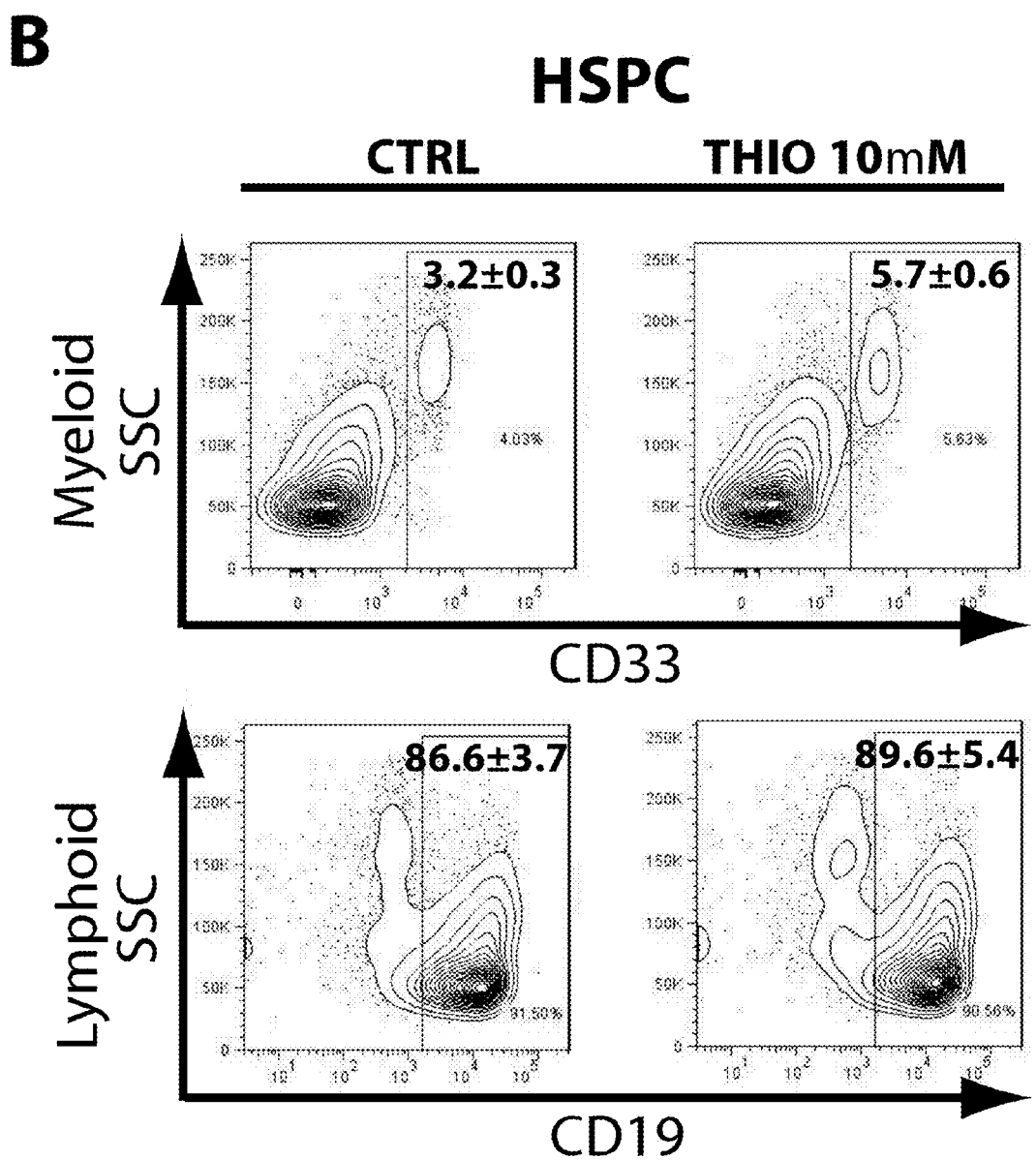
Figure 12:
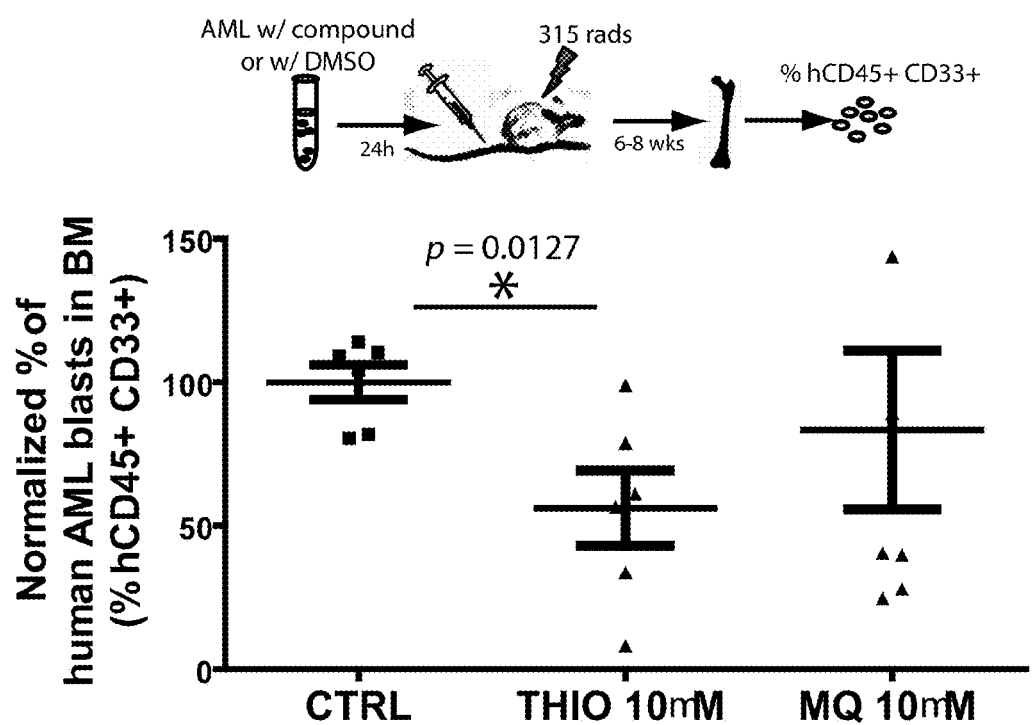
Figure 12:
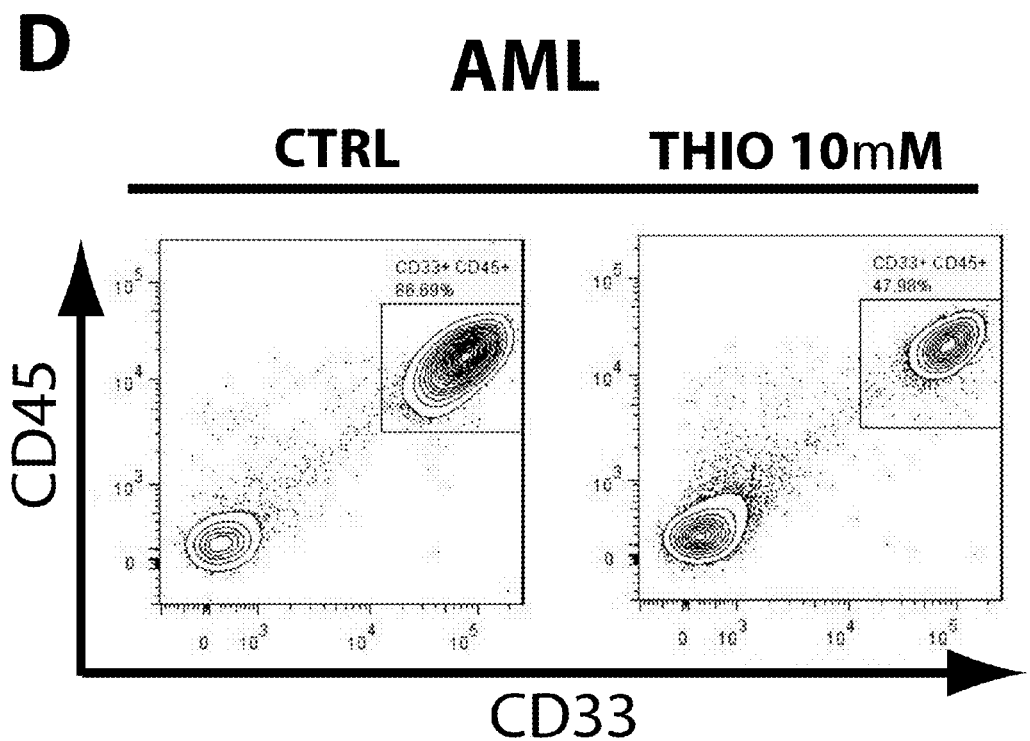

To delineate whether the inhibition of AML-blasts detected in vitro was due to the compounds affecting the neoplastic stem cell compartment, xenotransplantation studies (Dick, 2008) that functionally define LSCs and hematopoietic stem cells (HSCs) were conducted (FIG. 12). Treatment of HSPCs with salinomycin (1 µM) significantly reduced hematopoietic engraftment to almost non-detectable levels (FIG. 13a) revealing that this compound interferes with normal hematopoiesis from HSPCs and was thus excluded from further evaluation as it is unlikely to provide the selective anti-CSC therapeutic targeting desired. In contrast, mefloquine (10 µM) treatment displayed a slight, yet insignificant, reduction in HSC capacity relative to controls (FIG. 12a). However, mefloquine proved ineffective in reducing AML LSC capacity and was thus discontinued from further evaluation due to absence of selective effects (FIG. 12c).

Figure 13:
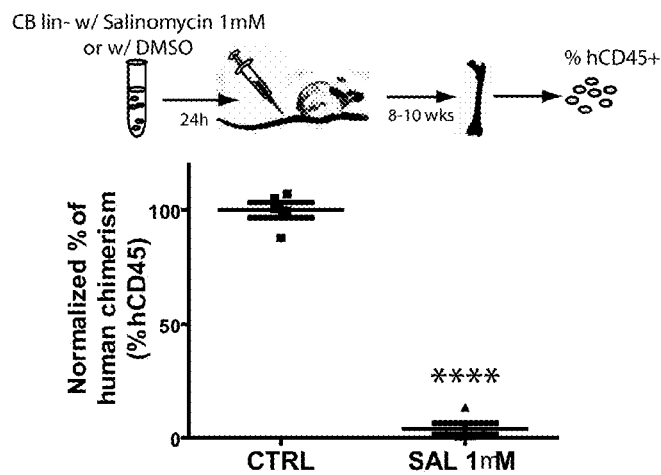
FIG. 13 shows in vivo response to drug treatment. (A) The normalized frequency of human CD45+ cells in the bone marrow following HSPC treatment with salinomycin 1 µM (SAL 1 µM) relative to DMSO-treated (CTRL) samples. Total of two HSPC samples evaluated. Mean+/−SEM. (****) p<0.0001 (B) Thioridazine's effect on HSC and LSC splenic engraftment. (B, top) Frequency of human CD45+ cells in the spleen following HSPC treatment with thioridazine 10 µM (THIO 10 µM). Values normalized to DMSO-treated HSPC control (CTRL) samples. Total of two HSPC samples evaluated. Mean+/−SEM. (B, bottom) CD45+ CD33+ blast cells in the spleen following thioridazine 10 µM (THIO 10 µM) treatment of AML. Values normalized to DMSO-treated AML control (CTRL) samples. Total of two AML patient samples evaluated. (C) Thioridazine's effect on erythrocytic and megakaryocytic regeneration. Composition of human blood cells detected in the xenotransplant BM injected with HSPC treated with thioridazine 10 µM (THIO 10 µM) or with DMSO (CTRL). Red blood cells (RBC) are defined by glycophorin A positivity and platelets by CD41a. (D) Confirmation of myeloid leukemic engraftment of xenotransplants with AML. Flow cytometry of side scatter versus CD19, a marker of lymphoid cells. Inset number represents mean+/−SEM. (E-F) Thioridazine's effect on HSC and LSC in vivo self-renewal. Engraftment levels of (E) hCD45+ cells or (F) hCD45+ CD33+ in BM of secondary xenotransplants receiving equal number of hCD45 cells explanted from (E) primary CBlin− or (F) primary AML transplants treated with thioridazine (THIO 10 µM) or DMSO control (CTRL). Each bar n=3 mice, mean+/−SEM.
Figure 13:
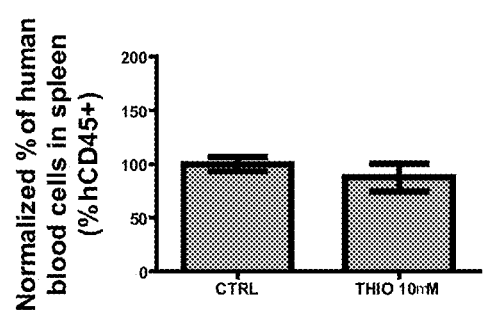
Figure 13:
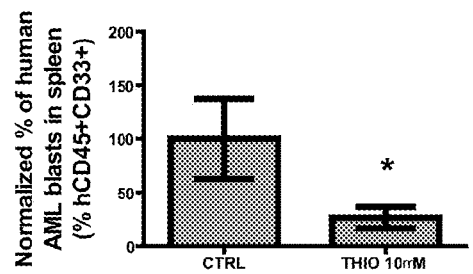
Figure 13:
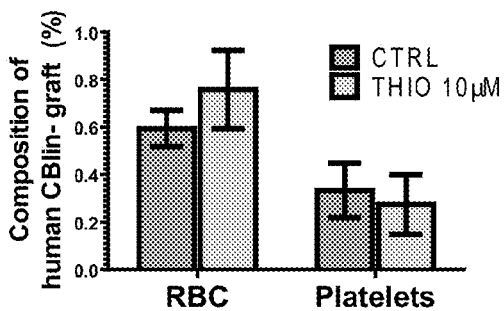
Figure 13:
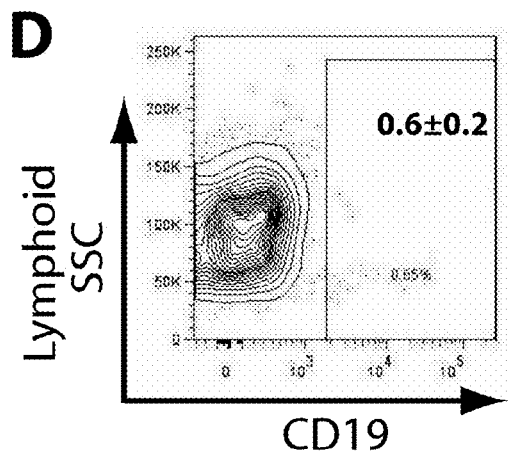
Figure 13:
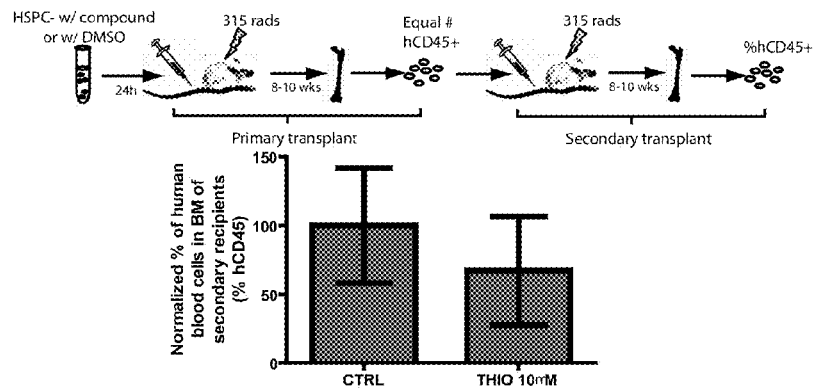
Figure 13:
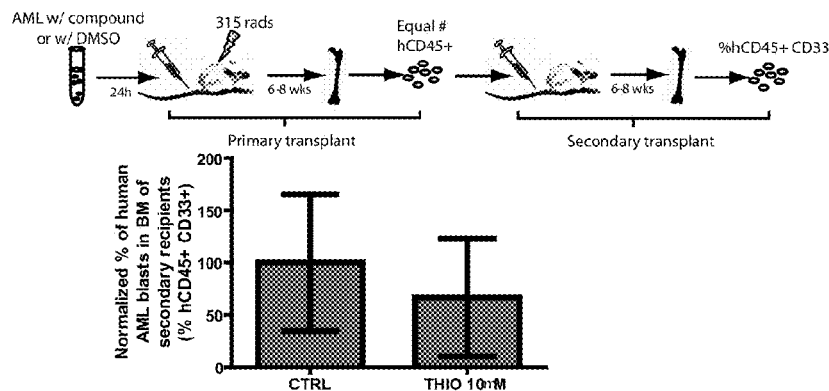

In contrast to both salinomycin and mefloquine, treatment of HSPCs with thioridazine 10 µM displayed the same level of bone marrow (BM) engraftment (FIG. 12a) and splenic engraftment (FIG. 13b) as control vehicle treated cells. Multilineage reconstitution capacity was identical from control- and thioridazine-treated human HSCs with myeloid (FIG. 12b), lymphoid (FIG. 12b), erythroid (FIG. 13d), and megakaryocytic development (FIG. 13d) completely unaffected. As measured by secondary serial transplantation, thioridazine treatment did not affect HSC self-renewal as compared to control-treated samples (FIG. 13f). However, in sharp contrast to salinomycin and mefloquine, thioridazine treatment was able to significantly reduce leukemic disease-initiating AML LSCs (FIGS. 12c-d; FIG. 13c; FIG. 13e). Calculating the ratio of HSPC normal hematopoietic regeneration (% hCD45+) to AML leukemogenesis (% CD33+ hCD45+ blasts) revealed that thioridazine significantly reduced LSC function while preserving normal HSC capacity (FIG. 12e). In the absence of thioridazine, no difference in the level of leukemic engraftment of secondary transplant recipients was observed. This suggests that continued exposure to this drug is necessary to inhibit leukemogenesis in secondary recipients. These data demonstrate that thioridazine selectively targets somatic CSCs whilst having no effect on normal SC properties in vivo. As thioridazine was identified through the use of a novel differential screening platform using normal and neoplastic hPSCs in vitro, the functional effects of thioridazine provide an example of the predictive value of using human PSCs to understand somatic CSCs.

Example 11

Dopamine Receptors Demarcate Human CSCs

Figure 14:
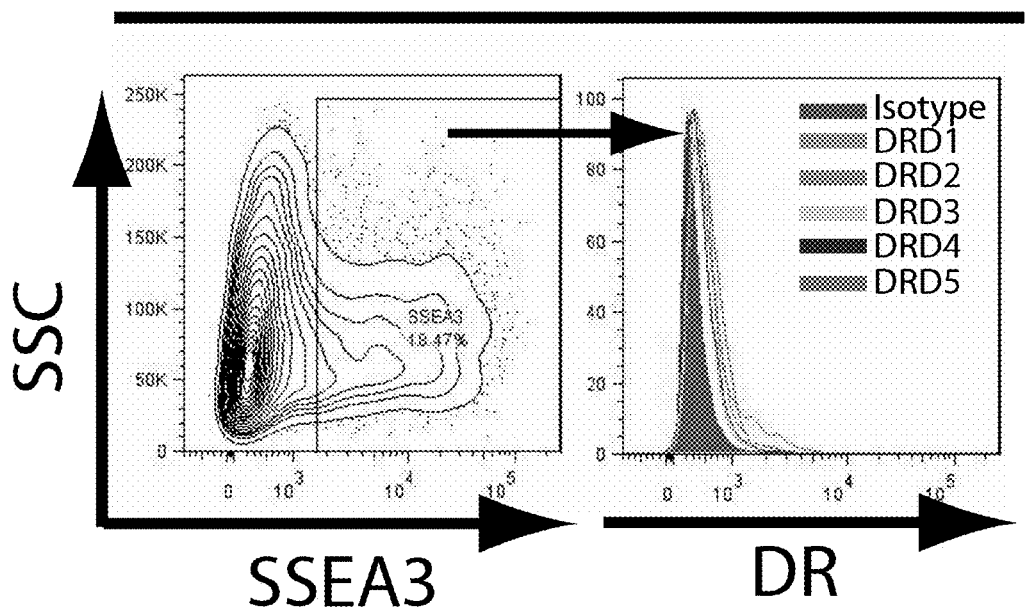
FIG. 14 shows dopamine receptors expressed on neoplastic stem cells. (A-B) Flow cytometry of (A) normal H9 and (B) neoplastic v1H9-Oct4-GFP cells stained with SSEA3 and all five dopamine receptor (DR) subtypes. DR expression in the SSEA3+ fraction is shown. (C) Flow cytometry of lineage-depleted cord blood (HSPC) stained with CD34, CD38 and all five DR subtypes. DR expression is presented in the gated populations. (D) Flow cytometry of 13 AML patient samples stained for all five DRs along with associated FAB classification. (E) Co-localization of DRD5 in triple-negative (ER−, PR− and HER2−) primary human breast tumor stained with CD44 and CD24. (F) The frequency of triple-negative breast CSC (CD44+CD24−/$^{lo}$) within the DRD3 and DRD5 population. Each bar composed of 3 primary triple-negative breast tumors, mean+/−SEM. (G-H) Frequency of AML blast cells (CD33+CD45+) from patient samples which are also positive for (G) DRD3 and (H) DRD5. A total of 8 AML patient samples were assessed for leukemic-initiation potential in xenotransplantation recipients. Leukemic-initiating was defined as human engraftment >0.1% of CD33+ hCD45+ in mouse bone marrow. Four leukemic-initiating AML samples were assayed in 22 mice while 4 non-initiating AML samples were assayed in 17 mice. Total n=8 AML samples, mean+/− SEM.
Figure 14:
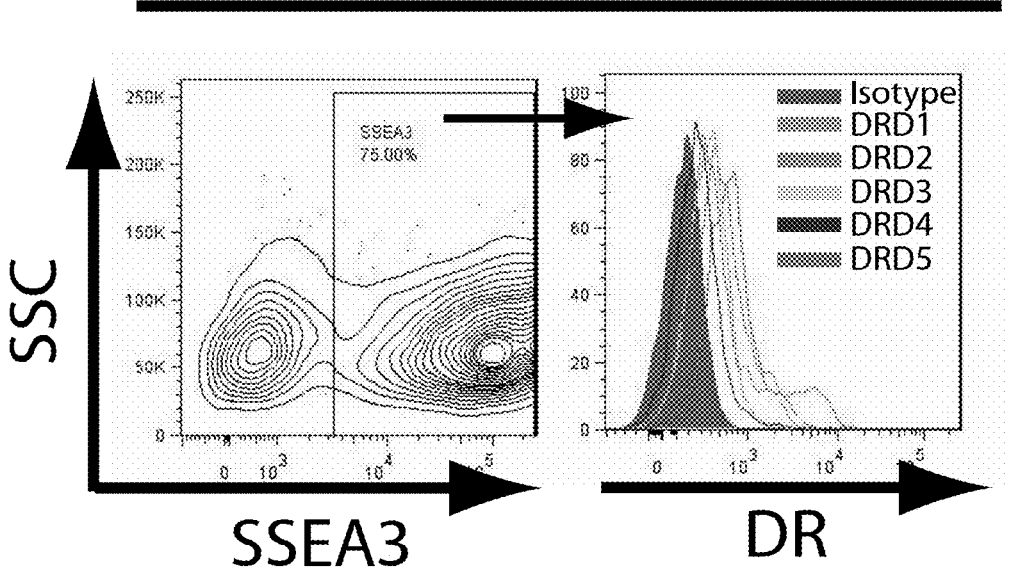
Figure 14:
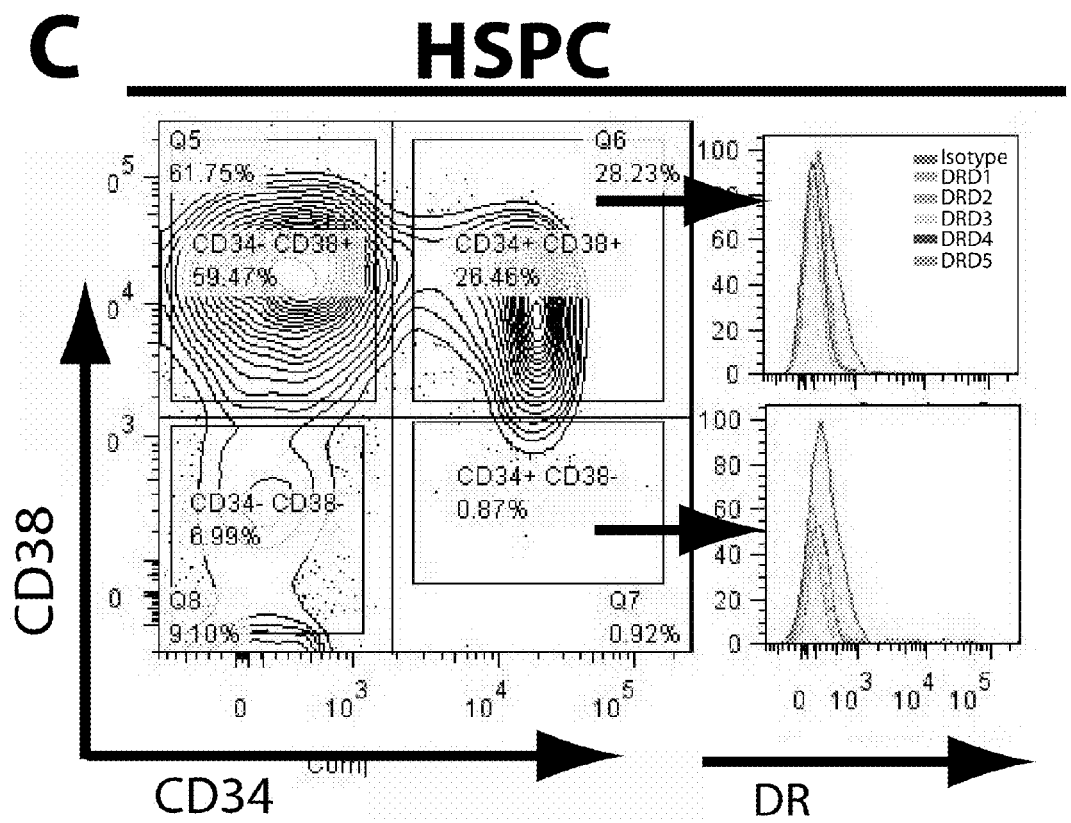
Figure 15:
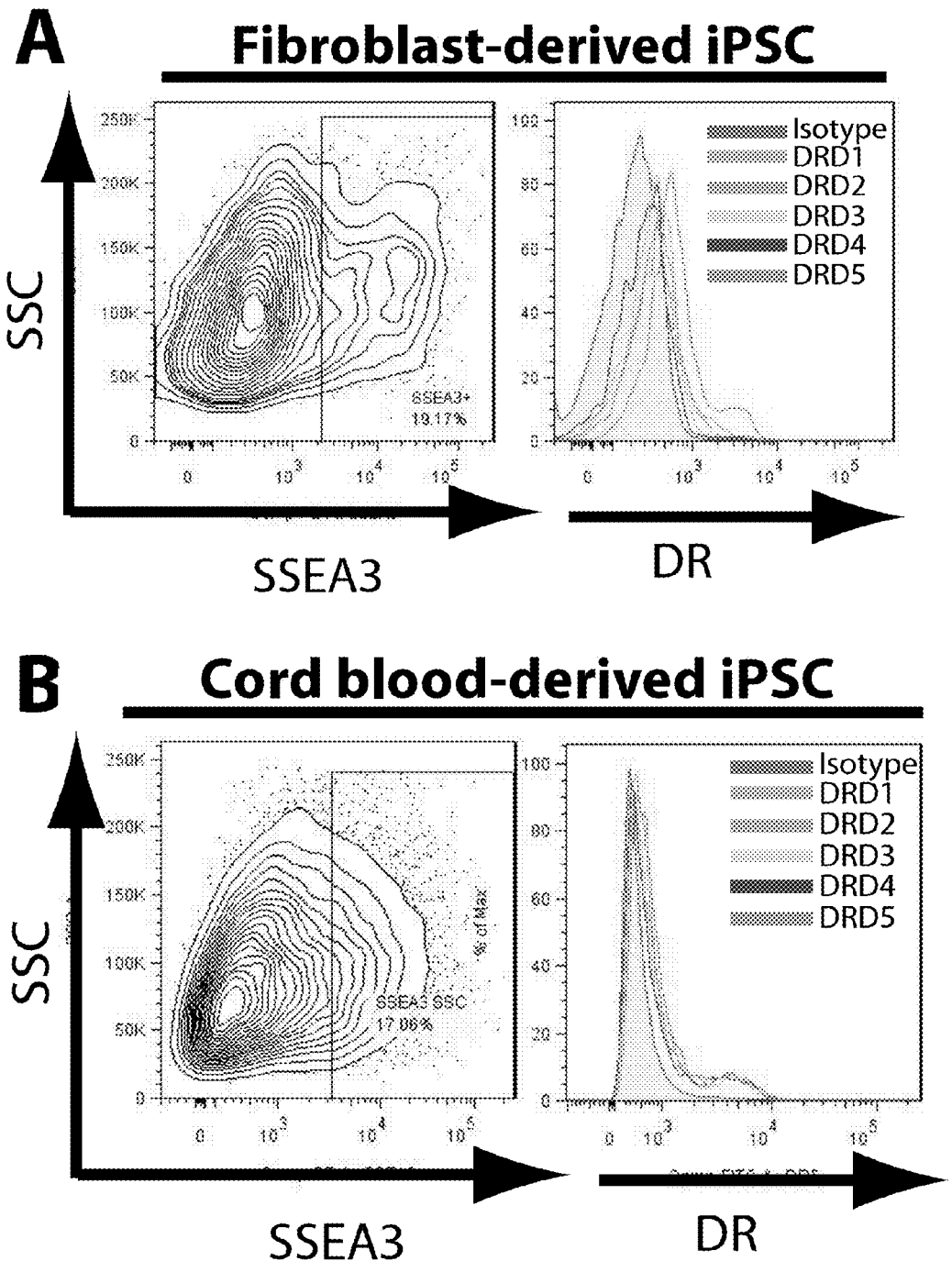
FIG. 15 (A-B) Flow cytometry SSEA3+ fraction in (A) fibroblast-derived hiPSC and (B) umbilical cord blood-derived hiPSC stained for all five dopamine receptors. (C) Dopamine receptors expression of human blood populations. Flow cytometry of cord blood mononuclear cells stained for (C) erythroid (glycophorin A), (C) megakaryocytes (CD41a); (D) T-cells (CD3), (D) B-cells (CD19); (E) monocytes (CD14) and (E) granulocytes (CD15). Staining for all five DRs in the gated populations are shown as histograms. (F) Summary of DR localization in the blood populations. (G) Flow cytometry of AML patient showing DR in gated populations. (H) Dopamine receptor expression in triple-negative human breast tumors. Breast CSC are defined as CD44+ CD24−/$^{lo}$ (Al-Hajj et al., 2003). Co-localization of each DR within the CD44 and CD24 population is shown for three triple-negative (ER−, PR− and HER2−) breast tumors.
Figure 15:
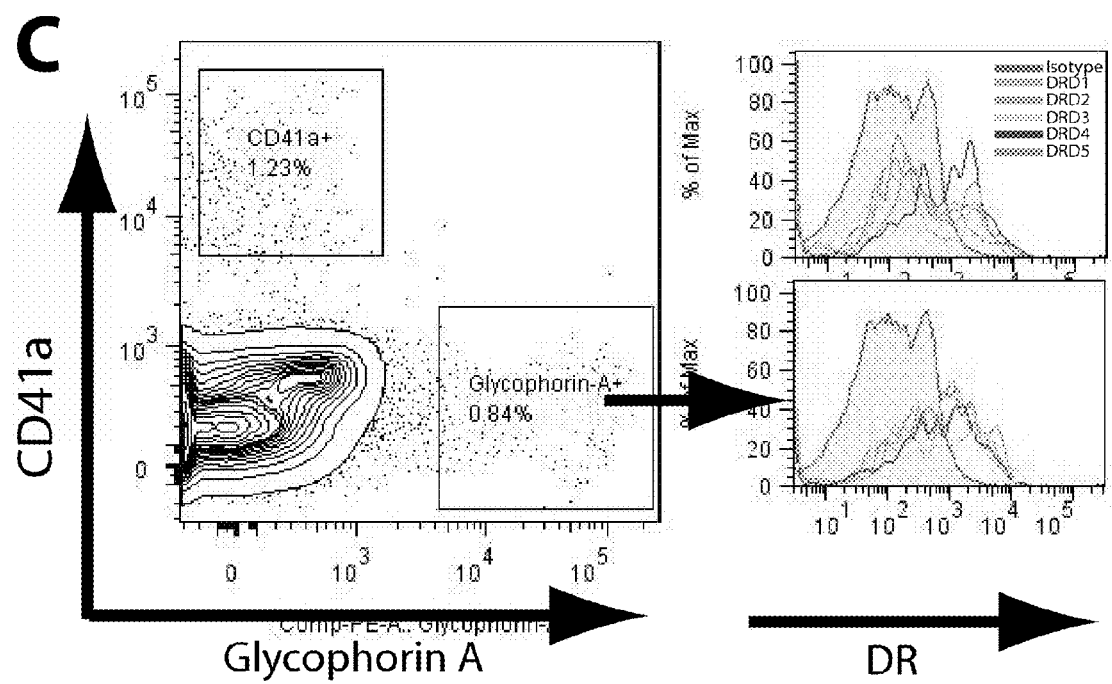
Figure 15:
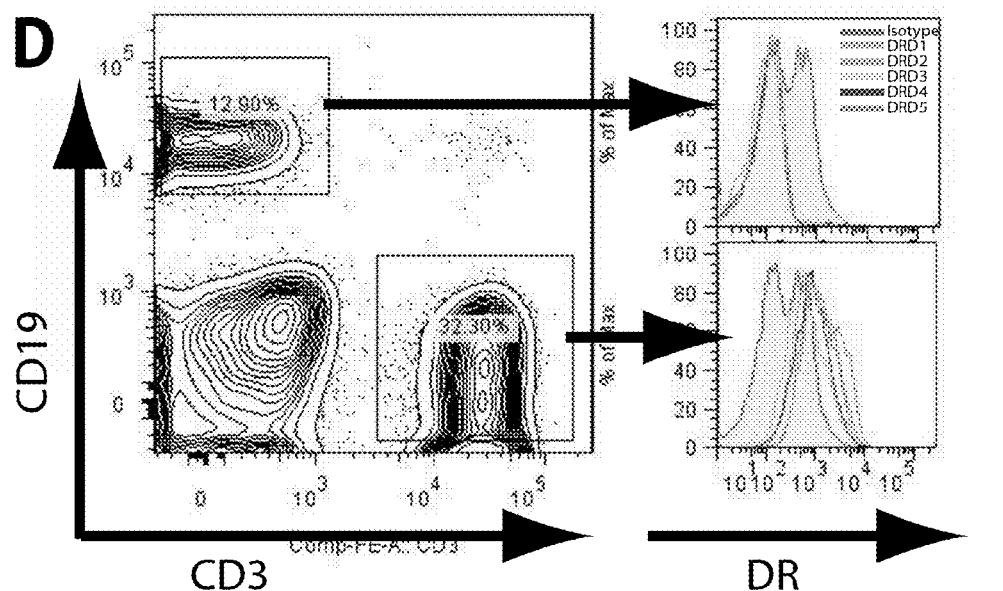
Figure 15:
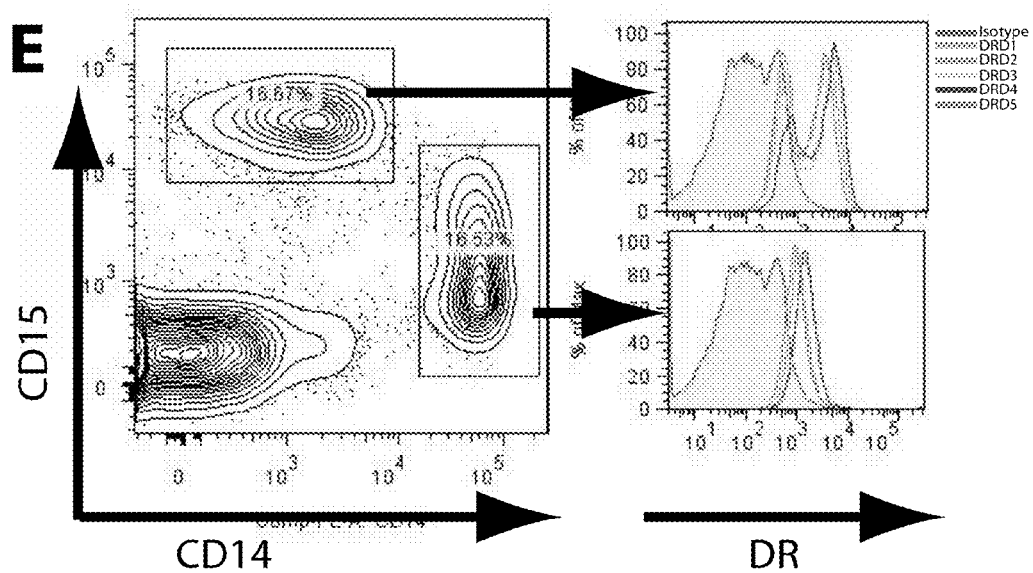
Figure 15:
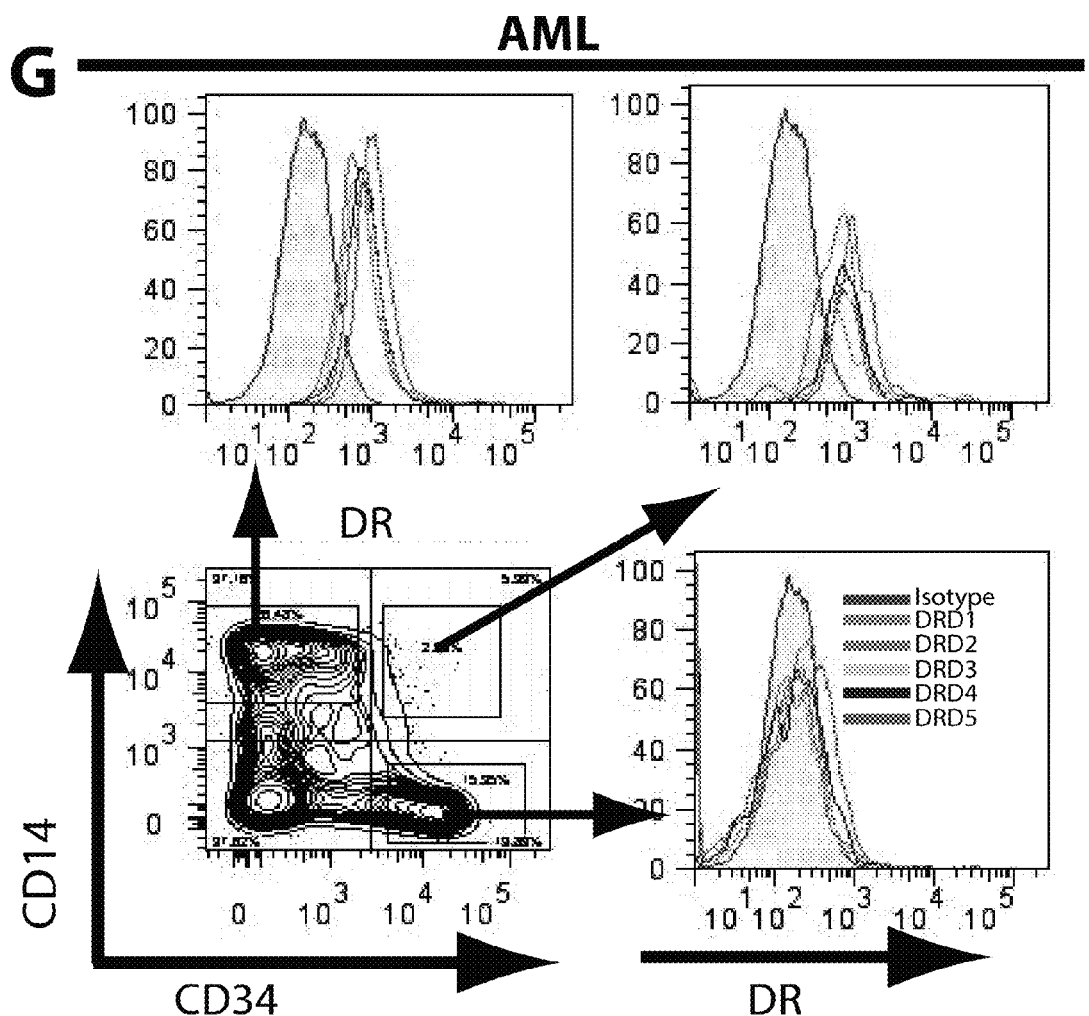
Figure 15:
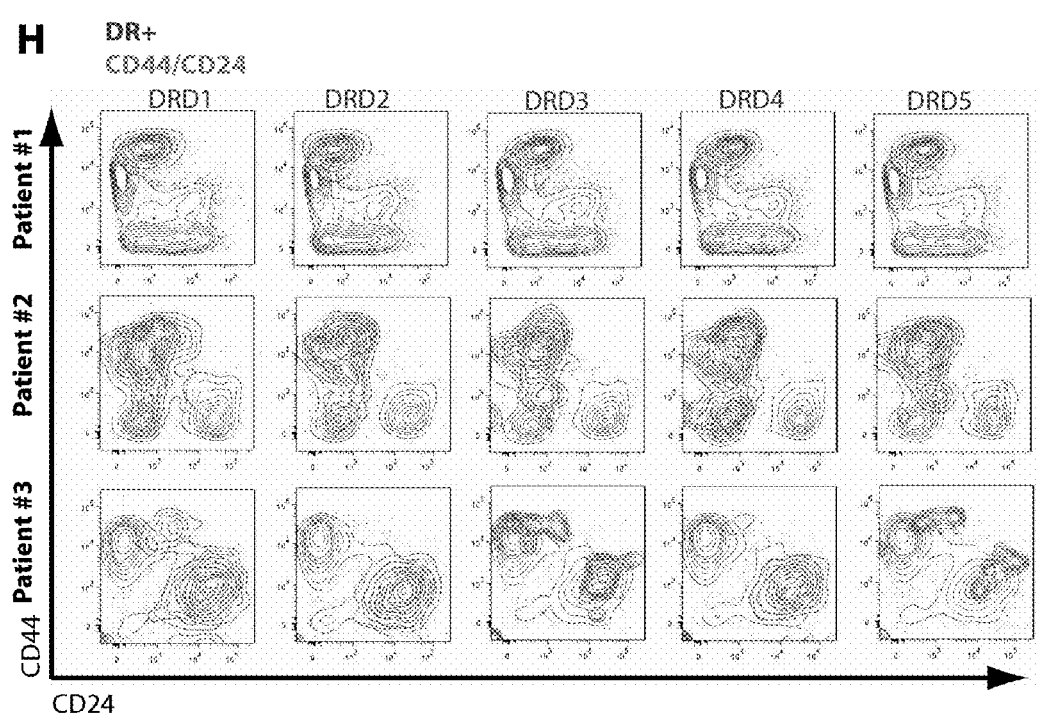

Thioridazine is known to act through the dopamine receptors (DR 1-5) (Beaulieu and Gainetdinov, 2011; Seeman and Lee, 1975). To assess whether the mechanism of thioridazine action to selectively interfere with human CSCs vs. normal SCs is via DR antagonism, DR cell surface expression was analyzed. To date, five DRs have been identified and divided into $D_1$-family (D1 and D5) and $D_2$-family (D2, D3, and D4) receptors (Sibley and Monsma, 1992). Normal hPSCs expressing the pluripotent marker SSEA3 were devoid of DR expression (FIG. 14a and FIG. 15a-b). In contrast, neoplastic hPSCs expressed all five DRs (FIG. 14b). The observed differential expression of DRs and the selective inhibition of thioridazine for neoplastic hPSCs suggest that inhibition of DR signaling may play a role in selective targeting of human CSCs vs. normal SCs.

To expand the potential role of DRs in CSCs based on the functional role of thioridazine treatment we examined whether DR antagonism could account for the loss of LSC function following thioridazine treatment. Expression of DR1-5 was analyzed in HSPCs (FIG. 14c) and human hematopoietic mononuclear cells from normal CB (FIGS. 15c-f) and AML patient samples (FIG. 14d and FIG. 15g). DRs were not observed in the primitive HSCs or progenitor populations of CB (identified as the CD34+38− or CD34+38+ fractions, respectively (Bhatia et al., 1997)) (FIG. 14c) indicating that HSCs and progenitors do not express the targets for thioridazine. Similarly, DRs were undetectable on the surface of erythroid (FIG. 15c), megakaryocytic (FIG. 15c), and lymphoid cells (FIG. 15d). Only monocytes defined as CD14+ and approximately half the population of granulocytes defined as CD15+ expressed DRs (FIGS. 15e-f). All of the 13 AML patient samples analyzed contained a population of DR+ blasts with varying levels of all five receptors (FIG. 14d) and were predominately detected in CD34+/CD14+ cells (FIG. 15g). However, unlike normal HSCs, CD34+ cells do not correlate with LSC capacity in human AML (Taussig et al., 2008) and have recently been identified in numerous subfractions devoid of CD34 or CD38 (Eppert et al., 2011). Observations of differential DR expression in normal and AML human hematopoietic samples strongly suggest the human AML LSCs are heterogeneous and drug targeting should be based on molecular pathways instead of surrogate phenotype predications.

Aside from hematopoietic tissue, somatic CSCs have recently been identified and validated in human breast tumors and have a CD44+CD24−/lo phenotype (Al-Hajj et al., 2003). Using primary human breast tumors which test negative for estrogen receptor (ER−), progesterone receptor (PR−), and human epidermal receptor 2 (HER2−) that are associated with the poorest prognostic outcomes (Dent et al., 2007) we reveal DR colocalization on the CD44+CD24−/lo breast CSCs (n=3 patients) (FIGS. 14e-f and FIG. 15h). This finding is consistent with the low levels of DRs found in normal mammary gland tissue, whereas benign breast tumors show intermediate levels and breast cancers display high levels of these receptors (Carlo, 1986). Whether the DR expression in AML-blasts was correlative to incidence of LSCs in AML patients was investigated. AML samples with a large fraction of DRD3+ blasts (FIG. 14g) and DRD5+ blasts (FIG. 14h) contain LSCs as they are able to initiate leukemia in xenotransplantation recipients, unlike AML patient samples with significantly lower levels of DRs that do not contain LSCs. Samples from AML patients containing LSCs have been correlated to poor prognostic outcome while non-LSC samples demonstrate a good prognosis (Eppert et al., 2011). High levels of DR expression correlate with poor prognosis while low levels demonstrate good prognosis (FIG. 14g-h) suggesting that DR assessment has prognostic biomarker applications and is less complex than molecular signatures or LSC readouts for each AML patient. Based on initial identification in neoplastic hPSCs, these collective results suggest a potentially more generalizable role for DR expression in human somatic CSCs than anticipated, and validate DR as a candidate biomarker for other CSCs in the human.

Example 12

Thioridazine Antagonism of DR Inhibits Human AML

Figure 16:
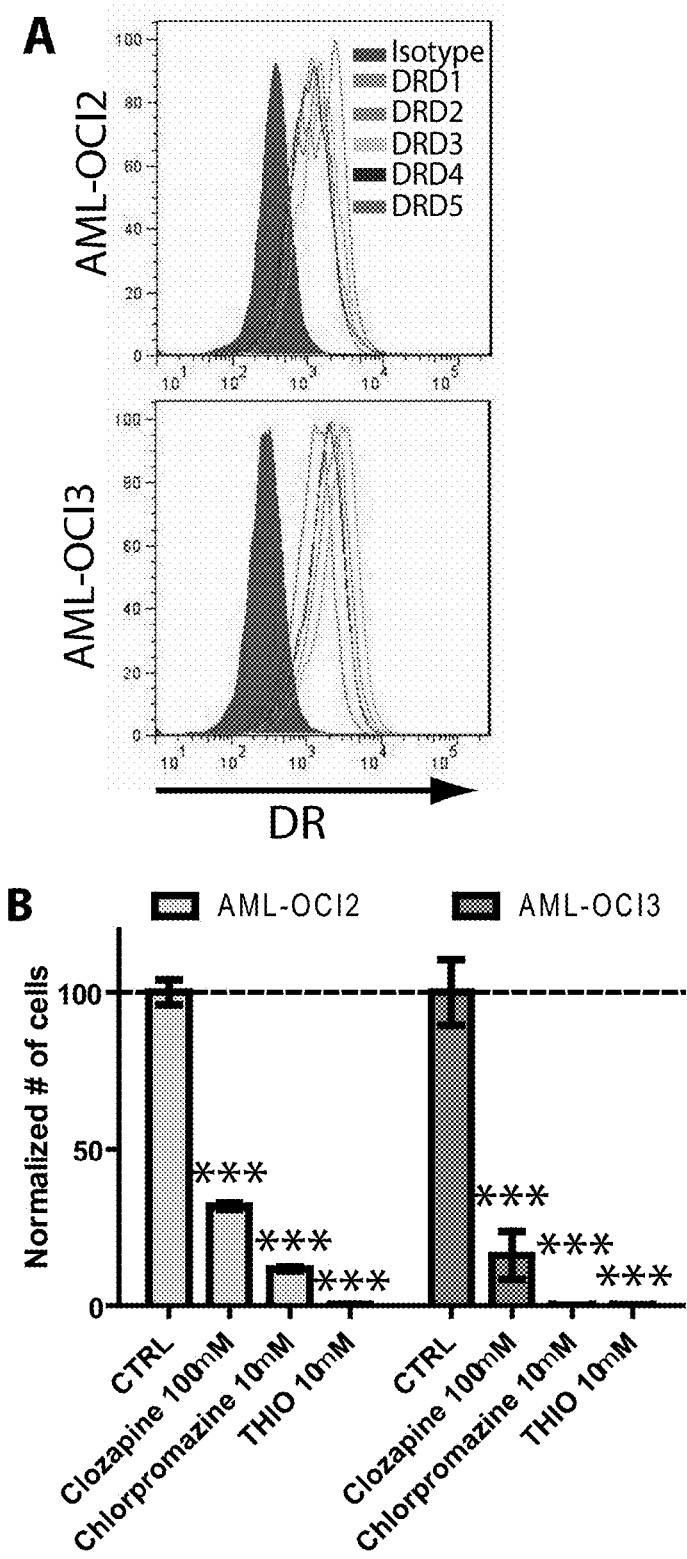
FIG. 16 shows that thioridazine inhibits dopamine receptor signalling in AML. (A) DR expression of AML-OCI2 and AML-OCI3 cell lines. (B) Cell counts of AML-OCI2 and AML-OCI3 cells treated with three DR antagonist drugs. Values are normalized to DMSO-treated control samples. Each bar n=3; mean+/−SD. (C-D) Viable cell counts (7AAD−, Hoechst+) of same cell lines treated with (C) 7OH-DPAT, a DR D2-family agonist, or (D) SKF38393, a DR D1-family agonist, in serum-free conditions. Values are normalized to DMSO-treated control samples. Each bar n=3; mean+/−SD.
Figure 16:
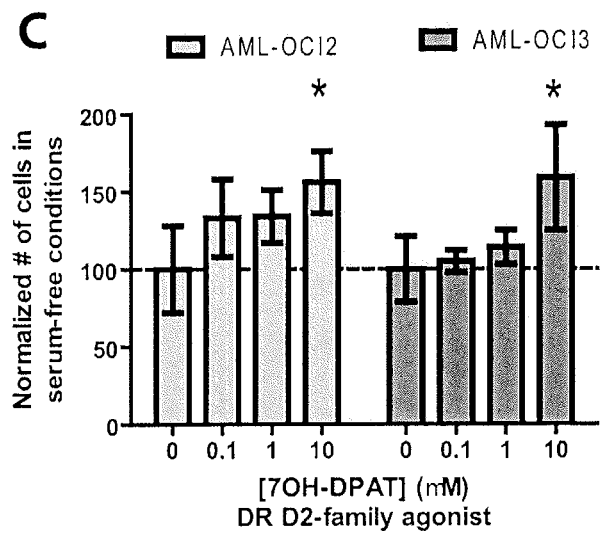
Figure 16:
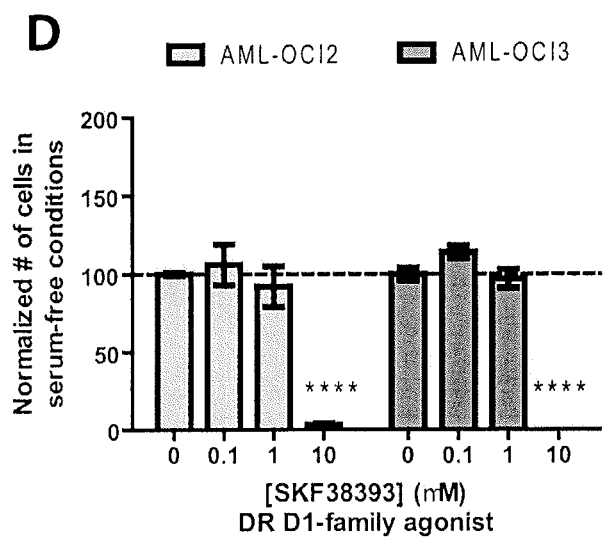

To better understand the functional role of DR in human AML, two AML cell lines derived from patients; AML-OCI2 and AML-OCI3, were utilized (Koistinen et al., 2001). Like primary samples, these two cell lines revealed expression for each DR1-5 (FIG. 16a) at markedly higher levels than seen in patient samples. Due to the bioavailability of dopamine in fetal bovine serum (FBS) (Little et al., 2002), serum-free conditions were employed to assess the role of DRs in AML. Both AML lines were treated with thioridazine and compared to other known DR antagonists clozapine and chlorpromazine (Seeman and Lee, 1975). All three DR antagonists reduced the number of AML cells upon treatment (FIG. 16b). To further evaluate the specificity of DR targeting on human AML cells, patient AML samples were divided into DR+ and DR- subfractions using fluorescence activated cell sorting before being treated with DMSO vehicle or thioridazine for 24 h and then assayed for blast-CFU content. A reduction in blast-CFU generation was only observed in the DR+ subfraction treated with thioridazine (FIG. 17a) whereas no reduction was observed in DR- subfraction treated with thioridazine (FIG. 17b). Conversely, the addition of a DR D2-family agonist, 7OH-DPAT, increased the number of AML cells (FIG. 16c). DR D2-family and D1-family exert opposing actions on intracellular signaling leading to differential biological effects (Self et al., 1996). Treatment with a DR D1-family agonist, SKF38393, resulted in a significant reduction in AML cell number confirming that D2-family signaling is necessary for AML cell survival (FIG. 16d). These combined results suggest the mechanism of thioridazine's action is through antagonism of D2-family DRs and not due to off-target effects, and identifies a novel avenue of CSC targeting via DR signaling.

Example 13

Thioridazine-Analogs as Anti-Cancer Stem Cell Agents

Figure 17:
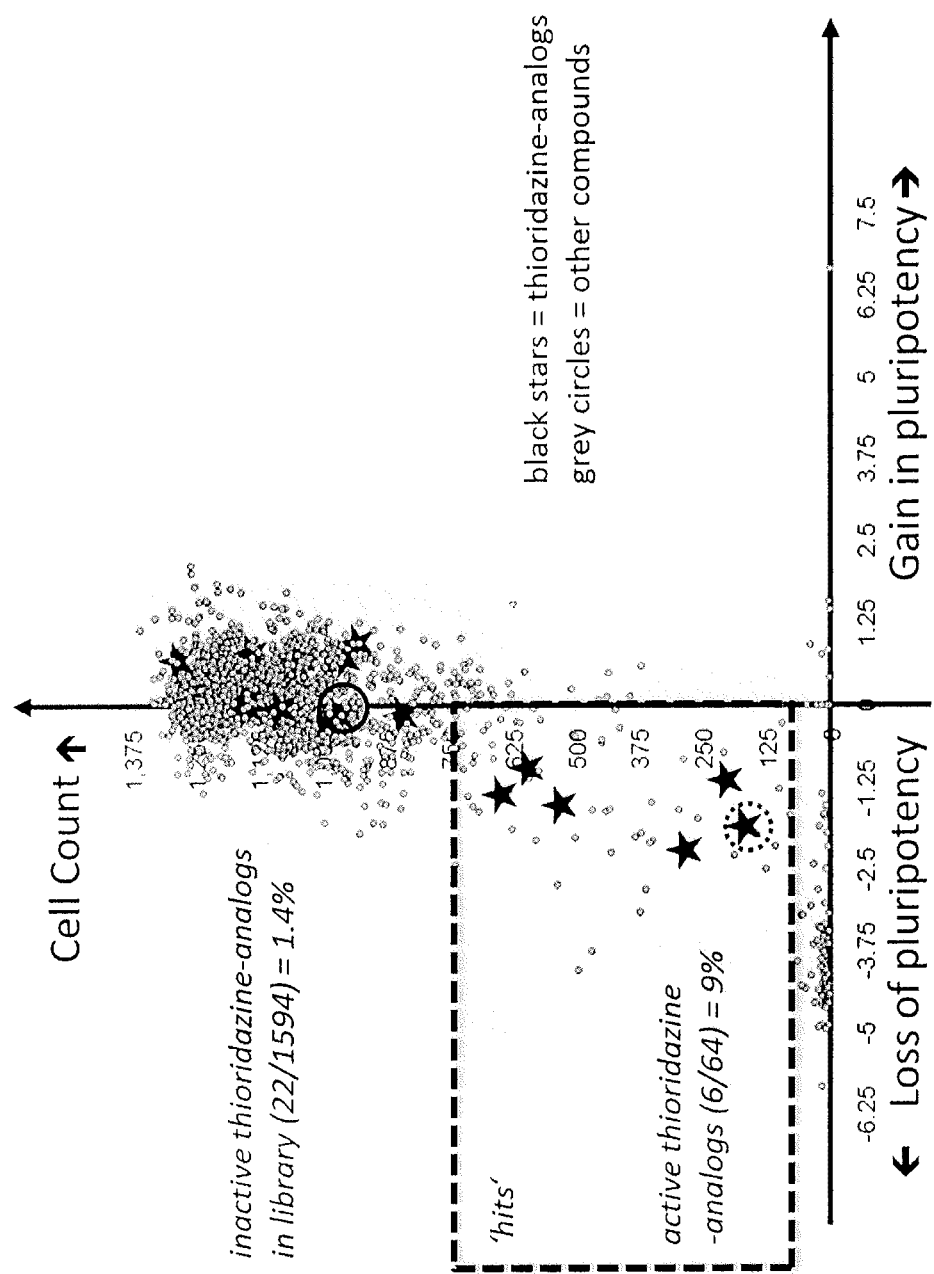
FIG. 17 shows a scatter plot of cell counts versus changes in pluripotency of v1O4 cells treated with compounds from chemical libraries. Thioridazine is represented by the black star in the dotted circle while thioridazine-analogs are the black stars in the dotted box. Chlorpromazine is identified as the black star in the solid circle. Thioridazine-analogs (compounds with thioridazine-like structure) are disproportionately represented as hits, i.e. causing a relative loss in cell count and a loss of pluripotency in variant neoplastic stem cells.

FIG. 17 shows a scatter plot of variant neoplastic stem cells (v1O4 cells, v1H9-Oct4-GFP cells) treated with different chemical libraries to identify active compounds or 'hits'. Compounds were classified as hits if they induced a loss of pluripotency (LOP, a measure based on detection of a reporter of Oct4 levels, which in this instance is a GFP signal output) and a reduction in cell counts (below 750 cells per acquired image). Compounds that reduced cell counts below 100 were classified as highly toxic and not considered as useful.

Briefly, v1O4 cells were seeded into Matrigel-coated 96 well plates (5000 cells/well) containing mouse embryonic fibroblast conditioned media (MEFCM) supplemented with 8 ng/mL bFGF, and treated for 72 hours with compounds dissolved in DMSO. The final concentration of each compound used in treatment was either 10 μM or 1 μM (n=3). Control wells were treated with 0.1% DMSO (low control) or 100 ng/ml BMP4 (high control to induce LOP). At the end of 72 hours, cells were fixed, stained with Hoechst and imaged by automated microscopy. GFP intensity and Hoechst signal were quantified as measures of LOP and cell count, respectively, and compounds with a Z-score of more than 3 standard deviations from the mean for reduced cell count and LOP were chosen as hits.

Thioridazine was identified as a hit (Figure A, star in dotted circle) as well as six other compounds with similar chemical structures (thioridazine-analogs) (Figure A, stars in dotted box). The thioridazine-analogs identified as hits included prochlorperazine, trifluoperazine, fluphenazine, perphenazine, and triflupromazine. Structural similarity of the analogs was determined based on these compounds having a Tanimoto coefficient of similarity >0.6 when compared with thioridazine (as calculated by IDBS SARView software). Surprisingly, the thioridazine-analogs were disproportionately represented as hits (6/64=9%) compared with a total frequency of thioridazine analogs present in all of the chemical libraries (22/1594=1.4%), a greater than six-fold difference. This suggested a structural feature present in thioridazine and related compounds causes a reduction in cell number and LOP in neoplastic cancer stem cells.

The phenothiazine-related compound chlorpromazine is cytotoxic to several leukemia cell lines—as well as other types of cancer cell lines—with a potency comparable to thioridazine. However, chlorpromazine did not have a comparable effect on v1O4 cells (FIG. 17, circled star). Accordingly, the effect of chlorpromazine is dependent on the cell to which it is exposed and that having some anti-cancer properties do not necessarily imply having broad activity against all cancer cells or cancer stem cells.

Example 14

Thioridazine Analogs with Activity in Variant Neoplastic Stem Cells do not Induce Cell Death in AML Cancer Cell Lines Cancer cell lines have been used in high-throughput screening assays for identifying potential anti-cancer therapeutics. Cell viability is a commonly used output for assaying the potential anti-cancer activity of a compound. However, cancer therapeutics that rely solely on induction of cell death may not represent the most effective method for eradicating cancer stem cells. Identification of compounds that specifically target cancer stem cells and induce their differentiation could represent another type of targeted therapy. The difficulty in identifying these types of compounds is due in part to a lack of appropriate surrogates for cancer stem cells. Based on the characterized features and properties of variant neoplastic stem cells, they are useful for identifying anti-cancer compounds that are not necessarily inducing cell death.

Two observations demonstrate the utility of variant neoplastic stem cells in identifying compounds that were or were not identified as anti-cancer compounds by other systems. Both observations are related to the response of AML cancer cell lines AML-OCI2 and AML-OCI3 to thioridazine and thioridazine-analogs.

Figure 18:
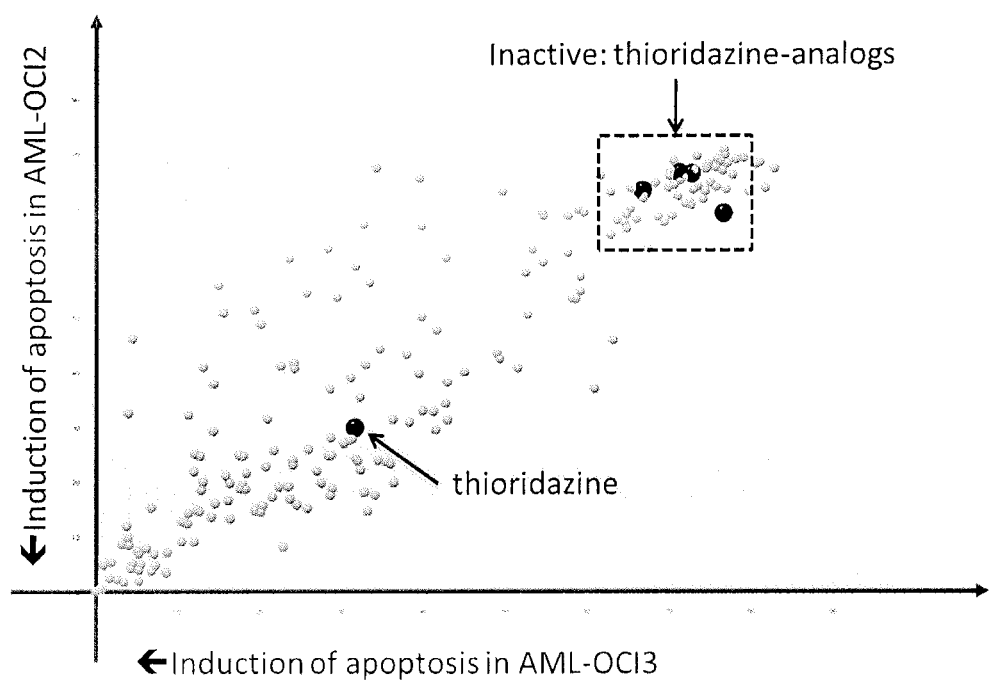
FIG. 18 is a plot showing induction of apoptosis (based on the reduction in percentage of normal nuclei present) after treatment of AML cancer cell lines AML-OCI2 and AML-OCI3 with compounds identified as hits from FIG. 17 (grey dots). Signs of apoptosis increase towards the origin. Black dots refer to thioridazine and thioridazine-analogs. Thioridazine induces cell death in AML cancer cell lines but thioridazine-analogs are inactive. Thioridazine analogs with activity against variant neoplastic stem cells (v1O4 cells) do not induce cell death in AML cancer cell lines.
Figure 19:
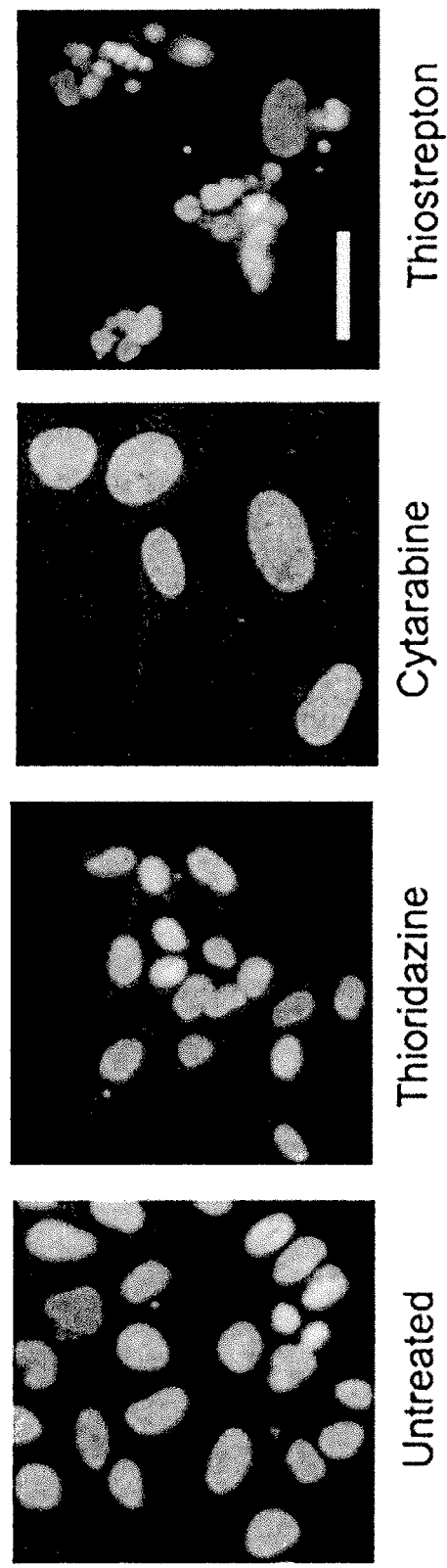
FIG. 19 shows that variant neoplastic stem cells (v1O4 cells) treated with thioridazine show less signs of cell stress/death than cells treated with thiostrepton, as a control that is known to induce apoptosis. Microscopic images of v1O4 cells treated with compounds at 10 μM post 3-day treatment and stained with Hoechst nuclear stain. Thiostrepton is known to induce apoptosis and Cytarabine is a known chemotherapeutic agent for the treatment of AML. Swelling and condensation of the nucleus are signs of cell stress or induction of cell death.

Previously thioridazine was shown to reduce cell numbers in both of the AML-OCI2 and AML-OCI3 (see e.g. PCT/CA2010/000175). AML-OCI2 and AML-OCI3 cells were treated with thioridazine and the cells analyzed for signs of apoptosis-induced cell death. As shown in FIG. 18, thioridazine exerts its effects on these cell lines through cell death, with equal efficiency against AML-OCI2 and AML- OCI3. This contrasts with the differentiation-induced effects of thioridazine on variant neoplastic stem cells. A further demonstration of the utility of the processes disclosed herein is illustrated by the response of the cancer cell lines to thioridazine-analogs. FIGS. 17 and 18 showed that these compounds displayed thioridazine-like activity, including the ability to reduce cell numbers and pluripotency in v1 cells, and produce similar differentiation responses. However, the thioridazine analogs did not significantly induce apoptosis in either AML cancer cell lines; these thioridazine-analogs would have not likely have been identified in a viability screen using these cells.

Accordingly, the use of the screening assays disclosed herein that use variant neoplastic stem cells are significantly different from other screening processes that use cancer cell lines.

Example 15

Compounds Identified as Anti-Cancer Compounds are Rarely Anti-Cancer Stem Cell Compounds The chemical libraries used for screening neoplastic pluripotent stem cells (v1O4 cells) contain compounds that are described as known or current anti-cancer therapeutics. Many of these anti-cancer therapeutics presumably have shown toxicity against cancer cell lines.

Figure 20:
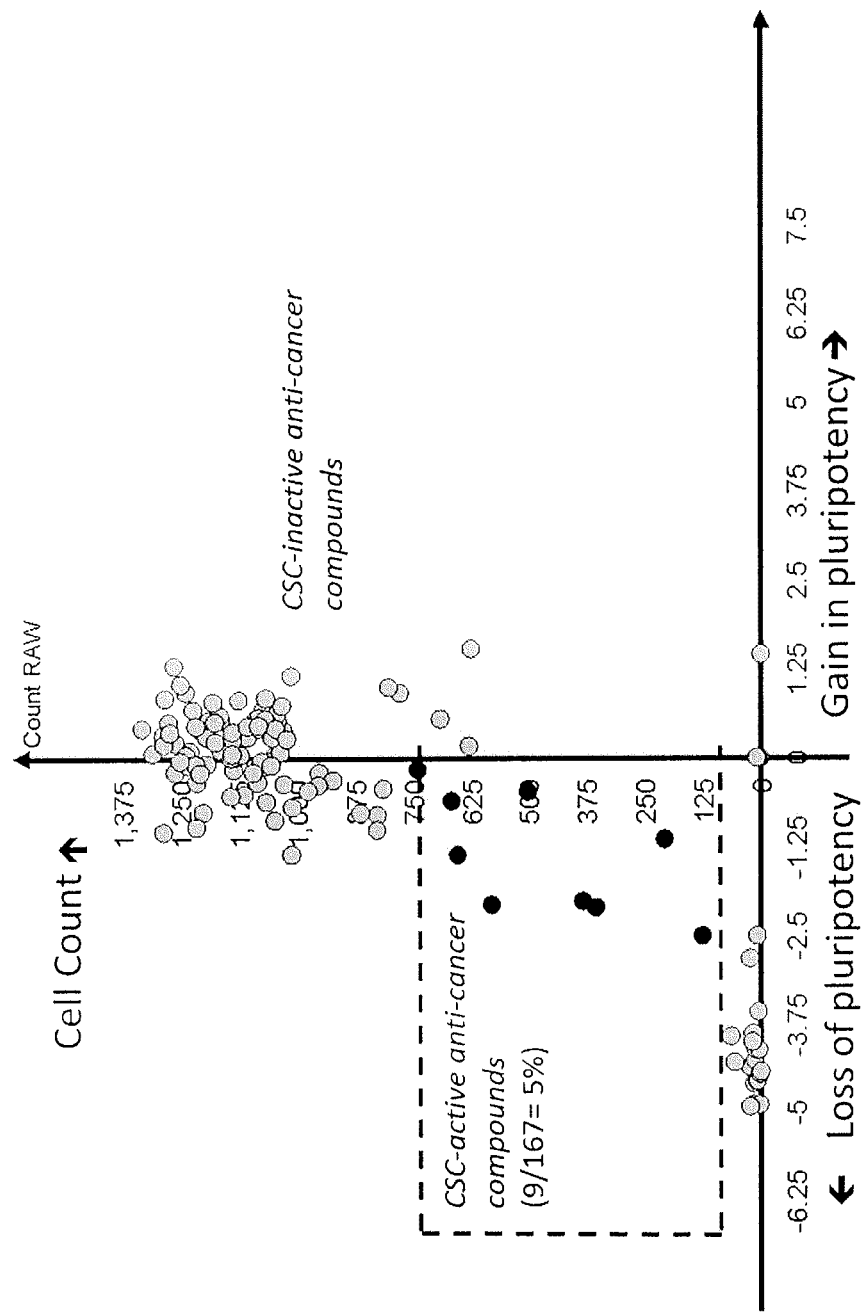
FIG. 20 shows that screening with variant neoplastic stem cells (v1O4 cells) identifies a small subset of anti-cancer compounds that are also active against cancer stem cells (CSCs). All known/current anti-cancer therapeutic compounds were identified from our combined chemical libraries (NIH, PWK, TOCRIS, CCC: 167 in total) and plotted against cell counts and LOP. Only 5% of the known anti-cancer compounds were also determined to be active against cancer stem cells. Anti-cancer compounds that are also anti-cancer stem cell agents are therefore surprisingly rare.

A MetaDrug search was performed for small molecule drugs with available structures that are used in treatment of human cancers ('neoplasms'). This search found 167 such anti-cancer compounds from the combined NIH, PWK, TOCRIS and CCC libraries. These anti-cancer compounds were plotted as shown in FIG. 20 and only a small subset of them (5%) were identified as having activity against variant neoplastic stem cells (v1O4 cells). This suggests that the screening platform described herein such as described in Example 16 is highly stringent or is identifying anti-cancer compounds in a unique manner. Furthermore, compounds identified as anti-cancer compounds are unlikely to be anti-cancer stem cell agents.

Example 16

Improved Workflow for High-Throughput Identification of Compounds that Selectively Target Cancer Stem Cells but not Normal Stem Cells Previously, the present inventors described the effects of thioridazine on variant neoplastic stem cells and normal H9 stem cells using quantitative flow-cytometry to measure levels of Oct4 in both cell types following treatment with three different concentrations of thioridazine (See PCT/CA2010/000175). Only at the highest concentration tested (10 µM) was there a significant difference in loss of pluripotency (based on Oct4 expression) between neoplastic v1 and normal H9 cells (PCT/CA2010/000175). However, quantitative flow-cytometry is not readily amenable to high-throughput analysis.

Figure 21:
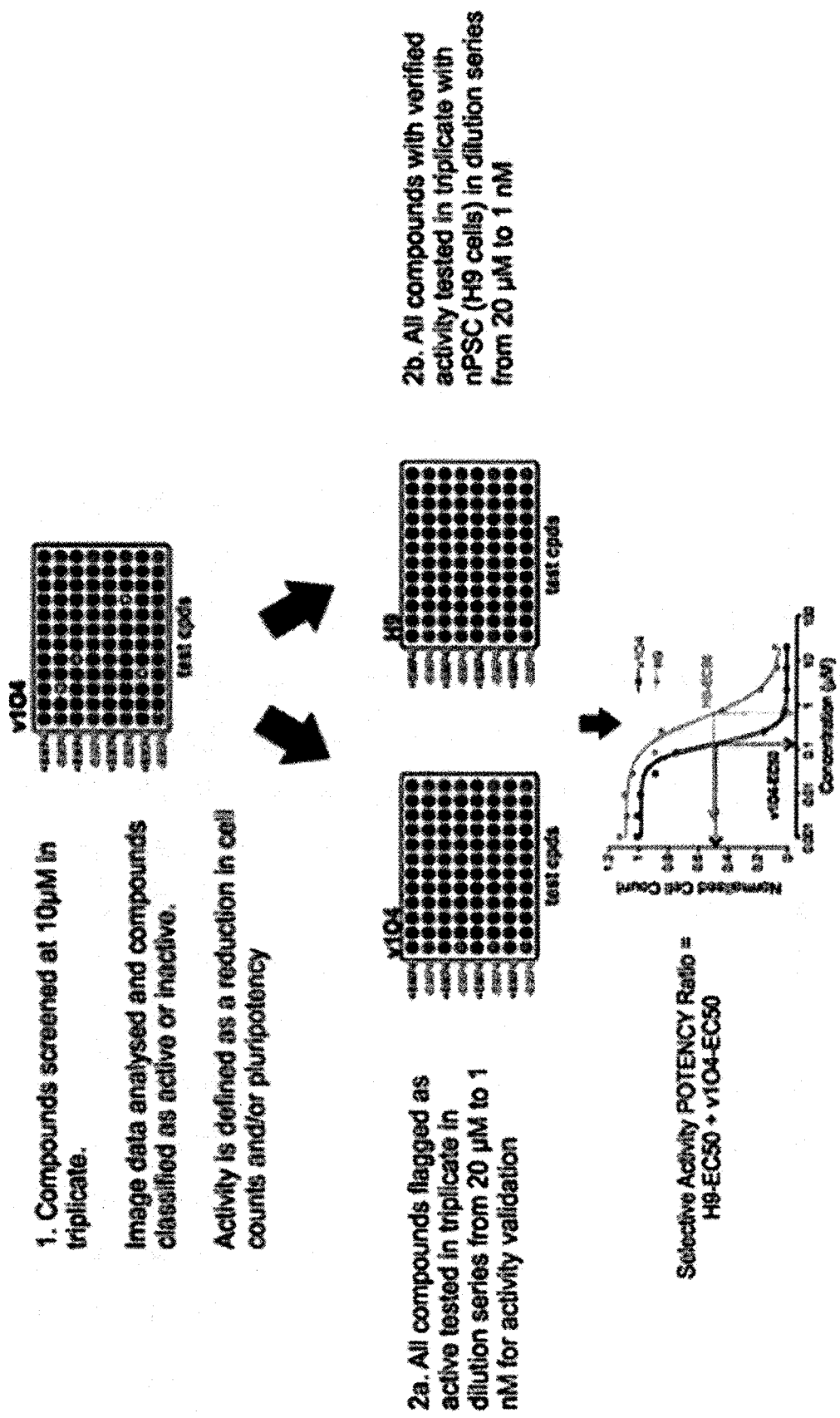
FIG. 21 shows the workflow for a two-stage process for identifying and validating compounds that selectively target cancer stem cells but not normal stem cells. EC50 values from variant neoplastic stem cell (v1O4 cells) and normal stem cell (H9 cells) dose-response curves are used to calculate the selective-activity potency ratio for each compound.
Figure 22:
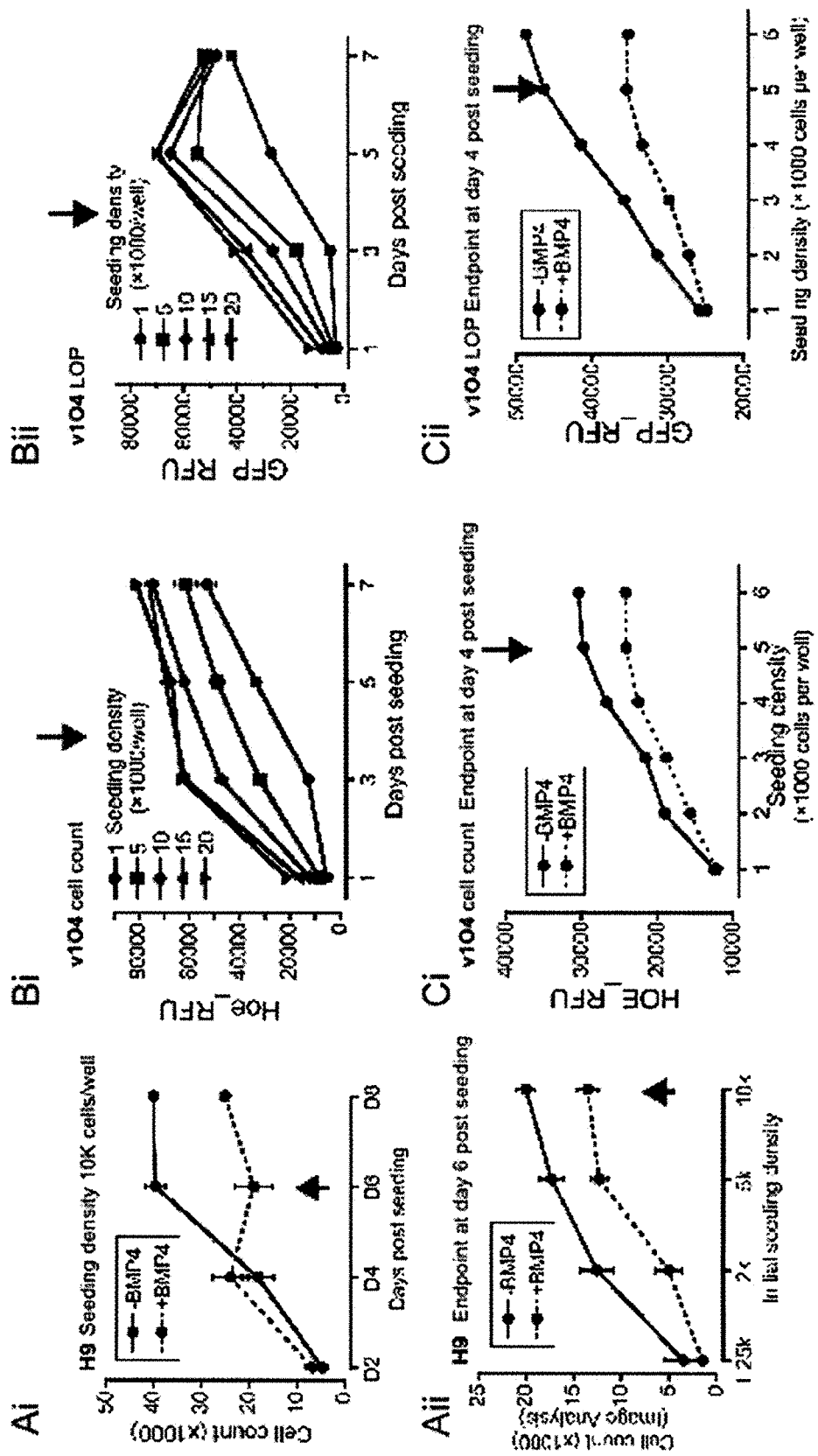
FIG. 22 shows the determination of optimal duration and initial seeding density for normal stem cells (H9 cells) and v1O4 cells for use with high content analysis to determine loss of pluripotency and cell count. Ai Determination of day 6-post seed as optimal time-point in H9. Aii Determination of 10K as optimal for seeding density for H9. Determination of day 4-post seed as optimal time-point based on a range of v1O4 cell seeding densities for Hoechst staining (Bi) and GFP signal (Bii). Determination of 5K v1O4 cell seeding density as optimal for Hoechst staining (Ci) and GFP signal (Cii). H9 and v1O4 cells were seeded onto 96-well plates and treated+/−BMP4 (0.1% DMSO) one day post seeding. The LOP response for v1O4 was quantified 4 days-post seeding using plate fluorimetry and cell counts for H9 was quantified by high content analysis.
Figure 23:
FIG. 23 shows a bar chart identifying compounds with the highest selectivity-activity ratios for cancer stem cells (v1O4 cells).

Here, the inventors disclose improved methods of screening to identify and validate compounds that selectively target cancer stem cells compared to normal stem cells as shown in FIG. 21. The inventors have also determined that seeding the normal stem cells and variant neoplastic stem cells as specific seeding densities as shown in FIG. 22 improves the screening assay and permits the rapid and effective detection of selective anti-cancer stem cell agents. Exemplary candidate compounds identified using this secondary screening procedure are described as having selective activity or alternatively, referred as selective-actives, are shown in FIG. 23.

The first step in the screening process, the primary screen, is shown in FIG. 21, step 1 and is also described in FIG. 17 and Example 13. In this initial screening step, compounds that reduce variant neoplastic stem cell counts and cause a LOP are identified as active compounds or 'hits'. These compounds then undergo a further set of analysis described in FIG. 21, step 2. This stage represents an improvement over previous quantitative flow-cytometry methods for determining compound potency and detecting differences in response between variant neoplastic stem cells and normal stem cells. 8- or 10-point dilutions for each compound are tested on variant neoplastic stem cells (V1O4) and normal stem cells (H9 cells) cells to generate dose-response curves. For each compound, the effective concentration values for 50% reduction in cell counts (EC50) are extrapolated from the dose-response curves from v1O4 and H9 treated cells. Dose response data were fit with a 4-parameter Hill equation to derive EC50, slopes, min and max values using IDBS ActivityBase software. The EC50 values are then used to calculate a selective-activity potency ratio (H9 EC50/v1O4 EC50). A ratio value above 1 indicates the compound is more potent against v1O4 cells than against H9 cells. The ratio values are then used as a basis for identifying high selective-activity compounds that could potentially induce differentiation of cancer stem cells but not normal stem cells. Testing a compound on the variant neoplastic stem cells and the normal stem cells at a number of different concentrations allows for the generation of dose response curves and the identification of compounds which exhibit selective activity that may not be identified by screening at only a single concentration or over a limited range of concentrations. The efficacy of each compound can also be quantified by analysis if the derived min value from the 4-parameter Hill fit. An alternative metric for selective activity is an efficacy comparison. Selective EFFICACY=H9–FittedMin–v1O4–FittedMin.

Example 17

Anti-Cancer Stem Cell Compounds Identified Using High-Selectivity Ratios

Selectivity activity ratios [EC50 (v1O4)/EC50 (H9)] were calculated as discussed in Example 15 for a number of compounds screened using the methods described herein. A ratio value of 3 was selected as a threshold for identifying high selective-activity compounds. These compounds are expected to selectively induce differentiation/toxicity in cancer stem cells but have minimal effects on normal stem cells. The compounds identified using the screening assay with the highest selective-activity ratios are shown in FIG. 23. Surprisingly, the selective-activity potency ratios for thioridazine and thioridazine-analogs were too low to be included in FIG. 23, suggesting the other compounds disclosed herein may have a larger therapeutic window.

Example 18

Analysis of Dose-Response Curves Permits the Identification of Anti-Cancer Stem Cell Agents Most primary high-throughput screening methods use a single concentration point to interrogate the response of an assay due to treatment with a compound. The present disclosure describes assays and conditions for manipulating variant neoplastic stem cells and normal stem cells in order to developing stem cell-based assays for identifying and validating compounds as selective for cancer stem cells. In particular, the methods permit the generation of dose-response curves as shown in FIGS. 21 and 24. Data from these curves was used to distinguish differences in response of variant neoplastic stem cells and normal stem cells to compounds with varying potencies.

Figure 24A:
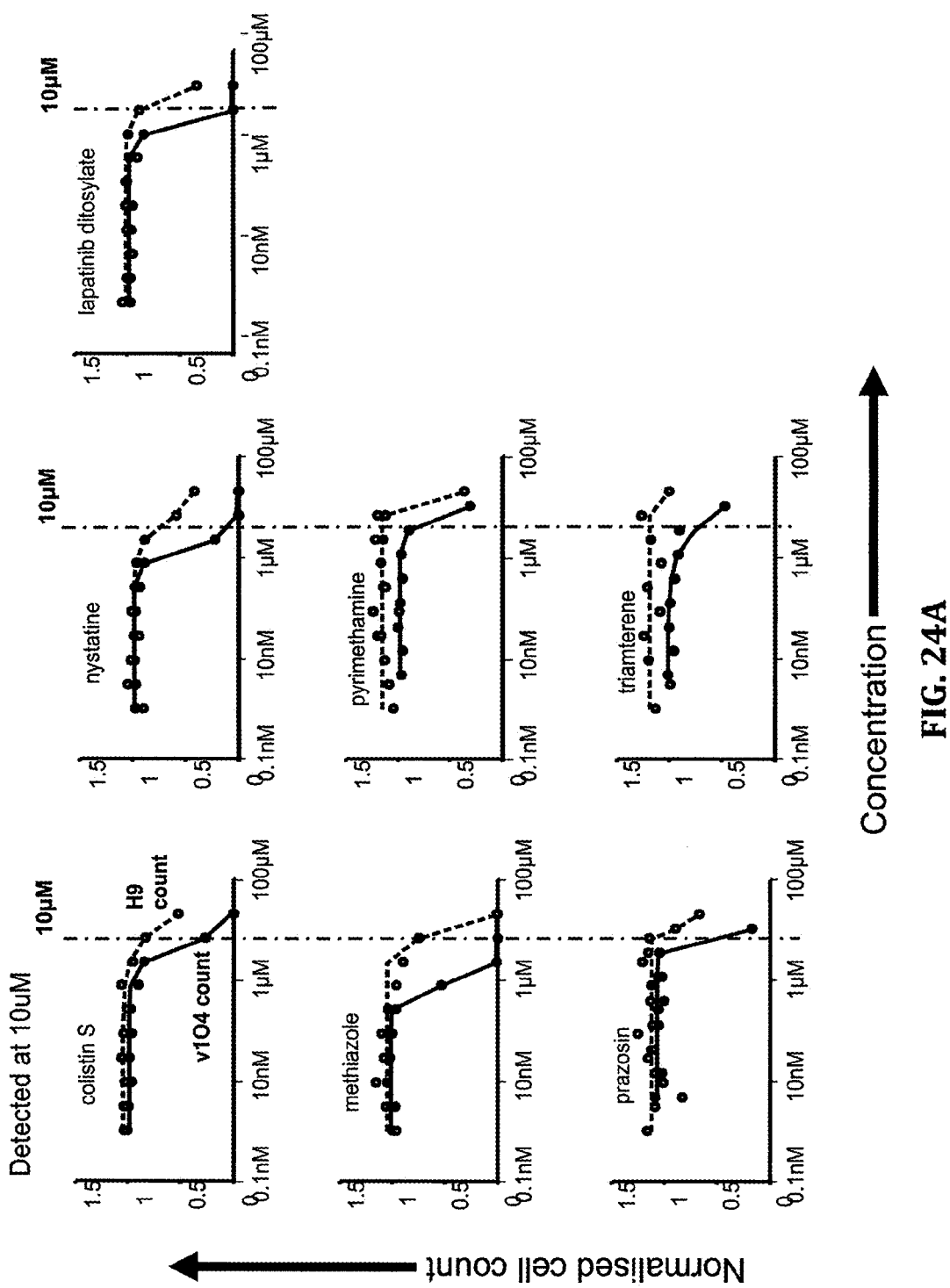
FIG. 24A shows dose-response curves of selective-activity compounds that exhibit selectivity against variant neoplastic stem cells at 10 μM.
Figure 24B:
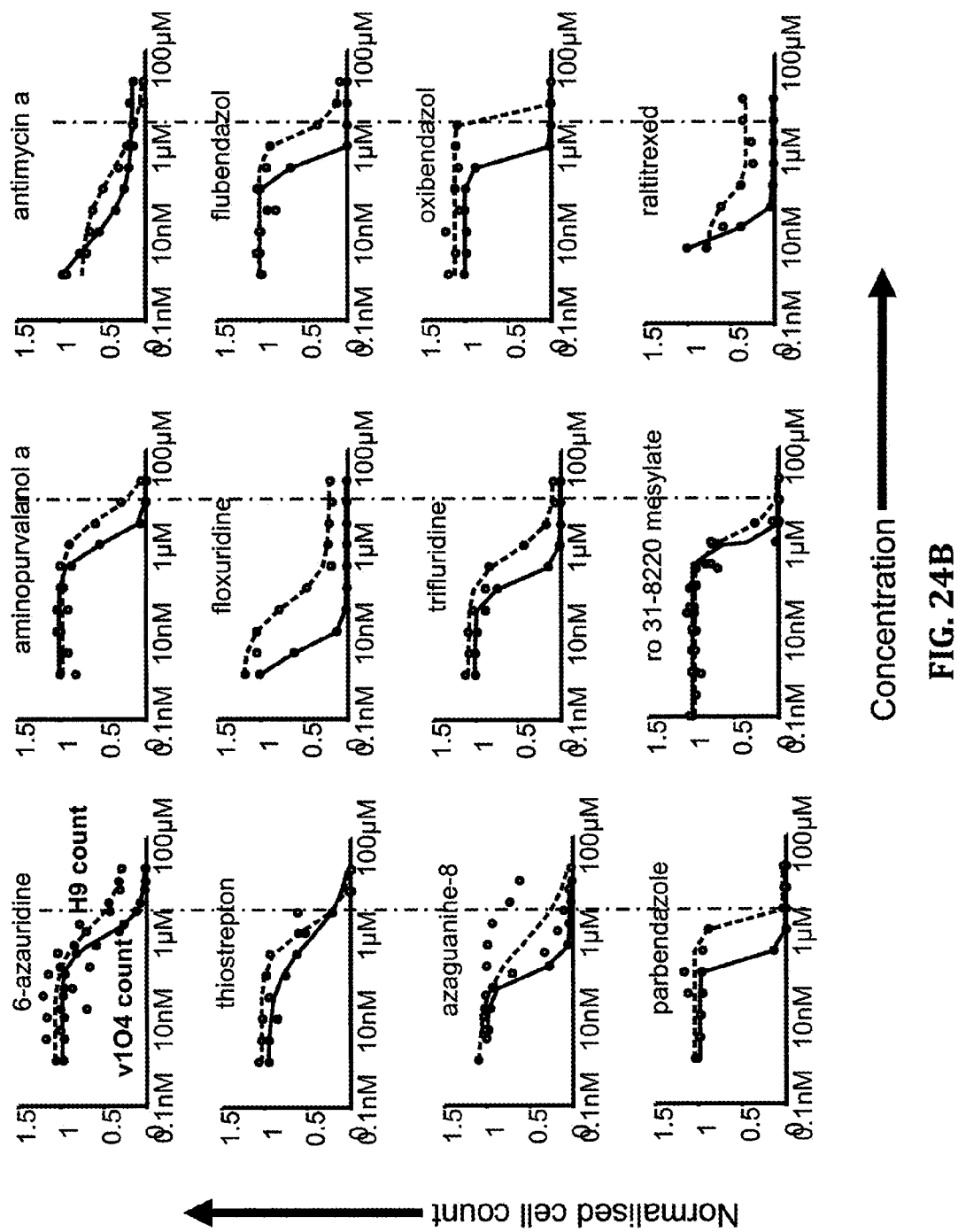
FIG. 24B shows dose-response curves of selective activity compounds that do not necessarily exhibit selectivity at 10 μM but are nevertheless selective at other concentrations. Cell counts are normalised to untreated controls. Dashed line is 10 μM concentration. Screening compounds at a plurality of test concentrations is therefore useful for identifying compounds that are selective for anti-cancer agents.

FIG. 24A shows 7 selective-active compounds that could have been identified by testing the cells at a single 10 µM concentration point. FIG. 24B shows the dose-response curves for the other 12 selective-active compounds. Based on a single 10 µM concentration point, many of these compounds would have not be considered selective for cancer stem cells, such as 8-azaguanine, parbendazole or 31-8220.

Example 19

Some High Selective-Activity Compounds have Low p53 Stress Response Activation Activity AML is characterized by neoplastic hematopoietic cells that are blocked in their ability to differentiate into mature cells. Similarly, variant neoplastic stem cells are also refractory to normal differentiation cues (See Werbowetski-Ogilive et al., 2009). Agents that can induce differentiation of neoplastic progenitor/stem cells represent a promising strategy for the treatment of certain cancers. Treatment of acute promyelocytic leukemia (APL) using all-trans retinoic acid (ATRA) and arsenic trioxide are exemplary applications of this strategy. These compounds are thought to eradicate the cancer cells that maintain the cancer by inducing differentiation.

Figure 25:
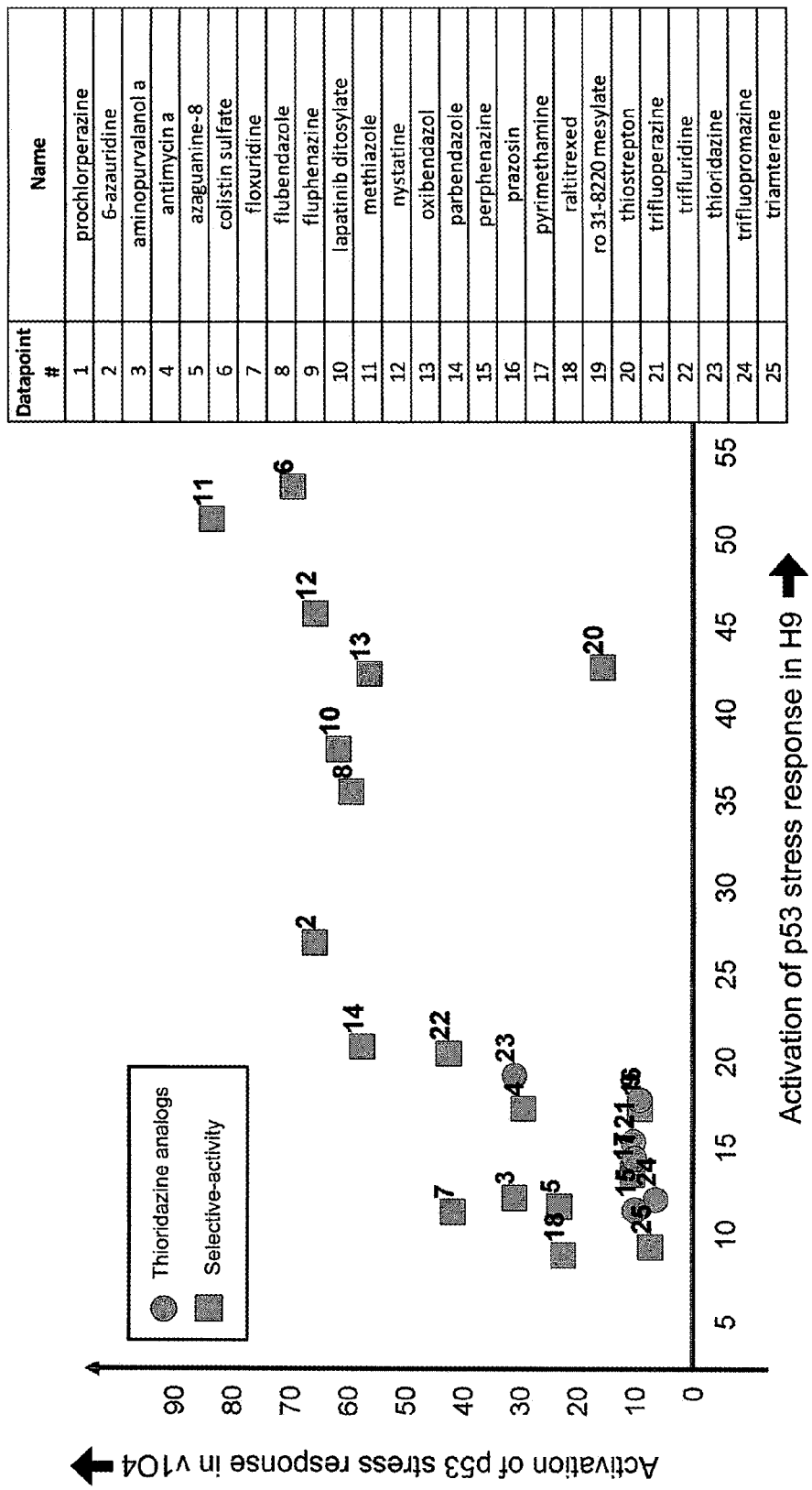
FIG. 25 shows a plot of the percentage of v1O4 or H9 cells that stain positive for p53 after treatment with the high selective-activity compounds (grey) identified in FIG. 23. High levels of p53 indicate activation of the p53-dependent stress response. The black dots represent p53 levels of v1O4 and H9 cells treated with thioridazine and thio-structure-like compounds. High selectivity compounds have varying degrees of p53 stress response activation activity. Thioridazine-analogs shown in FIG. 25 to have little or no activation of the p53 stress response include triflupromazine, prochlorperazine, trifluoperazine, fluphenazine and perphenazine.

To identify compounds demonstrated to have high-selectivity (FIG. 23) that are also efficient in inducing differentiation, treated variant neoplastic stem cells were analyzed for changes in p53-dependent cytotoxic stress response. Variant neoplastic stem cells (v1O4 cells) and normal H9 stem cells were fixed and stained for p53 expression following treatment with selective-activity compounds. The percentage of v1O4 and H9 cells staining positive for p53 were then plotted for each compound as shown in FIG. 25. High levels of p53 activation indicated high cellular toxicity. Although selective-activity compounds caused varying levels of p53 activation in both v1O4 and H9 cells, the v1O4 cells generally appeared more sensitive relative to normal H9 cells.

High selective-activity compounds clustered near the bottom left corner did not significantly increase the p53-dependent stress response in v1O4 and H9 cells. This group may contain potential candidates for compounds that selectively differentiate v1O4 cells. p53 levels of variant neoplastic stem cells treated with thioridazine and thioridazine-analogs were determined and are also shown on FIG. 25 as black dots. As shown in FIG. 25, the thioridazine analogs appeared in this same bottom left corner, consistent with previous observations that they acted on variant neoplastic stem cells by inducing differentiation.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Adewumi, O., Aflatoonian, B., Ahrlund-Richter, L., Amit, M., Andrews, P. W., Beighton, G., Bello, P. A., Benvenisty, N., Berry, L. S., Bevan, S., et al. (2007). Characterization of human embryonic stem cell lines by the International Stem Cell Initiative. Nat. Biotechnol 25, 803-816.

Al-Hajj, M., Wicha, M. S., Benito-Hernandez, A., Morrison, S. J., and Clarke, M. F. (2003). Prospective identification of tumorigenic breast cancer cells. Proc Natl Acad Sci USA 100, 3983-3988.

Beaulieu, J. M., and Gainetdinov, R. R. (2011). The physiology, signaling, and pharmacology of dopamine receptors. Pharmacol Rev 63, 182-217.

Ben-Porath, I., Thomson, M. W., Carey, V. J., Ge, R., Bell, G. W., Regev, A., and Weinberg, R. A. (2008). An embryonic stem cell-like gene expression signature in poorly differentiated aggressive human tumors. Nat Genet. 40, 499-507.

Bhatia, M., Wang, J. C., Kapp, U., Bonnet, D., and Dick, J. E. (1997). Purification of primitive human hematopoietic cells capable of repopulating immune-deficient mice. Proc Natl Acad Sci USA 94, 5320-5325.

Bonnet, D., and Dick, J. E. (1997). Human acute myeloid leukemia is organized as a hierarchy that originates from a primitive hematopoietic cell. Nat Med 3, 730-737.

Boyer, L. A., Lee, T. I., Cole, M. F., Johnstone, S. E., Levine, S. S., Zucker, J. P., Guenther, M. G., Kumar, R. M., Murray, H. L., Jenner, R. G., et al. (2005). Core transcriptional regulatory circuitry in human embryonic stem cells. Cell 122, 947-956.

Breitman, T. R., Collins, S. J., and Keene, B. R. (1981). Terminal differentiation of human promyelocytic leukemic cells in primary culture in response to retinoic acid. Blood 57, 1000-1004.

Breitman, T. R., Selonick, S. E., and Collins, S. J. (1980). Induction of differentiation of the human promyelocytic leukemia cell line (HL-60) by retinoic acid. Proc Natl Acad Sci USA 77, 2936-2940.

Burnett, A. K., Hills, R. K., Green, C., Jenkinson, S., Koo, K., Patel, Y., Guy, C., Gilkes, A., Milligan, D. W., Goldstone, A. H., et al. (2010). The impact on outcome of the addition of all-trans retinoic acid to intensive chemotherapy in younger patients with nonacute promyelocytic acute myeloid leukemia: overall results and results in genotypic subgroups defined by mutations in NPM1, FLT3, and CEBPA Blood 115, 948-956.

Carlo, R. D., Muccioli, G., Bellussi, G., Portaleone, P., Ghi, P., Racca, S, and Carlo, F. D. (1986). Steroid, Prolactin, and Dopamine Receptors in Normal and Pathologic Breast Tissue. Annals of the New York Academy of Sciences 464, 559-562.

Chadwick, K., Wang, L., Li, L., Menendez, P., Murdoch, B., Rouleau, A., and Bhatia, M. (2003). Cytokines and BMP-4 promote hematopoietic differentiation of human embryonic stem cells. Blood 102, 906-915.

Dalton, S. O., Johansen, C., Poulsen, A. H., Norgaard, M., Sorensen, H. T., McLaughlin, J. K., Mortensen, P. B., and Friis, S. (2006). Cancer risk among users of neuroleptic medication: a population-based cohort study. Br J Cancer 95, 934-939.

Dalton, S. O., Mellemkjaer, L., Thomassen, L., Mortensen, P. B., and Johansen, C. (2005). Risk for cancer in a cohort of patients hospitalized for schizophrenia in Denmark, 1969-1993. Schizophr Res 75, 315-324.

Dent, R., Trudeau, M., Pritchard, K. I., Hanna, W. M., Kahn, H. K., Sawka, C. A., Lickley, L. A., Rawlinson, E., Sun, P., and Narod, S. A. (2007). Triple-negative breast cancer: clinical features and patterns of recurrence. Clin Cancer Res 13, 4429-4434.

Desbordes, S. C., Placantonakis, D. G., Ciro, A., Socci, N. D., Lee, G., Djaballah, H., and Studer, L. (2008). High-throughput screening assay for the identification of compounds regulating self-renewal and differentiation in human embryonic stem cells. Cell Stem Cell 2, 602-612.

Diallo, J. S., Le Boeuf, F., Lai, F., Cox, J., Vaha-Koskela, M., Abdelbary, H., MacTavish, H., Waite, K., Falls, T., Wang, J., et al. (2010). A high-throughput pharmacoviral approach identifies novel oncolytic virus sensitizers. Mol Ther 18, 1123-1129.

Dick, J. E. (2008). Stem cell concepts renew cancer research. Blood 112, 4793-4807.

Dick, J. E. (2009). Looking ahead in cancer stem cell research. Nat Biotechnol 27, 44-46.

Driver, J. A., Logroscino, G., Buring, J. E., Gaziano, J. M., and Kurth, T. (2007). A prospective cohort study of cancer incidence following the diagnosis of Parkinson's disease. Cancer Epidemiol Biomarkers Prev 16, 1260-1265.

Eppert, K., Takenaka, K., Lechman, E. R., Waldron, L., Nilsson, B., van Galen, P., Metzeler, K. H., Poeppl, A., Ling, V., Beyene, J., et al. (2011). Stem cell gene expression programs influence clinical outcome in human leukemia. Nature Medicine doi:10. 1038/nm.2415.

Estey, E., and Dohner, H. (2006). Acute myeloid leukaemia. Lancet 368, 1894-1907.

Fibach, E., Hayashi, M., and Sachs, L. (1973). Control of normal differentiation of myeloid leukemic cells to macrophages and granulocytes. Proc Natl Acad Sci USA 70, 343-346.

Frese, K. K., and Tuveson, D. A. (2007). Maximizing mouse cancer models. Nat Rev Cancer 7, 645-658.

Friend, C., Scher, W., Holland, J. G., and Sato, T. (1971). Hemoglobin synthesis in murine virus-induced leukemic cells in vitro: stimulation of erythroid differentiation by dimethyl sulfoxide. Proc Natl Acad Sci USA 68, 378-382.

Guan, Y., Gerhard, B., and Hogge, D. E. (2003). Detection, isolation, and stimulation of quiescent primitive leukemic progenitor cells from patients with acute myeloid leukemia (AML). Blood 101, 3142-3149.

Gupta, P. B., Onder, T. T., Jiang, G., Tao, K., Kuperwasser, C., Weinberg, R. A., and Lander, E. S. (2009). Identification of selective inhibitors of cancer stem cells by high-throughput screening. Cell 138, 645-659.

Hotta, A., Cheung, A. Y., Farra, N., Vijayaragavan, K., Seguin, C. A., Draper, J. S., Pasceri, P., Maksakova, I. A., Mager, D. L., Rossant, J., et al. (2009). Isolation of human iPS cells using EOS lentiviral vectors to select for pluripotency. Nat Methods 6, 370-376.

Inglese, J., Shamu, C. E., and Guy, R. K. (2007). Reporting data from high-throughput screening of small-molecule libraries. Nat Chem Biol 3, 438-441.

Jemal, A., Siegel, R., Xu, J., and Ward, E. (2010). Cancer statistics, 2010. CA Cancer J Clin 60, 277-300.

Jordan, C. T. (2009). Cancer stem cells: controversial or just misunderstood? Cell Stem Cell 4, 203-205.

Koistinen P et al., Regulation of the acute myeloid leukemia cell line OCI/AML-2 by endothelial nitric oxide synthase under the control of a vascular endothelial growth factor signaling system. Leukemia. 2001 September; 15(9): 1433-41.

Lapidot, T., Sirard, C., Vormoor, J., Murdoch, B., Hoang, T., Caceres-Cortes, J., Minden, M., Paterson, B., Caligiuri, M. A., and Dick, J. E. (1994). A cell initiating human acute myeloid leukaemia after transplantation into SCID mice. Nature 367, 645-648.

Lee, J. Y., Nakada, D., Yilmaz, O. H., Tothova, Z., Joseph, N. M., Lim, M. S., Gilliland, D. G., and Morrison, S. J. (2010). mTOR activation induces tumor suppressors that inhibit leukemogenesis and deplete hematopoietic stem cells after Pten deletion. Cell Stem Cell 7, 593-605.

Li, X., Lewis, M. T., Huang, J., Gutierrez, C., Osborne, C. K., Wu, M. F., Hilsenbeck, S. G., Pavlick, A., Zhang, X., Chamness, G. C., et al. (2008). Intrinsic resistance of tumorigenic breast cancer cells to chemotherapy. J Natl Cancer Inst 100, 672-679.

Little, K. Y., Elmer, L. W., Zhong, H., Scheys, J. O., and Zhang, L. (2002). Cocaine induction of dopamine transporter trafficking to the plasma membrane. Mol Pharmacol 61, 436-445.

Machaliński B, Wiszniewska B, Baśkiewicz M, Marchlewicz M, Majka M, Wenda-Rózewicka L, Ratajczak M Z. (1998) In vivo and in vitro studies on the toxicity of Hoechst 33342 (Ho342). Implications for employing Ho342 for the isolation of haematopoietic stem cells. Ann Transplant. 3 (3):5-13

Nasr, R., Guillemin, M. C., Ferhi, O., Soilihi, H., Peres, L., Berthier, C., Rousselot, P., Robledo-Sarmiento, M., Lallemand-Breitenbach, V., Gourmel, B., et al. (2008). Eradication of acute promyelocytic leukemia-initiating cells through PML-RARA degradation. Nat Med 14, 1333-1342.

Nichols, J., Zevnik, B., Anastassiadis, K., Niwa, H., Klewe-Nebenius, D., Chambers, I., Scholer, H., and Smith, A. (1998). Formation of pluripotent stem cells in the mammalian embryo depends on the POU transcription factor Oct4. Cell 95, 379-391.

Niu, C., Yan, H., Yu, T., Sun, H. P., Liu, J. X., Li, X. S., Wu, W., Zhang, F. Q., Chen, Y., Zhou, L., et al. (1999). Studies on treatment of acute promyelocytic leukemia with arsenic trioxide: remission induction, follow-up, and molecular monitoring in 11 newly diagnosed and 47 relapsed acute promyelocytic leukemia patients. Blood 94, 3315-3324.

Niwa, H., Miyazaki, J., and Smith, A. G. (2000). Quantitative expression of Oct-3/4 defines differentiation, dedifferentiation or self-renewal of ES cells. Nat Genet. 24, 372-376.

Raj, L., Ide, T., Gurkar, A. U., Foley, M., Schenone, M., Li, X., Tolliday, N. J., Golub, T. R., Carr, S. A., Shamji, A. F., et al. (2011). Selective killing of cancer cells by a small molecule targeting the stress response to ROS. Nature 475, 231-234.

Recher, C., Beyne-Rauzy, O., Demur, C., Chicanne, G., Dos Santos, C., Mas, V. M., Benzaquen, D., Laurent, G., Huguet, F., and Payrastre, B. (2005). Antileukemic activity of rapamycin in acute myeloid leukemia. Blood 105, 2527-2534.

Reya, T., Morrison, S. J., Clarke, M. F., and Weissman, I. L. (2001). Stem cells, cancer, and cancer stem cells. Nature 414, 105-111.

Sachs, L. (1978a). Control of normal cell differentiation and the phenotypic reversion of malignancy in myeloid leukaemia. Nature 274, 535-539.

Sachs, L. (1978b). The differentiation of myeloid leukaemia cells: new possibilities for therapy. Br J Haematol 40, 509-517.

Sanz, M. A. (2006). Treatment of acute promyelocytic leukemia. Hematology Am Soc Hematol Educ Program, 147-155.

Sanz, M. A., Grimwade, D., Tallman, M. S., Lowenberg, B., Fenaux, P., Estey, E. H., Naoe, T., Lengfelder, E., Buchner, T., Dohner, H., et al. (2009). Management of acute promyelocytic leukemia: recommendations from an expert panel on behalf of the European LeukemiaNet. Blood 113, 1875-1891.

Seeman, P., and Lee, T. (1975). Antipsychotic drugs: direct correlation between clinical potency and presynaptic action on dopamine neurons. Science 188, 1217-1219.

Self, D. W., Barnhart, W. J., Lehman, D. A., and Nestler, E. J. (1996). Opposite modulation of cocaine-seeking behavior by D1- and D2-like dopamine receptor agonists. Science 271, 1586-1589.

Shoemaker, R. H. (2006). The NCI60 human tumour cell line anticancer drug screen. Nat Rev Cancer 6, 813-823.

Sibley, D. R., and Monsma, F. J., Jr. (1992). Molecular biology of dopamine receptors. Trends Pharmacol Sci 13, 61-69.

Smith, B. D., Levis, M., Beran, M., Giles, F., Kantarjian, H., Berg, K., Murphy, K. M., Dauses, T., Allebach, J., and Small, D. (2004). Single-agent CEP-701, a novel FLT3 inhibitor, shows biologic and clinical activity in patients with relapsed or refractory acute myeloid leukemia. Blood 103, 3669-3676.

Smith, T. J., Khatcheressian, J., Lyman, G. H., Ozer, H., Armitage, J. O., Balducci, L., Bennett, C. L., Cantor, S. B., Crawford, J., Cross, S. J., et al. (2006). 2006 update of recommendations for the use of white blood cell growth factors: an evidence-based clinical practice guideline. J Clin Oncol 24, 3187-3205.

Taussig, D. C., Miraki-Moud, F., Anjos-Afonso, F., Pearce, D. J., Allen, K., Ridler, C., Lillington, D., Oakervee, H., Cavenagh, J., Agrawal, S. G., et al. (2008). Anti-CD38 antibody-mediated clearance of human repopulating cells masks the heterogeneity of leukemia-initiating cells. Blood 112, 568-575.

Tefferi et al. Cancer, September 1$^{st}$, pp. 3842-3847 (2009)

Vannucchi et al. Advances in Understanding and Management of Myeloproliferative Neoplasms CA Cancer J. Clin. 2009; 59:171-191

Visvader, J. E., and Lindeman, G. J. (2008). Cancer stem cells in solid tumours: accumulating evidence and unresolved questions. Nat Rev Cancer 8, 755-768.

Wang, Z. Y., and Chen, Z. (2008). Acute promyelocytic leukemia: from highly fatal to highly curable. Blood 111, 2505-2515.

Werbowetski-Ogilvie, T. E., Bosse, M., Stewart, M., Schnerch, A., Ramos-Mejia, V., Rouleau, A., Wynder, T., Smith, M. J., Dingwall, S., Carter, T., et al. (2009). Characterization of human embryonic stem cells with features of neoplastic progression. Nat Biotechnol 27, 91-97.

Xu, R. H., Chen, X., Li, D. S., Li, R., Addicks, G. C., Glennon, C., Zwaka, T. P., and Thomson, J. A. (2002). BMP4 initiates human embryonic stem cell differentiation to trophoblast. Nat Biotechnol 20, 1261-1264.

Yilmaz, O. H., Valdez, R., Theisen, B. K., Guo, W., Ferguson, D. O., Wu, H., and Morrison, S. J. (2006). Pten dependence distinguishes haematopoietic stem cells from leukaemia-initiating cells. Nature 441, 475-482.

Ying, Q. L., Nichols, J., Chambers, I., and Smith, A. (2003). BMP induction of Id proteins suppresses differentiation and sustains embryonic stem cell self-renewal in collaboration with STAT3. Cell 115, 281-292.

Yoshida, H., Kitamura, K., Tanaka, K., Omura, S., Miyazaki, T., Hachiya, T., Ohno, R., and Naoe, T. (1996). Accelerated degradation of PML-retinoic acid receptor alpha (PML-RARA) oncoprotein by all-trans-retinoic acid in acute promyelocytic leukemia: possible role of the proteasome pathway. Cancer Res 56, 2945-2948.

Zhelev, Z., Ohba, H., Bakalova, R., Hadjimitova, V., Ishikawa, M., Shinohara, Y., and Baba, Y. (2004). Phenothiazines suppress proliferation and induce apoptosis in cultured leukemic cells without any influence on the viability of normal lymphocytes. Phenothiazines and leukemia. Cancer Chemother Pharmacol 53, 267-275.

Zheng, R., Friedman, A. D., and Small, D. (2002). Targeted inhibition of FLT3 overcomes the block to myeloid differentiation in 32Dcl3 cells caused by expression of FLT3/ITD mutations. Blood 100, 4154-4161.

Zhu, J., Koken, M. H., Quignon, F., Chelbi-Alix, M. K., Degos, L., Wang, Z. Y., Chen, Z., and de The, H. (1997). Arsenic-induced PML targeting onto nuclear bodies: implications for the treatment of acutepromyelocytic leukemia. Proc Natl Acad Sci USA 94, 3978-3983.

The invention claimed is:

1. A method for identifying and validating a test agent as a selective anti-cancer stem cell agent, the method comprising:
   i) contacting one or more variant neoplastic stem cells with the test agent and one or more normal stem cells with the test agent,
   wherein said variant neoplastic stem cells are transformed human Pluripotent Stem Cells or transformed induced Pluripotent Stem Cells characterized as having at least one property selected from
      an ability to differentiate into more than one cell type without requiring Oct4 for self-renewal or survival,
      an ability to co-express FGFR1 and IGFR1,
      an ability to maintain an undifferentiated state in culture absent the presence of fibroblast growth factor (bFGF),
      an ability to maintain the expression of SSEA3 in the absence of bFGF, and
      a requirement of the presence of Nanog for self-renewal and cell survival;
   ii) detecting a change in cell count of the variant neoplastic stem cells in response to the test agent, and detecting a change in cell count of the normal stem cells in response to the test agent; and
   iii) identifying the test agent as a selective anti-cancer stem cell agent if contact with the test agent induces a decrease in cell count of the variant neoplastic stem cells without inducing a comparable decrease in the normal stem cells;
   wherein the variant neoplastic stem cells are seeded in a first receptacle at about 3000 to 7000 cells per receptacle and the normal stem cells are seeded in a second receptacle at about 8000 to 12000 cells per receptacle.

2. The method of claim 1, further comprising, contacting the variant neoplastic stem cells and the normal stem cells with the test agent at a plurality of test concentrations and detecting a change in cell count for the one or more variant neoplastic stem cells and for the normal stem cells at the plurality of test concentrations.

3. The method of claim 2, wherein the plurality of test concentrations varies by at least about 3, 4 or 5 orders of magnitude.

4. The method of claim 2, wherein the plurality of concentrations varies from about 10 nM to about 20 µM.

5. The method of claim 2, wherein the plurality of test concentrations comprises at least an 8 point dilution series.

6. The method of claim 2, wherein step iii) comprises comparing a dose-response curve for the change in cell count of the variant neoplastic stem cells in response to contact with the test agent at the plurality of test concentrations to a dose-response curve for the change in cell count of the normal stem cells in response to contact with the test agent at the plurality of test concentrations.

7. The method of claim 6, further comprising determining for the test agent a half maximal effective concentration (EC50) value for decrease in cell count for the variant neoplastic stem cells, and an EC50 value for decrease in cell count in the normal stem cells.

8. The method of claim 7, further comprising determining a ratio of the EC50 value for decrease in cell count for the normal stem cells relative to the EC50 value for decrease in cell count for the variant neoplastic stem cells.

9. The method of claim 8, wherein step iii) comprises identifying the test agent as a selective anti-cancer stem cell agent if the ratio of the EC50 values is greater than 3.

10. The method of claim 1, wherein the variant neoplastic stem cells are seeded at about 4000 to 6000 cells per receptacle.

11. The method of claim 1, wherein the normal stem cells are seeded at about 9000 to 11000 cells per receptacle.

12. The method of claim 1, wherein the change in cell count for the variant neoplastic stem cells is detected between about 48 hours and 96 hours after contacting the cells with the test agent, and the change in cell count for the normal stem cells is detected between about 4 days and 6 days after contacting the cells with the test agent.

13. The method of claim 1, further comprising screening the test agent identified as a selective anti-cancer stem cell agent for activity on a cancer cell line derived from a subject with cancer.

14. The method of claim 13, wherein the cancer cell line is a leukemic cell line.

15. The method of claim 1, further comprising prior to step i) screening one or more agents to identify one or more test agents that induce loss of pluripotency and a decrease in cell count of variant neoplastic stem cells.

16. The method of claim 15, comprising prior to step i) contacting the variant neoplastic stem cells with the agent, detecting a change in pluripotency and a change in cell count of the variant neoplastic stem cells in response to the agent and selecting an agent as the test agent if the agent induces a loss of pluripotency and a decrease in cell count of the variant neoplastic stem cells.

17. The method of claim 16, wherein a plurality of agents are screened on a microtiter plate and identified as test agents based on a threshold standard deviation from the mean.

18. A two-stage method for identifying and validating an agent as a selective anti-cancer stem cell agent, the method comprising:

i) detecting a change in pluripotency and a change in cell count of variant neoplastic stem cells in response to contact with the agent and selecting an agent as a test agent if the agent induces a loss of pluripotency and/or a decrease in cell count of the variant neoplastic stem cells; and ii) contacting one or more variant neoplastic stem cells with the test agent and contacting one or more normal stem cells with the test agent, detecting a change in cell count of the variant neoplastic stem cells in response to the test agent at a plurality of test concentrations, detecting a change in cell count of the normal stem cells in response to the test agent at a plurality of test concentrations, and identifying the test agent as a selective anti-cancer stem cell agent if the test agent induces a decrease in cell count of the variant neoplastic stem cells without inducing a comparable decrease in the normal stem cells;

wherein the variant neoplastic stem cells are transformed human Pluripotent Stem Cells or transformed induced Pluripotent Stem Cells characterized as having at least one property selected from an ability to differentiate into more than one cell type without requiring Oct4 for self-renewal or survival, an ability to co-express FGFR1 and IGFR1, an ability to maintain an undifferentiated state in culture absent the presence of fibroblast growth factor (bFGF), an ability to maintain the expression of SSEA3 in the absence of bFGF, and a requirement of the presence of Nanog for self-renewal and cell survival; and wherein the variant neoplastic stem cells are seeded in a first receptacle at about 3000 to 7000 cells per receptacle and the normal stem cells are seeded in a second receptacle at about 8000 to 12000 cells per receptacle.

19. The method of claim 18, wherein the plurality of test concentrations varies by at least about 3, 4 or 5 orders of magnitude.

20. The method of claim 18, wherein the plurality of concentrations varies from about 10 nM to about 10 µM.

21. The method of claim 18, wherein the plurality of test concentrations comprises at least an 8 point dilution series.

22. The method of claim 18, wherein step ii comprises comparing a dose-response curve for the change in cell count of the variant neoplastic stem cells in response to contact with the test agent at the plurality of test concentrations to a dose-response curve for the change in cell count of the normal stem cells in response to contact with the test agent at the plurality of test concentrations.

23. The method of claim 18, further comprising determining for the test agent an EC50 value for a decrease in cell count for the variant neoplastic stem cells, and an EC50 value for a decrease in cell count for the normal stem cells.

24. The method of claim 23, further comprising determining a ratio of the EC50 value for the decrease in cell for count for the normal stem cells relative to the EC50 value for the decrease in cell count for the variant neoplastic stem cells.

25. The method of claim 24, further comprising identifying the test agent as a selective anti-cancer stem cell agent if the ratio of the EC50 values is greater than 3.

26. The method of claim 18, wherein the variant neoplastic stem cells are seeded at about 4000 to 6000 cells per receptacle.

27. The method of claim 18, wherein the normal stem cells are seeded at about 9000 to 11000 cells per receptacle.

28. The method of claim 18, wherein the change in cell count for the variant neoplastic stem cells is detected between about 48 hours and 96 hours after contacting the cells with the test agent, and the change in cell count for the normal stem cells is detected between about 4 days and 6 days after contacting the cells with the test agent, and the change in pluripotency for the variant neoplastic stem cells is detected between 48 and 96 hours after contacting the variant neoplastic stem cells with the test agent.

29. The method of claim 18, further comprising screening the test agent identified as a selective anti-cancer stem cell agent for activity on a cancer cell line derived from a subject with cancer.

30. The method of claim 29, wherein the cancer cell line is a leukemic cell line.

31. The method of claim 4, wherein the plurality of concentrations varies from about 0.01 µM to about 2 µM.

32. The method of claim 14, wherein the cancer cell line is an acute myeloid leukemia (AML) cell line.

33. The method of claim 20, wherein the plurality of concentrations varies from about 0.01 µM to about 1 µM.

34. The method of claim 30, wherein the cancer cell line is an acute myeloid leukemia (AML) cell line.

* * * * *